(12) United States Patent
Jaroskova et al.

(10) Patent No.: US 8,344,181 B2
(45) Date of Patent: Jan. 1, 2013

(54) N-2 ADAMANTANYL-2-PHENOXY-ACETAMIDE DERIVATIVES AS 11-BETA HYDROXYSTEROID DEHYDROGENASE INHIBITORS

(75) Inventors: Libuse Jaroskova, Vosselaar (BE); Joannes Theodorus Maria Linders, Eindhoven (NL); Louis Jozef Elisabeth Van Der Veken, Vosselaar (BE); Gustaaf Henri Maria Willemsens, Beerse (BE); François Paul Bischoff, Vosselaar (BE)

(73) Assignee: Janssen Pharmaceutica N.V., Beerse (BE)

( * ) Notice: Subject to any disclaimer, the term of this patent is extended or adjusted under 35 U.S.C. 154(b) by 686 days.

(21) Appl. No.: 11/661,470

(22) PCT Filed: Aug. 26, 2005

(86) PCT No.: PCT/EP2005/054197
§ 371 (c)(1),
(2), (4) Date: Feb. 26, 2007

(87) PCT Pub. No.: WO2006/024627
PCT Pub. Date: Mar. 9, 2006

(65) Prior Publication Data
US 2008/0064693 A1    Mar. 13, 2008

Related U.S. Application Data

(60) Provisional application No. 60/607,851, filed on Sep. 8, 2004.

(30) Foreign Application Priority Data

Aug. 30, 2004    (EP) .................................. 04104152

(51) Int. Cl.
C07C 233/05    (2006.01)
A61K 31/16    (2006.01)

(52) U.S. Cl. ........ 564/162; 564/168; 564/182; 514/618; 514/619; 514/456; 514/469; 549/405; 549/467; 549/468

(58) Field of Classification Search .................. 564/162, 564/163, 165, 168, 182; 514/618, 619; 549/405, 549/467, 468
See application file for complete search history.

(56) References Cited

U.S. PATENT DOCUMENTS 2,510,945 A    6/1950  Badgett et al.
2,524,643 A    10/1950 Walter et al.
3,526,656 A    9/1970  Butler (Continued)

FOREIGN PATENT DOCUMENTS

CA    2017287 A1    11/1990

(Continued)

OTHER PUBLICATIONS

Chemical Abstract: Database CHEMCATS AN 2002: 1350644; Oct. 2003.

(Continued)

*Primary Examiner* — Shailendra Kumar

(57) ABSTRACT

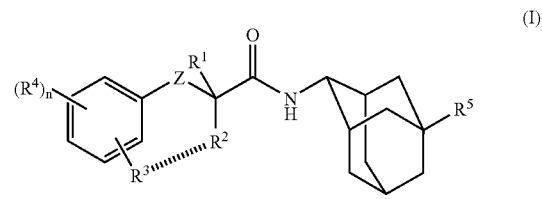

the N-oxide forms, the pharmaceutically acceptable addition salts and the stereochemically isomeric forms thereof, wherein Z represents O, S, $NR^6$, SO or $SO_2$;

Figure 1:
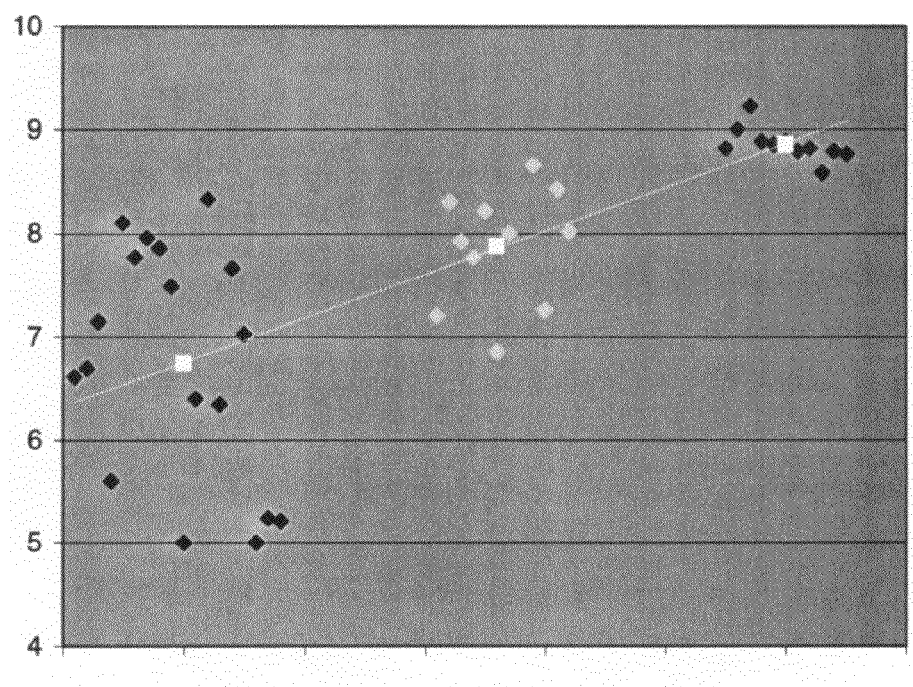

$R^1$ represents hydrogen, cyano, hydroxy, or $C_{1-4}$alkyl optionally substituted with halo, $R^2$ represents hydrogen, $C_{1-4}$alkyl, or $C_{1-4}$alkyloxy-;

$R^3$ represents hydrogen, $C_{1-4}$alkyl, $C_{1-4}$alkyloxy- or $R^3$ combined with $R^2$ form together a divalent radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;

$R^4$ represents hydrogen, halo, hydroxy, cyano, amino, $NR^{11}R^{12}$, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;

$R^5$ represents hydrogen, halo, cyano, amino, phenyl, hydroxy, $C_{1-4}$alkyloxycarbonyl, hydroxycarbonyl, $NR^{13}R^{14}$ or $C_{1-4}$alkyl substituted with one or more substituents selected from hydroxycarbonyl, phenyl, $C_{1-4}$alkyloxy or $NR^{15}R^{16}$;

$R^6$ represents hydrogen;

$R^{11}$ and $R^{12}$ each independently represent hydrogen, $C_{1-4}$alkyl or $C_{1-4}$alkylcarbonyl-;

$R^{13}$ and $R^{14}$ each independently represent hydrogen, $C_{1-4}$alkyl or $C_{1-4}$alkylcarbonyl-;

$R^{15}$ and $R^{16}$ each independently represent hydrogen, $C_{1-4}$alkyl or $C_{1-4}$alkylcarbonyl-;

$R^{17}$ and $R^{18}$ each independently represent hydrogen, $C_{1-4}$alkyl or $C_{1-4}$alkylcarbonyl-.

19 Claims, 1 Drawing Sheet

U.S. PATENT DOCUMENTS

| | | | |
|---|---|---|---|
| 3,622,567 | A | 11/1971 | Razdan |
| 3,919,313 | A | 11/1975 | Villani |
| 5,356,907 | A | 10/1994 | Clemence et al. |
| 5,395,843 | A | 3/1995 | Clemence et al. |
| 5,541,343 | A | 7/1996 | Himmelsbach et al. |
| 5,559,130 | A | 9/1996 | Clemence et al. |
| 5,776,959 | A | 7/1998 | Covey et al. |
| 6,194,406 | B1 | 2/2001 | Kane et al. |
| 6,211,199 | B1 | 4/2001 | Kane et al. |
| 6,555,572 | B2 | 4/2003 | Lauener et al. |
| 7,332,524 | B2 | 2/2008 | Linders et al. |
| 7,687,644 | B2 | 3/2010 | Jaroskova et al. |
| 7,968,601 | B2 | 6/2011 | Linders et al. |
| 2001/0034343 | A1 | 10/2001 | Maynard et al. |
| 2003/0087952 | A1 | 5/2003 | Wood et al. |
| 2005/0245534 | A1* | 11/2005 | Link et al. ............. 514/252.12 |
| 2008/0139625 | A1 | 6/2008 | Jaroskova et al. |
| 2008/0214597 | A1 | 9/2008 | Jaraskova et al. |

FOREIGN PATENT DOCUMENTS

| | | |
|---|---|---|
| DE | 1959898 A1 | 6/1970 |
| DE | 2624290 A1 | 4/1977 |
| EP | 117462 A2 | 9/1984 |
| EP | 0399814 A2 | 11/1990 |
| EP | 0437120 B1 | 8/1995 |
| EP | 00481522 B1 | 12/1997 |
| EP | 1 127 883 A | 8/2001 |
| EP | 0873336 B1 | 3/2003 |
| FR | 1399615 | 5/1965 |
| FR | 2714291 A | 6/1995 |
| GB | 1065533 | 4/1967 |
| GB | 2136801 A | 12/1984 |
| JP | 59 164779 | 9/1984 |
| JP | 59 175472 A | 10/1984 |
| JP | 03-086853 | 4/1991 |
| JP | 9 501650 | 2/1997 |
| JP | 11 506471 | 6/1999 |
| WO | WO 95/00493 A1 | 1/1995 |
| WO | WO 96/04254 A | 2/1996 |
| WO | WO 97/19074 A1 | 5/1997 |
| WO | WO 97/22604 A1 | 6/1997 |
| WO | WO 98/11073 A1 | 3/1998 |
| WO | WO 99/26927 A | 6/1999 |
| WO | WO 01/23399 A1 | 4/2001 |
| WO | WO 01/90090 A1 | 11/2001 |
| WO | WO 03/065983 A2 | 8/2003 |
| WO | WO 03/104207 A2 | 12/2003 |
| WO | 2004/056745 A2 | 7/2004 |
| WO | WO 2004/056744 | 7/2004 |
| WO | WO 2004/065351 A1 | 8/2004 |
| WO | WO 2004/089415 | 10/2004 |
| WO | WO 2004/089416 | 10/2004 |
| WO | WO 2004/089470 | 10/2004 |
| WO | WO 2004/075847 A2 | 9/2007 |

OTHER PUBLICATIONS

Chemical Abstract: Database CHEMCATS (Apr. 23, 2003) Database accession No. 2001:711911.
Chemical Abstract: Database CHEMCATS (Aug. 11, 2003) Database accession No. 2001:1353682.
Chemical Abstract: Database CHEMCATS (Apr. 25, 2003) Database accession No. 2001:2280339.
Chemical Abstract: Database CHEMCATS (Oct. 20, 2003) Database accession No. 2002:1350205.
Chemical Abstract: Database CHEMCATS (Oct. 20, 2003) Database accession No. 2002:1350218.
Sabri S. S. et al: "Syntheses and Antibacterial Activity of some New N-(3-Methyl-2-quinoxalyl) Amino Alcohols and Amine 1,4-Dioxides" Journal of Chemical and Engineering Data, Americn Chemical Society, US, vol. 29, No. 2, 1984, pp. 229-231.
Avdyunina, N. I. et al: "N-Adamantylamides of benzimidazoline-3-acetic acids: synthesis and pharmacological properties" KHIMIKO-FARMATSEVTICHESKII ZHURNAL, 22(7), 819-22, 1988.
PCT International Search Report dated Dec. 9, 2005 for PCT Application. No. PCT/EP2005/054197 which relates to U.S. Patent Application filed herewith.
Written Opinion of the International Searching Authority for PCT Application No. PCT/EP2005/054197, 2005.
Masuzaki H. et al., "A Transgenic Model of Visceral Obesity and the Metabolic Syndrome.", Science, 2001, pp. 2166-2170, vol. 294.
Montague et al., "Perspective in Diabetes. The Perils of Portliness. Causes and Consequences of Visceral Adiposity.", Diabetes, 2000, pp. 883-888, vol. 49.
Rauz et al., "Expression and Putative Role of 11β-Hydroxysteroid Dehydrogenase Isozymes within the Human Eye.", Invest. Ophtalmol. Vis. Science, Aug. 2001, pp. 2037-2042, vol. 42(9).
Sabri et al., "Synthesis and Antibacterial Activity of Some New N-(3-Methyl-2-quinoxaloyl) Amino Alcohols and Amine 1,4-Dioxides.", J. Chem. Eng. Data, 1984, pp. 229-231, vol. 29(2).
Stewart et al., "Cortisol, 11β-hydroxysteroid dehydrogenase type 1 and central obesity.", Trends. Endrocrin. Metabol., 2002, pp. 94-96, vol. 13.
Zhou et al., "Glucocorticoid effects on extracellular matrix proteins and integrins in bovine trabecular meshwork cells in relation to glaucoma.", Int. J. Mol. Med., 1998, pp. 339-346, vol. 1.
Markownikow, "Beilstein Institut zur Foerderung der Chemischen Wissenschaften, Frankfurt am Main, DE". Chem. Ber., 1892, p. 3357, vol. 25, XP-002248050.
Mizuno, K., "Beilstein Institut zur Foerderung der Chemischen Wissenschaften Frankfurt am Main, DE". J. Chem. Soc. Chem. Commun., 1975, p. 308, XP-002248042.
Murahashi, S., "Synthesis of Phthalimidines from Schiff Bases and Carbon Monoxide" J. Am. Chem. Soc., vol. 77, 1955, pp. 6403-6404, XP-002358750.
Nikiforov et al., "Synthesis and Absolute Configuration of Diastereomeric 3-Substituted 1-[1'(S)-Phenylethyl]-2-Pyrrolidinones.", Doklady Bolgarskoi Akademii Nauk, 1986, pp. 73-76, vol. 39(3).
Oda et al., "An efficient route to chiral, non-racemic 3-alkyl-3-arylpyrrolidines. Improved stereoselectivity in alkylation of bicyclic lactams and the effect of leaving groups.", Tetrahedron Letters, 2000, pp. 8193-8197, vol. 41(43).
Olah et al., "Beilstein Institut zur Foerderung der Chemischen Wissenschaften Frankfurt am Main, DE". Synthesis, 1979, p. 274-726, XP002248039.
Olsen, C. E., "Beilstein Institut zur Foerderung der Chemischen Wissenschaften Frankfurt am Main, DE". Acta Chem. Scand. Ser. B., 1975, pp. 953-62, XP002248044.
Pharmas-Cutting-Edge; http://pharmaweblog.com/blog/category/rd/preclinical (1 page), 2007.
Pop et al., "Versatile Acylation of N-Nucleophiles Using a New Polymer-Supported 1-Hydroxybenzotriazole Derivative.", J. Org. Chem., 1997, pp. 2594-2603, vol. 62.
Rufer et al: "Neue Acylierte 2-(4-Aminiophenyl)-Propionsaeuren ALS Potentiele Antiplogistica" European Journal of Medicinal Chemistry, Editions Scientifique Elsevier, Paris, FR, Mar. 1978, pp. 193-198, vol. 13(2), XP001068547.
Schroth, W. et al., "Beilstein Institut zur Foerderung der Chemischen Wissenschaften Frankfurt am Main, DE". J. Prakt. Chem., 1983, pp. 787-802, vol. 325, No. 5, XP002248035.
Starnes, S. et al., "Beilstein Institut zur Foerderung der Chemischen Wissenschaften Frankfurt am Main, DE". J. Amer. Chem. Soc., 2001, pp. 4659-4669, vol. 123(20), XP002248037.
Sugasawa, O. et al., "Beilstein Institut zur Foerderung der Chemischen Wissenschaften Frankfurt am Main, DE". 1952, p. 7461, vol. 72, XP002248038.
Takahashi, T., "Synthesis of analgesics. XX. Camphane derivatives. 2'retrieved from STN". Chem. Abst. 1959, pp. 162-166, vol. 79, XP002248033.
Terauchi, J. et al., "Beilstein Institut zur Foerderung der Chemischen Wissenschaften Frankfurt am Main, DE". Tetrahedron, 2003, pp. 587-592, vol. 14(5), XP002279295.
Treatment of Dementia: Anything New ?; http://www.medscape.com/viewarticle/547499_print (8 pages), 2006.
Wamil et al., "Inhibition of 11β-hydroxysteriod dehydrogenase type 1 as a promising therapeutic target.", Drug Discovery Today, Jul. 2007, pp. 504-520, vol. 12 (13/14), Elsevier.

Yamato, M. et al., "Beilstein Institut zur Foerderung der Chemischen Wissenschaften Frankfurt am Main, DE". *Chem. Pharm. Bull.*, 1988, pp. 3453-3461, vol. 36(9), XP002279297.

Yau et al., "Targeting 11β-hydroxysteroid dehydrogenase type 1 in brain: therapy for cognitive aging?", *Expert Review of Endrocrinology & Metabolism*, 2006, pp. 527-536, vol. 1(4), Future Drugs Ltd.

Young, C., "Beilstein Institut zur Foerderung der Chemischen Wissenschaften, Frankfurt am Main, DE". *J. Chem. Soc.*, 1898, p. 365, vol. 73, XP-002248041.

"Incyte's Selective Oral Inhibitor of 11beta-HSD1 Demonstrates Improvements in Insuling Sensivity and Lowers Cholesterol levels in Type 2 Diabetics." About Incyte: Press Release, Incyte Corporation website, http://investor.incyte.com, Jun. 9, 2008.

Aicher et al., "Kappa Opioid Receptor (KOR) and GAD67 Immunoreactivity Are Found in Off and Neutral Cells in the Rostral Ventromedial Medulla.", *J. Neurophysiol*, 2006, vol. 96, pp. 3465-3473, Caplus an 2006:440111.

Amgen-Investors-Pipeline; http://www.amgen.com/investors/pipe_AMG221.html (1 page), 2008.

Apria-Resources-news; http://www.apria.com/resources/1,2725,494-769212,00.html (4 pages), 2008.

Arzel P. et al., *Assymetrie Tetrahedron*, 1999, pp. 3877-3881, vol. 10(20), XP001203518.

Badman et al., "The Gut and Energy Balance, Visceral Allies in the Obesity Wars.", *Science*, Mar. 25, 2005, pp. 1909-1014, vol. 307.

Bausanne et al. (Tetrahedron: Assymetry (1998), 9(5), 797-804) Baussane et al., "Asymmetric synthesis of 3-substituted pyrrolidones via α-alkylation of a chiral non-racemic γ-lactam." *Tetrahedron: Assymetry*, 1998, pp. 797-804, vol. 9(5).

Blommaert et al., "Mono and Sequential BIS Solid Phase Alkylations of a (R)-Phenylglycinol Derived Pyrrolidinone Scaffold.", *Heterocycles*, 2001, pp. 2273-2278, vol. 55(12).

Bonnekessel, J., et al., "Beilstein Institut zur Foerderung der Chemischen Wissenschaften Frankfurt am Main, DE". *Chem. Ber.* 1973, pp. 2890-2903, vol. 106, XP002248049.

Boyle, Craig D., "Recent advances in the discovery of 11β-HSD1 inhibitors.", *Current Opinion in Drug Discovery & Development*, 2008, pp. 495-511, vol. 11(4), The Thompson Corporation.

Caglioti, L., et al., Beilstein Institut zur Foerderung der Chemischen Wissenschaften Frankfurt am Main, DE *J. Org. Chem.*, 1968, pp. 2979-2981 vol. 33(7), XP002248043.

Camps, Beilstein Institut zur Foerderung der Chemischen Wissenschaften, Frankfurt am Main, DE., *Arch. Pharm.*; 1902, p. 358, vol. 240, XP002248047.

Chapman et al., "11β-HSD1, Inflammation, Metabolic Disease and Age-related Cognitive (dys)Function.", *Neurochemical Research*, 2008, vol. 33, pp. 624-636, Springer Science + Business.

Chemical Abstract: Database Beilstein, Database accession No. 1481016, and 1481024, Amano, 1966, XP-002258756.

Chemical Abstract: Database Beilstein, Database accession No. 5949999, Schmitz, E. et al (1982), XP-002358755.

Chemical Abstract: Database Caplus, Database accession No. 1966:71362 Amano, T. 1966, XP-002358757.

Division of Medical Chemistry Abstracts—234th ACS National Meeting Boston, MA, Aug. 19-23, 2007.

Forster, A., "Beilstein Institut zur Foerderung der Chemischen Wissenschaften Frankfurt am Main, DE". *J. Chem. Soc.*, 1904, pp. 1190, vol. 85, XP-002248034.

Garcia-Valverde et al., "A Diastereoselective Approach to Enantiopure 3-Substituted Pyrrolidines from Masked Lithium Homoenolates Derived from Norephedrine.", *Tetrahedron*, 1996, pp. 10761-10770, vol. 52(32).

Giuliano, L., "Beilstein Institut zur Foerderung der Chemischen Wissenschaften Frankfurt am Main, DE" Farmaco, 1952, pp. 29-32, vol. 7, XP002248051.

Gryszkiewicz-Trochimowski, "Beilstein Institut zur Foerderung der Chemischen Wissenschaften Frankfurt am Main, DE"., *Rocz. Chem*, 1934, pp. 335-337, vol. 14, XP002248048.

Huges et al., "11-Beta-hydroxysteroid dehydrogenase type 1 (11β-HSD1) inhibitors in Type 2 diabetes mellitus and obesity.", *Expert Opinion, Investig. Drugs*, 2008, pp. 481-496, vol. 17(4), Informa Healthcare, UK.

Jones, et al., "Beilstein Institut zur Foerderung der Chemischen Wissenschaften Frankfurt am Main, DE". *Tetrahedron*, 1965, pp. 2961-2966, vol. 21, XP002279296.

Katritzky, A. et al "Novel syntheses of enantiopure hexahydroimidazo[1,5-*b*]-isoquinolines and tetrahydroimidazo[1,5-*b*]-isoquinolin-1(5H)-ones via iminium cation cyclizations" *J. Org. Chem.*, 2002, pp. 8224-8229, vol. 67, XP-002358751.

Kitagawa, O. et al., "Beilstein Institut zur Foerderung der Chemischen Wissenschaften Frankfurt am Main, DE". *Tetrahedron Lett.*, 1999, pp. 8827-8832, vol. 40(50), XP002279294.

Knunjanz, G. "Beilstein Institut zur Foerderung der Chemischen Wissenschaften Frankfurt am Main, DE". IASKA6, 1958, pp. 1219-1221, XP002248040.

Koenig, H. et al., "Beilstein Institut zur Foerderung der Chemischen Wissenschaften Frankfurt am Main, DE". *Chem. Ber.*, 1965, pp. 3712-3723, vol. 98, XP002248046.

Koetz, M., "Beilstein Institut zur Foerderung der Chemischen Wissenschaften Frankfurt am Main, DE". *J. Prakt. Chem.*; 1926, pp. 74, vol. 113, XP-002248036.

Kuehne, M. E., et al., "Beilstein Institut zur Foerderung der Chemischen Wissenschaften Frankfurt am Main, DE". *J. Org. Chem.*, 1977, pp. 2082-2087, vol. 42(12), XP002248045.

Larsen et al., "A Modified Bischler-Napieralski Procedure for the Synthesis of 3-Aryl-3,4-dihydroisoguinolines.", *Journal of Organic Chemistry*, 1991, pp. 6034-6038, vol. 56(21), American.Chemical Society.

Latypov et al., "Determination of the absolute stereochemistry of alcohols and amines by NMR of the group directly linked to the chiral derivatizing reagent". *Tetrahedron*, 2001, pp. 2231-2236, vol. 57(11), XP004230761.

Lavrova et al., *Zhurnal Organicheskoi Khimii* (1974), pp. 761-7655, vol. 10(4).

* cited by examiner

N-2 ADAMANTANYL-2-PHENOXY-ACETAMIDE DERIVATIVES AS 11-BETA HYDROXYSTEROID DEHYDROGENASE INHIBITORS

CROSS REFERENCE TO RELATED APPLICATIONS

This application is the U.S. national stage of Application No. PCT/EP2005/054197, filed Aug. 26, 2005, which application claims priority from EP 04104152.6, filed Aug. 30, 2004 and U.S. Application No. 60/607,851, filed Sep. 8, 2004.

The metabolic syndrome is a disease with increasing prevalence not only in the Western world but also in Asia and developing countries. It is characterized by obesity in particular central or visceral obesity, type 2 diabetes, hyperlipidemia, hypertension, arteriosclerosis, coronary heart diseases and eventually chronic renal failure (C. T. Montague et al. (2000), Diabetes, 49, 883-888).

Glucocorticoids and 11β-HSD1 are known to be important factors in differentiation of adipose stromal cells into mature adipocytes. In the visceral stromal cells of obese patients, 11β-HSD1 mRNA level is increased compared with subcutaneous tissue. Further, adipose tissue over-expression of 11β-HSD1 in transgenic mice is associated with increased corticoserone levels in the adipose tissue, visceral obesity, insulin sensitivity, Type 2 diabetes, hyperlipidemia and hyperphagia (H. Masuzaki et al (2001), Science, 294, 2166-2170). Therefore, 11β-HSD1 is most likely be involved in the development of visceral obesity and the metabolic syndrome.

Inhibition of 11β-HSD1 results in a decrease in differentiation and an increase in proliferation of adipose stromal cells. Moreover, glucocorticoid deficiency (adrenalectomy) enhances the ability of insulin and leptin to promote anorexia and weight loss, and this effect is reversed by glucocorticoid administration (P. M. Stewart et al (2002), Trends Endocrin. Metabol, 13, 94-96). These data suggest that enhanced reactivation of corticone by 11β-HSD1 may exacerbate obesity and it may be beneficial to inhibit this enzyme in adipose tissue of obese patients.

Obesity is also linked to cardiovascular risks. There is a significant relationship between cortisol excretion rate and HDL cholesterol in both men and women, suggesting that glucocorticoids regulate key components of cardiovascular risk. In analogy, aortic stiffness is also associated with visceral adiposity in older adults.

The impact of the effect of decreased 11β-HSD1 activity is highlighted by the β-HSD1 knockout mouse that has increased plasma levels of endogenous active glucocorticoid, but inspite of this remains protected from insulin resistance induced by stress and obesity. Additionally, these knockout mouse present an anti-atherogenic plasmid lipid profile and benefits from decreased age-related cognitive impairement.

Glucocorticoids and Glaucoma

Glucocorticoids increase the risk of glaucoma by raising the intraocular pressure when administered exogenously and in certain conditions of increased production like in Cushing's syndrome. Corticosteroid-induced elevation of intra ocular pressure is caused by increased resistance to aqueous outflow due to glucocorticoid induced changes in the trabecular meshwork and its intracellular matrix. Zhou et al. (Int J Mol Med (1998) 1, 339-346) also reported that corticosteroids increase the amounts of fibronectin as well as collagen type I and type IV in the trabecular meshwork of organ-cultured bovine anterior segments.

11β-HSD1 is expressed in the basal cells of the corneal epithelium and the non-pigmented epithelial cells. Glucocorticoid receptor mRNA was only detected in the trabecular meshwork, whereas in the non-pigmented epithelial cells mRNA for the glucocorticoid-, mineralocorticoid receptor and 11β-HSD1 was present. Carbenoxolone administration to patients resulted in a significant decrease in intra-ocular pressure (S. Rauz et al. (2001), Invest. Ophtalmol. Vis. Science, 42, 2037-2042), suggesting a role for HSD1-inhibitors in treating glaucoma.

Accordingly, the underlying problem to be solved by the present invention was to identify potent 11β-HSD inhibitors, with a high selectivity for 11β-HSD1, and the use thereof in treating pathologies associated with excess cortisol formation, i.e. disorders where a decreased level of active glucocorticoid is desirable, such as metabolic syndrome, type 2 diabetes, impaired glucose tolerance (IGT), impairing fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. As shown hereinbelow, the 2-adamantanylacetamides of formula (I) were found to be useful as a medicine, in particular in the manufacture of a medicament for the treatment of pathologies associated with excess cortisol formation.

Salim S. S. et al (J.Chem.Eng. Data (1984), 29, 229-231) provides the synthesis of some new N-(3-methyl-2-quinoxaloyl) amino alcohols and in particular discloses 2-Quinoxalinecarboxamide, 3-methyl-N-tricyclo[3.3.1.1$^{3,7}$]dec-2-yl-.. The 1,4-dioxides of said quinoxalines were shown to have antibacterial activity, where the parent quinoxalines were inactive as antibacterial agents.

Masamune H. et al. (PCT International patent application WO 01/23399) discloses N-2-adamantyl-2-phenoxy-acetamides as intermediates in the preparation of nucleosides as adenosine receptors, antidiabetics, enzyme inhibitors and for the treatment of ischemia. See in particular scheme IV, p41, and the examples 70, 73, B32 and B35.

However, in none of the above-cited documents the therapeutic application of the N-2-adamantyl-acetamide derivatives of the present invention has been disclosed.

The use of adamantyl acetamides as 11-β hydroxysteroid dehydrogenase inhibitors was disclosed in Linders J. et al (PCT International patent application WO 2004/056745). Compared to the compounds disclosed in said publication, the compounds of the present invention differ in that they comprise an additional heteroatom, represented as—Z- in formula (I) below. The presence of this additional heteroatom, together with the particular backbone configuration (represented in bold hereinbelow), significantly improved the overal activity of the adamantly acetamides as 11-β hydroxysteroid dehydrogenase inhibitors (FIG. 1).

FIG. 1 provides a comparison of the cellular 3T3-L1 activity (pIC50 values—see example C hereinbelow) of the bicyclic adamantyl acetamides disclosed in PCT International patent application WO 2004/056745 with the bicyclic ethers of the present application and the single ethers of the present application.

The pharmaceutical use of substituted amides for modulating the activity of 11β-HSD1 either alone or in combination with a glucocorticoid receptor agonist or an antihypertensive agent has been disclosed in PCT International patent applications WO2004/089470, WO 2004/089415 and WO 2004/089416. In said patent publications only one compound, i.e N-adamantan-2-yl-2-o-tolyloxy-acetamide, within the scope of the present application has been disclosed and is accordingly disclaimed from the first and further medical use claims in the present application. Further compounds within the scope of the present application, but previously not described for use as a medicine are;

Cas Number CA Index Name

[721907-95-5] Acetamide, N-tricyclo[3.3.1.1$^{3,7}$]dec-2-yl-2-[3-(trifluoromethyl)phenoxy]-(9CI)
[701966-64-5] Acetamide, 2-[4-(1-methylpropyl)phenoxy]-N-tricyclo[3.3.1.1$^{3,7}$]dec-2-yl-(9CI)
[693829-07-1] Butanamide, 2-phenoxy-N-tricyclo[3.3.1.1$^{3,7}$]dec-2-yl-(9CI)
[693264-73-2] Acetamide, 2-(2-bromo-4-ethylphenoxy)-N-tricyclo[3.3.1.1$^{3,7}$]dec-2-yl-(9CI)
[690979-00-1] Acetamide, N-tricyclo[3.3.1.1$^{3,7}$]dec-2-yl-2-(2,3,5-trimethylphenoxy)-(9CI)
[667874-33-1] Acetamide, 2-(2,3-dimethylphenoxy)-N-tricyclo[3.3.1.1$^{3,7}$]dec-2-yl-(9CI)
[638150-96-6] Acetamide, 2-(2,4-dibromo-6-methylphenoxy)-N-tricyclo[03.3.1.1$^{3,7}$]dec-2-yl-(9CI)
[638150-94-4] Acetamide, 2-(4-chloro-2-methylphenoxy)-N-tricyclo[3.3.1.1$^{3,7}$]dec-2-yl-(9CI)
[638150-55-6] Acetamide, 2-(3,5-dimethylphenoxy)-N-tricyclo[3.3.1.1$^{3,7}$]dec-2-yl-(9CI)
[638150-85-3] Acetamide, 2-(2-chlorophenoxy)-N-tricyclo[3.3.1.1$^{3,7}$]dec-2-yl-(9CI)
[638150-82-0] Acetamide, 2-[4-(1,1-dimethylethyl)phenoxy]-N-tricyclo[3.3.1.1$^{3,7}$]dec-2-yl-(9CI)
[638150-79-5] Acetamide, 2-[(4-chlorophenyl)thio]-N-tricyclo[3.3.1.1$^{3,7}$]dec-2-yl-(9CI)
[593240-71-2] Acetamide, 2-[5-methyl-2-(1-methylethyl) phenoxy]-N-tricyclo[3.3.1.1$^{3,7}$]dec-2-yl-(9CI)
[593240-69-8] Acetamide, 2-(4-ethylphenoxy)-N-tricyclo[3.3.1.1$^{3,7}$]dec-2-yl-(9CI)
[496921-25-6] Acetamide, 2-(2,5-dimethylphenoxy)-N-tricyclo[3.3.1.1$^{3,7}$]dec-2-yl-(9CI)
[461446-43-5] Acetamide, 2-(3,4-dimethylphenoxy)-N-tricyclo[3.3.1.1$^{3,7}$]dec-2-yl-(9CI)
[438477-86-2] Acetamide, 2-(2,4-dimethylphenoxy)-N-tricyclo[3.3.1.1$^{3,7}$]dec-2-yl-(9CI)
[433948-36-8] Acetamide, 2-(4-bromo-2-methylphenoxy)-N-tricyclo[3.3.1.1$^{3,7}$]dec-2-yl-(9CI)
[433947-37-6] Acetamide, 2-(4-bromo-3,5-dimethylphenoxy)-N-tricyclo[3.3.1.1$^{3,7}$]dec-2-yl-(9CI)
[432539-68-9] Acetamide, 2-[4-(1-methylethyl)phenoxy]-N-tricyclo[3.3.1.1$^{3,7}$]dec-2-yl-(9CI)
[430462-84-3] Acetamide, 2-(4-bromo-2-chlorophenoxy)-N-tricyclo[3.3.1.1$^{3,7}$]dec-2-yl-(9CI)
[429631-57-2] Acetamide, 2-(4-chloro-3-methylphenoxy)-N-tricyclo[3.3.1.1$^{3,7}$]dec-2-yl-(9CI)
[429626-19-7] Acetamide, 2-(4-methoxyphenoxy)-N-tricyclo[3.3.1.1$^{3,7}$]dec-2-yl-(9CI)
[426250-14-8] Propanamide, 2-(2,4-dichlorophenoxy)-N-tricyclo[3.3.1.1$^{3,7}$]dec-2-yl-(9CI)
[424814-81-3] Acetamide, 2-(2-bromo-4-methylphenoxy)-N-tricyclo[3.3.1.1$^{3,7}$]dec-2-yl-(9CI)
[424814-50-6] Acetamide, 2-(4-chloro-3,5-dimethylphenoxy)-N-tricyclo[3.3.1.1$^{3,7}$]dec-2-yl-(9CI)
[424814-18-6] Acetamide, 2-(4-bromo-3-methylphenoxy)-N-tricyclo[3.3.1.1$^{3,7}$]dec-2-yl-(9CI)
[405076-76-8] Acetamide, 2-(2,4-dichlorophenoxy)-N-tricyclo[3.3.1.1$^{3,7}$]dec-2-yl-(9CI)
[405076-63-3] Acetamide, 2-phenoxy-N-tricyclo[3.3.1.1$^{3,7}$]dec-2-yl-(9CI)
[339060-39-8] Acetamide, 2-(4-bromophenoxy)-N-tricyclo[3.3.1.1$^{3,7}$]dec-2-yl-(9CI)
[332399-46-9] Acetamide, 2-(4-methylphenoxy)-N-tricyclo[3.3.1.1$^{3,7}$]dec-2-yl-(9CI)
[305341-04-2] Acetamide, 2-(3-bromophenoxy)-N-tricyclo[3.3.1.1$^{3,7}$]dec-2-yl-(9CI)
[298701-43-6] Acetamide, 2-(4-chlorophenoxy)-N-tricyclo[3.3.1.1$^{3,7}$]dec-2-yl-(9CI)
[351418-76-3] Acetamide, 2-(3-methylphenoxy)-N-tricyclo[3.3.1.1$^{3,7}$]dec-2-yl-(9CI)

Accordingly, in a first aspect this invention concerns compounds of formula (I)

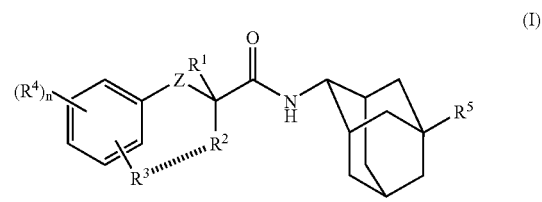

the N-oxide forms, the pharmaceutically acceptable addition salts and the stereochemically isomeric forms thereof, wherein n is 1, 2, 3, or 4;

Z represents O, S, NR$^6$, SO or SO$_2$;

R$^1$ represents hydrogen, cyano, hydroxy, or C$_{1-4}$alkyl optionally substituted with halo, R$^2$ represents hydrogen, C$_{1-4}$alkyl, or C$_{1-4}$alkyloxy-;

R$^3$ represents hydrogen, C$_{1-4}$alkyl, C$_{1-4}$alkyloxy- or R$^3$ combined with R$^2$ form together a divalent radical selected from the group consisting of —O—CH$_2$— (a), —NR$^7$—CH$_2$— (b), —(CR$^8$R$^9$)$_m$- (c) and —CR$^{10}$= (d) wherein m represents 1 or 2 and R$^7$, R$^8$, R$^9$ and R$^{10}$ are each independently selected from hydrogen or C$_{1-4}$alkyl;

R$^4$ represents hydrogen, halo, hydroxy, cyano, amino, NR$^{11}$R$^{12}$, C$_{1-4}$alkyloxycarbonyl, hydroxycarbonyl, C$_{1-4}$alkyloxy- optionally substituted with one or where possible two or three substituents selected from hydroxy and halo or R$^4$ represents C$_{1-4}$alkyl optionally substituted with one or where possible two or three substituents selected from hydroxy and halo;

R$^5$ represents hydrogen, halo, cyano, amino, phenyl, hydroxy, C$_{1-4}$alkyloxycarbonyl, hydroxycarbonyl-, Het$^1$, —NR$^{13}$R$^{14}$, —O—(C=O)—NR$^{21}$R$^{22}$, —O—(C=O)—C$_{1-4}$alkyl, carbonyl-NR$^{23}$R$^{24}$ or C$_{1-4}$alkyl substituted with one or more substituents selected from hydroxy, halo, hydroxycarbonyl, phenyl, C$_{1-4}$alkyloxy or NR$^{15}$R$^{16}$ or R$^5$ represents C$_{1-4}$alkyloxy optionally substituted with one or more substituents selected from hydroxy, halo, hydroxycarbonyl, phenyl, C$_{1-4}$alkyloxy or NR$^{17}$R$^{18}$, or R$^5$ represents —O—(C=O)—C$_{1-4}$alkyl substituted with one or more amino, hydroxy, Het$^3$ or halo substituents;

R$^6$ represents hydrogen or C$_{1-6}$alkyl;

R$^{11}$ and R$^{12}$ each independently represent hydrogen, C$_{1-4}$alkyl, C$_{1-4}$alkylcarbonyl- or C$_{1-4}$-alkylcarbonyl-;

R$^{13}$ and R$^{14}$ each independently represent hydrogen, C$_{1-4}$alkyl, C$_{1-6}$alkyl-SO$_2$—, mono- or di(C$_{1-4}$alkyl) amino-SO$_2$—, Ar$^1$—SO$_2$, mono- or di(C$_{1-4}$alkyl) amino-carbonyl-, C$_{1-4}$alkyl-oxycarbonyl or C$_{1-4}$alkyl-carbonyl- wherein said C$_{1-6}$alkyl-SO$_2$—, C$_{1-4}$alkyl-oxycarbonyl or C$_{1-4}$alkylcarbonyl- are each independently and optionally substituted with one, two or three substituents selected from halo, C$_{1-4}$-alkyloxycarbonyl, NR$^{19}$R$^{20}$ and Het$^2$;

$R^{15}$ and $R^{16}$ each independently represent hydrogen, $C_{1-4}$alkyl, $C_{1-4}$alkyloxycarbonyl- or $C_{1-4}$alkylcarbonyl-;

$R^{17}$ and $R^{18}$ each independently represent hydrogen, $C_{1-4}$alkyl, $C_{1-4}$alkyloxycarbonyl- or $C_{1-4}$alkylcarbonyl-;

$R^{19}$ and $R^{20}$ each independently represent hydrogen, $C_{1-4}$alkylcarbonyl, $C_{1-4}$alkyloxycarbonyl- or $C_{1-4}$alkyl optionally substituted with one or more substituents selected from halo or hydroxy;

$R^{21}$ and $R^{22}$ each independently represent hydrogen, $Ar^2$ or $C_{1-4}$alkyl optionally substituted with one or more substituents selected from halo or hydroxy;

$R^{23}$ and $R^{24}$ each independently represent hydrogen, $C_{1-4}$alkylcarbonyl, $Het^4$ or $C_{1-4}$alkyl optionally substituted with one or more substituents selected from halo or hydroxy;

$Het^1$ represents pyrrolinyl, pyrrolidinyl, pyrrolyl, oxazolyl, isoxazolyl or a radical of formula

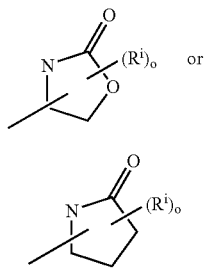

wherein $R^i$ represents hydrogen or $C_{1-4}$alkyl and o is 1 or 2;

$Het^2$ represents morpholinyl, piperidinyl, piperazinyl, thiomorpholinyl or pyrrolidinyl;

$Het^3$ represents morpholinyl, piperidinyl, piperazinyl, thiomorpholinyl or pyrrolidinyl;

$Het^4$ represents piperidinyl, morpholinyl, piperazinyl, thiomorpholinyl or pyrrolidinyl;

$Ar^1$ represents phenyl optionally substituted with $C_{1-4}$alkyl; and $Ar^2$ represents phenyl optionally substituted with $C_{1-4}$alkyl, for use as a medicine, provided however that said compound of formula (I) is other than N-adamantyl-2-yl-2-ortho-tolyloxy-acetamide.

In a further aspect the present invention provides the use of the aforementioned compounds in the manufacture of a medicament for treating pathologies associated with excess cortisol formation such as for example, obesity, diabetes, obesity related cardiovascular diseases, dementia, cognition, osteoporosis and glaucoma.

It is also an object of the present invention to provide compounds of formula (I) the N-oxide forms, the pharmaceutically acceptable addition salts and the stereochemically isomeric forms thereof, wherein $R^1$, $R^2$, $R^3$, $R^4$, $R^{13}$, $R^{14}$, $R^{15}$, $R^{16}$, $R^{17}$, $R^{18}$, Z and n are defined as hereinbefore and wherein $R^5$ represents represents halo, cyano, amino, phenyl, hydroxyl, $C_{1-4}$alkoxycarbonyl-, hydroxycarbonyl, $NR^{13}R^{14}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$, in particular $R^5$ represents halo, cyano, amino, phenyl, hydroxy, $C_{1-4}$alkyloxycarbonyl-, hydroxycarbonyl, $NR^{13}R^{14}$ or $C_{1-4}$alkyl substituted with one or more substituents selected from hydroxycarbonyl, phenyl, $C_{1-4}$alkyloxy or $NR^{15}R^{16}$.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl- 1-methylethyl, 2-methylpropyl, 2,2-dimethylethyl and the like; $C_{1-6}$alkyl defines straight and branched chain saturated hydrocarbon radicals having from 1 to 6 carbon atoms such as the groups defined for $C_{(1-4)}$alkyl and pentyl, hexyl, 2-methylbutyl and the like; $C_{1-4}$alkyloxy defines straight or branched saturated hydrocarbon radicals having form 1 to 4 carbon atoms such as methoxy, ethoxy, propyloxy, butyloxy, 1-methylethyloxy, 2-methylpropyloxy and the like.

The pharmaceutically acceptable addition salts as mentioned hereinabove are meant to comprise the therapeutically active non-toxic acid addition salt forms, which the compounds of formula (I), are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I), are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I), as well as the salts thereof, are able to form. Such solvates are for example hydrates, alcoholates and the like.

The term stereochemically isomeric forms as used hereinbefore defines the possible different isomeric as well as conformational forms which the compounds of formula (I), may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other are intended to be embraced within the scope of the present invention.

The N-oxide forms of the compounds of formula (I), are meant to comprise those compounds of formula (I) wherein one or several nitrogen atoms are oxidized to the so-called N-oxide.

A particular group of compounds are those compounds of formula (I) wherein one or more of the following restrictions apply;

(i) n is 1, 2, 3, or 4;

(ii) Z represents O, S, $NR^6$, SO or $SO_2$;

(iii) $R^1$ represents hydrogen, cyano, hydroxy, or $C_{1-4}$alkyl optionally substituted with halo,
(iv) $R^2$ represents hydrogen, $C_{1-4}$alkyl, or $C_{1-4}$alkyloxy-;
(v) $R^3$ represents hydrogen, $C_{1-4}$alkyl, $C_{1-4}$alkyloxy- or $R^3$ combined with $R^2$ form together a divalent radical selected from the group consisting of —O—CH$_2$— (a), —NR$^7$—CH$_2$— (b), —(CR$^8$R$^9$)$_m$- (c) and —CR$^{10}$= (d) wherein m represents 1 or 2 and $R^7$, $R^8$, $R^9$ and $R^{10}$ are each independently selected from hydrogen or $C_{1-4}$alkyl;
(vi) $R^4$ represents hydrogen, halo, hydroxy, cyano, amino, NR$^{11}$R$^{12}$, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;
(vii) $R^5$ represents hydrogen, halo, cyano, amino, phenyl, hydroxy, $C_{1-4}$alkyloxycarbonyl-, hydroxycarbonyl, NR$^{13}$R$^{14}$ or $C_{1-4}$alkyl substituted with one or more substituents selected from hydroxycarbonyl, phenyl, $C_{1-4}$alkyloxy or NR$^{15}$R$^{16}$; in particular $R^5$ represents halo, cyano, amino, phenyl, hydroxy, $C_{1-4}$alkyloxycarbonyl-, hydroxycarbonyl, NR$^{13}$R$^{14}$ or $C_{1-4}$alkyl substituted with one or more substituents selected from hydroxycarbonyl, phenyl, $C_{1-4}$alkyloxy or NR$^{15}$R$^{16}$;
(viii) $R^6$ represents hydrogen;
(ix) $R^{11}$ and $R^{12}$ each independently represent hydrogen, $C_{1-4}$alkyl or $C_{1-4}$alkylcarbonyl-;
(x) $R^{13}$ and $R^{14}$ each independently represent hydrogen, $C_{1-4}$alkyl or $C_{1-4}$alkylcarbonyl-;
(xi) $R^{15}$ and $R^{16}$ each independently represent hydrogen, $C_{1-4}$alkyl or $C_{1-4}$alkylcarbonyl-.

A first group of compounds consists of those compounds of formula (I) wherein one or more of the following restrictions apply:

n is 1, 2, 3, or 4;
Z represents O, S, NR$^6$, SO or SO$_2$;
$R^1$ represents hydrogen, cyano, hydroxy, or $C_{1-4}$alkyl optionally substituted with halo,
$R^2$ represents hydrogen, $C_{1-4}$alkyl, or $C_{1-4}$alkyloxy-;
$R^3$ represents hydrogen, $C_{1-4}$alkyl, $C_{1-4}$alkyloxy- or $R^3$ combined with $R^2$ form together a divalent radical selected from the group consisting of —O—CH$_2$— (a), —NR$^7$—CH$_2$— (b), —(CR$^8$R$^9$)$_m$- (c) and —CR$^{10}$= (d) wherein m represents 1 or 2 and $R^7$, $R^8$, $R^9$ and $R^{10}$ are each independently selected from hydrogen or $C_{1-4}$alkyl;
$R^4$ represents hydrogen, halo, hydroxy, cyano, amino, NR$^{11}$R$^{12}$, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;
$R^5$ represents hydrogen, halo, cyano, amino, phenyl, hydroxy, $C_{1-4}$alkyloxycarbonyl, hydroxycarbonyl, NR$^{13}$R$^{14}$ or $C_{1-4}$alkyl substituted with one or more substituents selected from hydroxycarbonyl, phenyl, $C_{1-4}$alkyloxy or NR$^{15}$R$^{16}$ or $R^5$ represents $C_{1-4}$alkyloxy optionally substituted with one or more substituents selected from hydroxycarbonyl, phenyl, $C_{1-4}$alkyloxy or NR$^{17}$R$^{18}$; in particular $R^5$ represents halo, cyano, amino, phenyl, hydroxy, $C_{1-4}$alkyloxycarbonyl-, hydroxycarbonyl, NR$^{13}$R$^{14}$ or $C_{1-4}$alkyl optionally substituted with one or more substituents selected from hydroxycarbonyl, phenyl, $C_{1-4}$alkyloxy or NR$^{15}$R$^{16}$ or $R^5$ represents $C_{1-4}$alkyloxy optionally substituted with one or more substituents selected from hydroxycarbonyl, phenyl, $C_{1-4}$alkyloxy or NR$^{17}$R$^{18}$ $R^6$ represents hydrogen or $C_{1-4}$alkyl;
$R^{11}$ and $R^{12}$ each independently represent hydrogen, $C_{1-4}$alkyl or $C_{1-4}$alkylcarbonyl-;
$R^{13}$ and $R^{14}$ each independently represent hydrogen, $C_{1-4}$alkyl or $C_{1-4}$alkylcarbonyl-;
$R^{15}$ and $R^{16}$ each independently represent hydrogen, $C_{1-4}$alkyl or $C_{1-4}$alkylcarbonyl-;
$R^{17}$ and $R^{18}$ each independently represent hydrogen, $C_{1-4}$alkyl or $C_{1-4}$alkylcarbonyl-, for use as a medicine, provided however than said compound is other than N-adamantyl-2-yl-2-ortho-tolyloxy-acetamide.

A second group of compounds consists of those compounds of formula (I) wherein one or more of the following restrictions apply:

(i) n is 1, 2, 3, or 4;
(ii) Z represents O, S, NR$^6$, SO or SO$_2$;
(iii) $R^1$ represents hydrogen, cyano, hydroxy, or
(iv) $C_{1-4}$alkyl optionally substituted with halo,
(v) $R^2$ represents hydrogen, $C_{1-4}$alkyl, or $C_{1-4}$alkyloxy-;
(vi) $R^3$ represents hydrogen, $C_{1-4}$alkyl, $C_{1-4}$alkyloxy- or $R^3$ combined with $R^2$ form together a divalent radical selected from the group consisting of —O—CH$_2$— (a), —NR$^7$—CH$_2$— (b), —(CR$^8$R$^9$)$_m$- (c) and —CR$^{10}$= (d) wherein m represents 1 or 2 and $R^7$, $R^8$, $R^9$ and $R^{10}$ are each independently selected from hydrogen or $C_{1-4}$alkyl;
(vii) $R^4$ represents hydrogen, halo, hydroxy, cyano, amino, NR$^{11}$R$^{12}$, $C_{1-4}$alkyloxycarbonyl, hydroxycarbonyl, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;
(viii) $R^5$ represents halo, cyano, amino, phenyl, hydroxy, $C_{1-4}$alkyloxycarbonyl-, hydroxycarbonyl-, Het$^1$, —NR$^{13}$R$^{14}$, —O—(C=O)—NR$^{21}$R$^{22}$, —O—(C=O)—$C_{1-4}$alkyl, carbonyl-NR$^{23}$R$^{24}$ or $C_{1-4}$alkyl optionally substituted with one or more substituents selected from hydroxycarbonyl, phenyl, $C_{1-4}$alkyloxy or NR$^{15}$R$^{16}$ or $R^5$ represents $C_{1-4}$alkyloxy optionally substituted with one or more substituents selected from hydroxycarbonyl, phenyl, $C_{1-4}$alkyloxy or NR$^{17}$R$^{18}$, or $R^5$ represents —O—(C=O)—$C_{1-4}$alkyl substituted with one or more Het$^3$ or halo substituents;
(ix) $R^6$ represents hydrogen or $C_{1-4}$alkyl;
(x) $R^{11}$ and $R^{12}$ each independently represent hydrogen, $C_{1-4}$alkyl, $C_{1-4}$alkyloxy- carbonyl or $C_{1-4}$alkylcarbonyl-; in particular hydrogen, $C_{1-4}$alkyl or $C_{1-4}$alkylcarbonyl-;
(xi) $R^{13}$ and $R^{14}$ each independently represent hydrogen, $C_{1-4}$alkyl, $C_{1-6}$alkyl-SO$_2$—, mono- or di($C_{1-4}$alkyl)amino-SO$_2$—, Ar$^1$—SO$_2$, mono- or di($C_{1-4}$alkyl)amino-carbonyl-, $C_{1-4}$alkyl-oxycarbonyl or $C_{1-4}$alkyl-carbonyl- wherein said $C_{1-6}$alkyl-SO$_2$—, $C_{1-4}$alkyloxycarbonyl or $C_{1-4}$alkylcarbonyl- are each independently and optionally substituted with one, two or three substituents selected from halo, $C_{1-4}$alkyloxycarbonyl, NR$^{19}$R$^{20}$ and Het$^2$;
(xii) $R^{15}$ and $R^{16}$ each independently represent hydrogen, $C_{1-4}$alkyl, $C_{1-4}$alkyl- oxycarbonyl or $C_{1-4}$alkylcarbonyl-; in particular hydrogen, $C_{1-4}$alkyl or $C_{1-4}$alkylcarbonyl-;

(xiii) $R^{17}$ and $R^{18}$ each independently represent hydrogen, $C_{1-4}$alkyl, $C_{1-4}$alkyloxy- carbonyl or $C_{1-4}$alkylcarbonyl-; in particular hydrogen, $C_{1-4}$alkyl or $C_{1-4}$alkylcarbonyl-;

(xiv) $R^{19}$ and $R^{20}$ each independently represent hydrogen, $C_{1-4}$alkylcarbonyl or $C_{1-4}$alkyl optionally substituted with one or more substituents selected from halo or hydroxy; in particular optionally substituted with hydroxy;

(xv) $R^{21}$ and $R^{22}$ each independently represent hydrogen, $Ar^2$ or $C_{1-4}$alkyl optionally substituted with one or more substituents selected from halo or hydroxy; in particular optionally substituted with hydroxy;

(xvi) $R^{23}$ and $R^{24}$ each independently represent hydrogen, $C_{1-4}$alkylcarbonyl, $Het^4$ or $C_{1-4}$alkyl optionally substituted with hydroxy;

(xvii) $Het^1$ represents pyrrolinyl, pyrrolidinyl, pyrrolyl, oxazolyl, isoxazolyl or a radical of formula

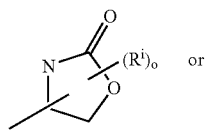
a)

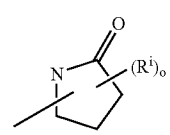
b)

wherein $R^i$ represents hydrogen or $C_{1-4}$alkyl and o is 1 or 2; in particular $Het^1$ represents a radical of formula

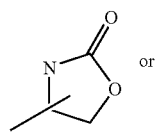
a)

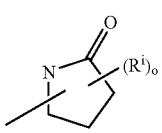
b)

wherein $R^i$ represents hydrogen or $C_{1-4}$alkyl and o is 1 or 2;

(xviii) $Het^2$ represents morpholinyl, piperidinyl, piperazinyl, thiomorpholinyl or pyrrolidinyl; in particular $Het^2$ represents morpholinyl;

(xix) $Het^3$ represents morpholinyl, piperidinyl, piperazinyl, thiomorpholinyl or pyrrolidinyl; in particular $Het^3$ represents morpholinyl;

(xx) $Het^4$ represents piperidinyl, morpholinyl, piperazinyl, thiomorpholinyl or pyrrolidinyl; in particular $Het^4$ represents piperidinyl;

(xxi) $Ar^1$ represents phenyl optionally substituted with $C_{1-4}$alkyl; and (xxii) $Ar^2$ represents phenyl optionally substituted with $C_{1-4}$alkyl.

A third group of compounds consists of those compounds of formula (I) wherein one or more of the following restrictions apply:

(i) n is 1, 2, 3, or 4;
(ii) Z represents O, S, $NR^6$, SO or $SO_2$;
(iii) $R^1$ represents hydrogen, cyano, hydroxy, or $C_{1-4}$alkyl optionally substituted with halo,
(iv) $C_{1-4}$alkyl optionally substituted with halo,
(v) $R^2$ represents hydrogen, $C_{1-4}$alkyl, or $C_{1-4}$alkyloxy-;
(vi) $R^3$ represents hydrogen, $C_{1-4}$alkyl, $C_{1-4}$alkyloxy- or $R^3$ combined with $R^2$ form together a divalent radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;
(vii) $R^4$ represents hydrogen, halo, hydroxy, cyano, amino, $NR^{11}R^{12}$, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;
(viii) $R^5$ represents halo, cyano, amino, phenyl, hydroxy, $C_{1-4}$alkyloxycarbonyl-, hydroxycarbonyl, $NR^{13}R^{14}$ or $C_{1-4}$alkyl substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$;
(ix) $R^6$ represents hydrogen or $C_{1-4}$alkyl;
(x) $R^{11}$ and $R^{12}$ each independently represent hydrogen, $C_{1-4}$alkyl or $C_{1-4}$alkylcarbonyl-;
(xi) $R^{13}$ and $R^{14}$ each independently represent hydrogen, $C_{1-4}$alkyl or $C_{1-4}$alkylcarbonyl-;
(xii) $R^{15}$ and $R^{16}$ each independently represent hydrogen, $C_{1-4}$alkyl or $C_{1-4}$alkylcarbonyl-;
(xiii) $R^{17}$ and $R^{18}$ each independently represent hydrogen, $C_{1-4}$alkyl or $C_{1-4}$alkylcarbonyl-.

A group of interesting compounds consists of those compounds of formula (I) wherein one or more of the following restrictions apply;

(i) n is 1, 2, 3, or 4;
(ii) Z represents O, S, $NR^6$ or $SO_2$; in particular O or $NR^6$;
(iii) $R^1$ represents hydrogen or $C_{1-4}$alkyl;
(iv) $R^2$ represents hydrogen or $C_{1-4}$alkyl;
(v) $R^3$ represents hydrogen, $C_{1-4}$alkyl, $C_{1-4}$alkyloxy- or $R^3$ combined with $R^2$ form together a divalent radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;
(vi) $R^4$ represents hydrogen, halo, hydroxy, amino, —$NR^{11}R^{12}$, $C_{1-4}$alkyloxy-, $C_{1-4}$alkyloxycarbonyl-0, hydroxycarbonyl-, or $C_{1-4}$alkyl optionally substituted with one or where possible two or three halo substituents;
(vii) $R^5$ represents hydrogen, halo, amino, phenyl, hydroxy, hydroxycarbonyl, $Het^1$, $NR^{13}R^{14}$, —O—(C=O)—$C_{1-4}$alkyl, -carbonyl-$NR^{23}R^{24}$ or $R^5$ represents $C_{1-4}$alkyloxy optionally substituted with one or more substituents selected from $NR^{17}R^{18}$ or $R^5$ represents —O(=O)—$C_{1-4}$alkyl substituted with halo or $Het^3$;
(viii) $R^{11}$ and $R^{12}$ each independently represent hydrogen, $C_{1-4}$alkyl or $C_{1-4}$alkylcarbonyl-;
(ix) $R^{13}$ and $R^{14}$ each independently represent hydrogen, $C_{1-4}$alkyl, $C_{1-6}$alkyl-$SO_2$—, mono- or di($C_{1-4}$alkyl) amino-$SO_2$—, $Ar^1$—$SO_2$, mono- or di($C_{1-4}$alkyl) amino-carbonyl-, $C_{1-4}$alkyl-oxycarbonyl or $C_{1-4}$alkylcarbonyl- wherein said $C_{1-6}$alkyl-$SO_2$—, $C_{1-4}$alkyloxycarbonyl or $C_{1-4}$alkylcarbonyl- are each independently and optionally substituted with one, two or three substituents selected from halo, $C_{1-4}$alkyloxycarbonyl, $NR^{19}R^{20}$ and $Het^2$;

(x) $R^{17}$ and $R^{18}$ each independently represent $C_{1-4}$alkyl;

(xi) $R^{19}$ and $R^{20}$ each independently represent hydrogen or $C_{1-4}$alkyl optionally substituted with hydroxy;

(xii) $R^{21}$ and $R^{22}$ each independently represent hydrogen or $Ar^2$;

(xiii) $R^{23}$ and $R^{24}$ each independently represent hydrogen or $Het^4$;

(xiv) $Het^1$ represents a radical of formula

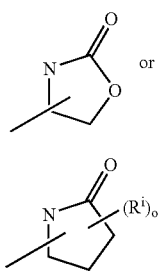

a)

b)

wherein $R^i$ represents hydrogen or $C_{1-4}$alkyl and o is 1 or 2;

(xv) $Het^2$ represents morpholinyl;

(xvi) $Het^3$ represents morpholinyl;

(xvii) $Het^4$ represents piperidinyl;

(xviii) $Ar^1$ and $Ar^2$ each independently represent phenyl optionally substituted with $C_{1-4}$alkyl, for use as a medicine, provided however that said compound of formula (I) is other than N-adamantyl-2-yl-2-ortho-tolyloxy-acetamide.

Another interesting group of compounds consists of those compounds of formula (I) wherein one or more of the following restrictions apply:

(i) n is 1, 2, 3, or 4;
(ii) Z represents O, S or $SO_2$; in particular O;
(iii) $R^1$ represents hydrogen or $C_{1-4}$alkyl;
(iv) $R^2$ represents hydrogen or $C_{1-4}$alkyl;
(v) $R^3$ represents hydrogen, $C_{1-4}$alkyl, $C_{1-4}$alkyloxy- or $R^3$ combined with $R^2$ form together a divalent radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;
(vi) $R^4$ represents hydrogen, hydroxy, amino, —$NR^{11}R^{12}$, $C_{1-4}$alkyloxy- or $C_{1-4}$alkyl optionally substituted with one or where possible two or three halo substituents;
(vii) $R^5$ represents hydrogen or hydroxy; in particular hydroxy;
(viii) $R^{11}$ and $R^{12}$ each independently represent hydrogen, $C_{1-4}$alkyl or $C_{1-4}$alkylcarbonyl-;

Another group of interesting compounds consists of those compounds of formula (I) wherein one or more of the following restrictions apply:

(i) n is 1, 2, 3, or 4;
(ii) $R^1$ represents a hydrogen;
(iii) $R^3$ combined with $R^2$ form together a divalent radical selected from the group consisting of —O—$CH_2$— (a), —$NR^7$—$CH_2$— (b), —$(CR^8R^9)_m$- (c) and —$CR^{10}$=
(d) wherein m represents 1 or 2 and $R^7$, $R^8$, $R^9$ and $R^{10}$ are each independently selected from hydrogen or $C_{1-4}$alkyl;
(iv) $R^4$ represents hydrogen, halo, hydroxy, $C_{1-4}$alkyloxy-, or $C_{1-4}$alkyl; in particular $R^4$ represents methyl, ethyl, methoxy, fluor, chloro or bromo;
(v) $R^5$ represents halo, cyano, amino, phenyl, hydroxy, $C_{1-4}$alkyloxy-carbonyl-, hydroxycarbonyl, $NR^{13}R^{14}$ or $C_{1-4}$-alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$, in particular $R^5$ represents halo, cyano, amino, phenyl, hydroxy, $C_{1-4}$alkyloxycarbonyl-, hydroxycarbonyl, $NR^{13}R^{14}$ or $C_{1-4}$alkyl substituted with one or more substituents selected from hydroxycarbonyl, phenyl, $C_{1-4}$alkyloxy or $NR^{15}R^{16}$; even more particular $R^5$ represents hydrogen or hydroxy; in particular hydroxy;
(vi) $R^{13}$ and $R^{14}$ each independently represent hydrogen, $C_{1-4}$alkyl or $C_{1-4}$alkylcarbonyl-;
(vii) $R^{15}$ and $R^{16}$ each independently represent hydrogen, $C_{1-4}$alkyl or $C_{1-4}$alkylcarbonyl-;
(viii) $R^{17}$ and $R^{18}$ each independently represent hydrogen, $C_{1-4}$alkyl or $C_{1-4}$alkylcarbonyl-.

Another group of interesting compounds consists of those compounds of formula (I) wherein one or more of the following restrictions apply:

(i) n is 1 or 2;
(ii) $R^1$ represents a $C_{1-4}$alkyl, in particular methyl;
(iii) $R^2$ represents a $C_{1-4}$alkyl, in particular methyl;
(iv) $R^3$ represents hydrogen;
(v) $R^4$ represents hydrogen, halo, —$NR^{11}R^{12}$, $C_{1-4}$alkyloxy-, or $C_{1-4}$alkyl; in particular $R^4$ represents methyl, ethyl, methoxy, fluor, chloro or bromo;
(vi) $R^5$ represents hydrogen, halo, cyano, amino, phenyl, hydroxy, $C_{1-4}$alkyloxycarbonyl-, hydroxycarbonyl, $NR^{13}R^{14}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$; in particular $R^5$ represents hydrogen, halo, cyano, amino, phenyl, hydroxy, $C_{1-4}$alkyloxycarbonyl-, hydroxycarbonyl, $NR^{13}R^{14}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$; more in particular $R^5$ represents halo, cyano, amino, phenyl, hydroxy, $C_{1-4}$alkyloxycarbonyl-, hydroxycarbonyl, $NR^{13}R^{14}$ or $C_{1-4}$alkyl substituted with one or more substituents selected from hydroxycarbonyl, phenyl, $C_{1-4}$alkyloxy or $NR^{15}R^{16}$; even more particular $R^5$ represents hydrogen or hydroxy; in particular hydroxy or amino.
(vii) $R^{11}$ and $R^{12}$ each independently represent hydrogen, $C_{1-4}$alkyl or $C_{1-4}$alkylcarbonyl-; in particular $R^{11}$ and $R^{12}$ represent methyl;
(viii) $R^{13}$ and $R^{14}$ each independently represent hydrogen, $C_{1-4}$alkyl, $C_{1-6}$alkyl-$SO_2$—, mono- or di($C_{1-4}$alkyl) amino-$SO_2$—, $Ar^1$—$SO_2$, mono- or di($C_{1-4}$alkyl) amino-carbonyl-, $C_{1-4}$alkyl-oxycarbonyl or $C_{1-4}$alkyl-carbonyl- wherein said $C_{1-6}$alkyl-$SO_2$—, $C_{1-4}$alkyl-oxycarbonyl or $C_{1-4}$alkyl-carbonyl- are each independently and optionally substituted with one, two or three substituents selected from halo, $C_{1-4}$alkyloxycarbonyl, $NR^{19}R^{20}$ and $Het^2$; in particular $R^{13}$ represents hydrogen or $C_{1-4}$alkyl and $R^{14}$ represents $C_{1-4}$alkyl, $C_{1-6}$alkyl-$SO_2$— or mono- or di($C_{1-4}$alkyl)amino-$SO_2$—; even more particular $R^{13}$ represents hydrogen or methyl and $R^{14}$ represents methyl, methyl-$SO_2$—, ethyl-$SO_2$— or mono- or di(methyl)amino-$SO_2$—

(ix) $R^{17}$ and $R^{18}$ each independently represent hydrogen or $C_{1-4}$alkyl; in particular $R^{17}$ and $R^{18}$ represent methyl;

(x) $R^{19}$ and $R^{20}$ each independently represent hydrogen or $C_{1-4}$alkyl optionally substituted with hydroxy; in particular $R^{19}$ and $R^{20}$ each independently represent hydrogen, methyl or hydroxyethyl;

(xi) $R^{21}$ and $R^{22}$ each independently represent hydrogen or $Ar^2$; in particular $R^{21}$ and $R^{22}$ each independently represent hydrogen or methylphenyl;

(xii) $R^{23}$ and $R^{24}$ each independently represent hydrogen or $Het^4$; in particular $R^{23}$ and $R^{24}$ each independently represent hydrogen or piperidinyl;

(xiii) $Het^2$ represents morpholinyl;

(xiv) $Het^3$ represents morpholinyl;

(xv) $Het^4$ represents piperidinyl;

(xvi) $Ar^1$ represents phenyl substituted with $C_{1-4}$alkyl; and (xvii) $Ar^2$ represents phenyl substituted with $C_{1-4}$alkyl.

Also of interest are those compounds of formula (I) wherein Z represents O, hereinafter referred to as the compounds of formula (I$^i$),

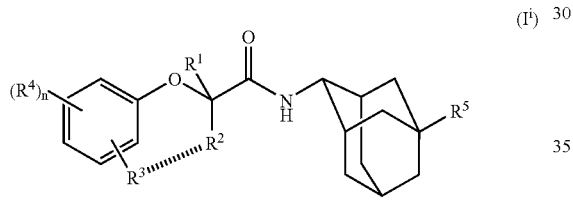

the N-oxide forms, the pharmaceutically acceptable addition salts and the stereochemically isomeric forms thereof, wherein n is 1, 2, 3, or 4;

$R^1$ represent hydrogen, cyano, hydroxy, or $C_{1-4}$alkyl optionally substituted with halo, $R^2$ represents hydrogen, $C_{1-4}$alkyl, or $C_{1-4}$alkyloxy;

$R^3$ represents hydrogen, $C_{1-4}$alkyl, $C_{1-4}$alkyloxy- or $R^3$ combined with $R^2$ form together a divalent radical selected from the group consisting of —O—CH$_2$— (a), —NR$^7$—CH$_2$— (b), —(CR$^8$R$^9$)$_m$- (c) and —CR$^{10}$= (d) wherein m represents 1 or 2 and $R^7$, $R^8$, $R^9$ and $R^{10}$ are each independently selected from hydrogen or $C_{1-4}$alkyl;

$R^4$ represents hydrogen, halo, hydroxy, cyano, amino, $NR^{11}R^{12}$, $C_{1-4}$alkyloxycarbonyl, hydroxycarbonyl, $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;

$R^5$ represents hydrogen, halo, cyano, amino, phenyl, hydroxy, $C_{1-4}$alkyloxycarbonyl-, hydroxycarbonyl-, $Het^1$, —$NR^{13}R^{14}$, —O—(C=O)—$NR^{21}R^{22}$, —O—(C=O)—$C_{1-4}$alkyl, carbonyl-$NR^{23}R^{24}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from halo, hydroxy, hydroxycarbonyl, phenyl, $C_{1-4}$alkyloxy or $NR^{17}R^{18}$, or $R^5$ represents —O(C=O)—$C_{1-4}$alkyl substituted with one or more amino, hydroxy, $Het^3$ or halo substituents;

$R^6$ represents hydrogen or $C_{1-4}$alkyl;

$R^{11}$ and $R^{12}$ each independently represent hydrogen, $C_{1-4}$alkyl, $C_{1-4}$alkyloxycarbonyl- or $C_{1-4}$alkylcarbonyl-;

$R^{13}$ and $R^{14}$ each independently represent hydrogen, $C_{1-4}$alkyl, $C_{1-6}$alkyl-$SO_2$—, mono- or di($C_{1-4}$alkyl)amino-$SO_2$—, $Ar^1$—$SO_2$, mono- or di($C_{1-4}$alkyl) amino-carbonyl-, $C_{1-4}$alkyl-oxycarbonyl or $C_{1-4}$alkylcarbonyl- wherein said $C_{1-6}$alkyl-$SO_2$—, $C_{1-4}$alkyl-oxycarbonyl or $C_{1-4}$alkylcarbonyl- are each independently and optionally substituted with one, two or three substituents selected from halo, $C_{1-4}$alkyloxycarbonyl, $NR^{19}R^{20}$ and $Het^2$;

$R^{15}$ and $R^{16}$ each independently represent hydrogen, $C_{1-4}$alkyl, $C_{1-4}$alkyloxycarbonyl or $C_{1-4}$alkylcarbonyl-; in particular hydrogen, $C_{1-4}$alkyl or $C_{1-4}$alkylcarbonyl-;

$R^{17}$ and $R^{18}$ each independently represent hydrogen, $C_{1-4}$alkyl, $C_{1-4}$alkyloxycarbonyl or $C_{1-4}$alkylcarbonyl-; in particular hydrogen, $C_{1-4}$alkyl or $C_{1-4}$alkylcarbonyl;

$R^{19}$ and $R^{20}$ each independently represent hydrogen, $C_{1-4}$alkylcarbonyl or $C_{1-4}$alkyl optionally substituted with one or more substituents selected from halo or hydroxy; in particular optionally substituted with hydroxy;

$R^{21}$ and $R^{22}$ each independently represent hydrogen, $Ar^2$ or $C_{1-4}$alkyl optionally substituted with one or more substituents selected from halo or hydroxy; in particular optionally substituted with hydroxy;

$R^{23}$ and $R^{24}$ each independently represent hydrogen, $C_{1-4}$alkylcarbonyl, $Het^4$ or $C_{1-4}$alkyl optionally substituted with hydroxy;

$Het^1$ represents pyrrolinyl, pyrrolidinyl, pyrrolyl, oxazolyl, isoxazolyl or a radical of formula

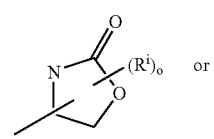

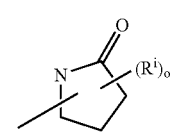

wherein $R^i$ represents hydrogen or $C_{1-4}$alkyl and o is 1 or 2; in particular $Het^1$ represents a radical of formula

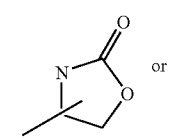

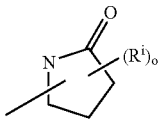

wherein $R^i$ represents hydrogen or $C_{1-4}$alkyl and o is 1 or 2;

Het² represents morpholinyl, piperidinyl, piperazinyl, thiomorpholinyl or pyrrolidinyl; in particular Het² represents morpholinyl;

Het³ represents morpholinyl, piperidinyl, piperazinyl, thiomorpholinyl or pyrrolidinyl; in particular Het³ represents morpholinyl;

Het⁴ represents piperidinyl, morpholinyl, piperazinyl, thiomorpholinyl or pyrrolidinyl; in particular Het⁴ represents piperidinyl;

Ar¹ represents phenyl optionally substituted with $C_{1-4}$alkyl; and

Ar² represents phenyl optionally substituted with $C_{1-4}$alkyl; provided however that said compound of formula (I') is other than Acetamide, N-tricyclo[3.3.1.1³,⁷]dec-2-yl-2-[3-(trifluoromethyl)phenoxy]-(9CI)

Acetamide, 2-[4-(1-methylpropyl)phenoxy]-N-tricyclo[3.3.1.1³,⁷]dec-2-yl-(9CI)

Butanamide, 2-phenoxy-N-tricyclo[3.3.1.1³,⁷]dec-2-yl-(9CI)

Acetamide, 2-(2-bromo-4-ethylphenoxy)-N-tricyclo[3.3.1.1³,⁷]dec-2-yl-(9CI)

Acetamide, N-tricyclo[3.3.1.1³,⁷]dec-2-yl-2-(2,3,5-trimethylphenoxy)-(9CI)

Acetamide, 2-(2,3-dimethylphenoxy)-N-tricyclo[3.3.1.1³,⁷]dec-2-yl-(9CI)

Acetamide, 2-(2,4-dibromo-6-methylphenoxy)-N-tricyclo[3.3.1.1³,⁷]dec-2-yl-(9CI)

Acetamide, 2-(4-chloro-2-methylphenoxy)-N-tricyclo[3.3.1.1³,⁷]dec-2-yl-(9CI)

Acetamide, 2-(3,5-dimethylphenoxy)-N-tricyclo[3.3.1.1³,⁷]dec-2-yl-(9CI)

Acetamide, 2-(2-chlorophenoxy)-N-tricyclo[3.3.1.1³,⁷]dec-2-yl-(9CI)

Acetamide, 2-[4-(1,1-dimethylethyl)phenoxy]-N-tricyclo[3.3.1.1³,⁷]dec-2-yl-(9CI)

Acetamide, 2-[(4-chlorophenyl)thio]-N-tricyclo[3.3.1.1³,⁷]dec-2-yl-(9CI)

Acetamide, 2-[5-methyl-2-(1-methylethyl)phenoxy]-N-tricyclo[3.3.1.1³,⁷]dec-2-yl-(9CI)

Acetamide, 2-(4-ethylphenoxy)-N-tricyclo[3.3.1.1³,⁷]dec-2-yl-(9CI)

Acetamide, 2-(2,5-dimethylphenoxy)-N-tricyclo[3.3.1.1³,⁷]dec-2-yl-(9CI)

Acetamide, 2-(3,4-dimethylphenoxy)-N-tricyclo[3.3.1.1³,⁷]dec-2-yl-(9CI)

Acetamide, 2-(2,4-dimethylphenoxy)-N-tricyclo[3.3.1.1³,⁷]dec-2-yl-(9CI)

Acetamide, 2-(4-bromo-2-methylphenoxy)-N-tricyclo[3.3.1.1³,⁷]dec-2-yl-(9CI)

Acetamide, 2-(4-bromo-3,5-dimethylphenoxy)-N-tricyclo[3.3.1.1³,⁷]dec-2-yl-(9CI)

Acetamide, 2-[4-(1-methylethyl)phenoxy]-N-tricyclo[3.3.1.1³,⁷]dec-2-yl-(9CI)

Acetamide, 2-(4-bromo-2-chlorophenoxy)-N-tricyclo[3.3.1.1³,⁷]dec-2-yl-(9CI)

Acetamide, 2-(4-chloro-3-methylphenoxy)-N-tricyclo[3.3.1.1³,⁷]dec-2-yl-(9CI)

Acetamide, 2-(4-methoxyphenoxy)-N-tricyclo[3.3.1.1³,⁷]dec-2-yl-(9CI)

Propanamide, 2-(2,4-dichlorophenoxy)-N-tricyclo[3.3.1.1³,⁷]dec-2-yl-(9CI)

Acetamide, 2-(2-bromo-4-methylphenoxy)-N-tricyclo[3.3.1.1³,⁷]dec-2-yl-(9CI)

Acetamide, 2-(4-chloro-3,5-dimethylphenoxy)-N-tricyclo[3.3.1.1³,⁷]dec-2-yl-(9CI)

Acetamide, 2-(4-bromo-3-methylphenoxy)-N-tricyclo[3.3.1.1³,⁷]dec-2-yl-(9CI)

Acetamide, 2-(2,4-dichlorophenoxy)-N-tricyclo[3.3.1.1³,⁷]dec-2-yl-(9CI)

Acetamide, 2-phenoxy-N-tricyclo[3.3.1.1³,⁷]dec-2-yl-(9CI)

Acetamide, 2-(4-bromophenoxy)-N-tricyclo[3.3.1.1³,⁷]dec-2-yl-(9CI)

Acetamide, 2-(4-methylphenoxy)-N-tricyclo[3.3.1.1³,⁷]dec-2-yl-(9CI)

Acetamide, 2-(3-bromophenoxy)-N-tricyclo[3.3.1.1³,⁷]dec-2-yl-(9CI)

Acetamide, 2-(4-chlorophenoxy)-N-tricyclo[3.3.1.1³,⁷]dec-2-yl-(9CI)

Acetamide, 2-(3-methylphenoxy)-N-tricyclo[3.3.1.1³,⁷]dec-2-yl-(9CI)

N-adamantan-2-yl-2-o-tolyloxy-acetamide;

or when $R^5$ represents hydrogen in said compound of formula (I'), then $R^1$ and $R^2$ represent $C_{1-4}$alkyl.

In particular those compounds of formula (I') wherein is 1, 2, 3, or 4;

$R^1$ represent hydrogen, cyano, hydroxy, or $C_{1-4}$alkyl optionally substituted with halo, $R^2$ represents hydrogen, $C_{1-4}$alkyl, or $C_{1-4}$alkyloxy-;

$R^3$ represents hydrogen, $C_{1-4}$alkyl, $C_{1-4}$alkyloxy- or $R^3$ combined with $R^2$ form together a divalent radical selected from the group consisting of —O—CH₂— (a), —NR⁷—CH₂— (b), —(CR⁸R⁹)$_m$- (c) and —CR¹⁰= (d) wherein m represents 1 or 2 and $R^7$, $R^8$, $R^9$ and $R^{10}$ are each independently selected from hydrogen or $C_{1-4}$alkyl;

$R^4$ represents hydrogen, halo, hydroxy, cyano, amino, NR¹¹R¹², $C_{1-4}$alkyloxy- optionally substituted with one or where possible two or three substituents selected from hydroxy and halo or $R^4$ represents $C_{1-4}$alkyl optionally substituted with one or where possible two or three substituents selected from hydroxy and halo;

$R^5$ represents hydrogen, halo, cyano, amino, phenyl, hydroxy, $C_{1-4}$alkyloxycarbonyl, hydroxycarbonyl, NR¹³R¹⁴ or $C_{1-4}$alkyl optionally substituted with one or more substituents selected from hydroxycarbonyl, phenyl, $C_{1-4}$alkyloxy or NR¹⁵R¹⁶ or $R^5$ represents $C_{1-4}$alkyloxy optionally substituted with one or more substituents selected from hydroxycarbonyl, phenyl, $C_{1-4}$alkyloxy or NR¹⁷R¹⁸; in particular $R^5$ represents halo, cyano, amino, phenyl, hydroxy, $C_{1-4}$alkyloxycarbonyl-, hydroxycarbonyl, NR¹³R¹⁴ or $C_{1-4}$alkyl optionally substituted with one or more substituents selected from hydroxycarbonyl, phenyl, $C_{1-4}$alkyloxy or NR¹⁵R¹⁶ or $R^5$ represents $C_{1-4}$alkyloxy optionally substituted with one or more substituents selected from hydroxycarbonyl, phenyl, $C_{1-4}$alkyloxy or NR¹⁷R¹⁸

$R^6$ represents hydrogen or $C_{1-4}$alkyl;

$R^{11}$ and $R^{12}$ each independently represent hydrogen, $C_{1-4}$alkyl or $C_{1-4}$alkylcarbonyl-;

$R^{13}$ and $R^{14}$ each independently represent hydrogen, $C_{1-4}$alkyl or $C_{1-4}$alkylcarbonyl-;

$R^{15}$ and $R^{16}$ each independently represent hydrogen, $C_{1-4}$alkyl or $C_{1-4}$alkylcarbonyl-;

$R^{17}$ and $R^{18}$ each independently represent hydrogen, $C_{1-4}$alkyl or $C_{1-4}$alkylcarbonyl-; provided however that when $R^5$ represents hydrogen in said compound of formula (I') then $R^1$ and $R^2$ represent $C_{1-4}$alkyl.

A particularly preferred group of compounds are those compounds of formula (I) wherein one or more of the following restrictions apply;

(i) n is 1, 2 or 3; in particular n is 1

(ii) Z represents O, S, $NR^6$, SO or $SO_2$; in particular Z represents O;

(iii) $R^1$ represents hydrogen or $C_{1-4}$alkyl; in particular $R^1$ represents $C_{1-4}$alkyl; even more particular methyl;

(iv) $R^2$ represents hydrogen or $C_{1-4}$alkyl; in particular $R^2$ represents $C_{1-4}$alkyl; even more particular methyl;

(v) $R^3$ represents hydrogen or $C_{1-4}$alkyl; in particular $R^3$ represents $C_{1-4}$alkyl; even more particular methyl; or $R^3$ combined with $R^2$ form together a divalent radical selected from the group consisting of —O—CH$_2$— (a), —NR$^7$—CH$_2$— (b), —(CR$^8$R$^9$)$_m$- (c) and —CR$^{10}$═ (d) wherein m represents 1 or 2 and $R^7$, $R^8$, $R^9$ and $R^{10}$ are each independently selected from hydrogen or $C_{1-4}$alkyl;

(vi) $R^4$ represents hydrogen, halo, $NR^{11}R^{12}$, hydroxycarbonyl, $C_{1-4}$alkyloxy- or $C_{1-4}$alkyl optionally substituted with one or where possible two or three halo substituents; in particular $R^4$ represents Cl, F, Br, dimethylamino, methylcarbonylamine, methoxy, methyl or trifluoromethyl;

(vii) $R^5$ represents hydrogen, amino, hydroxy, Het$^1$ or $NR^{13}R^{14}$; in particular $R^5$ represents amino, hydroxy, methylsulfonylamine, ethylsulfonylamine, dimethylaminesulfonylamine, hydroxycarbonyl, 3-methyl-2-oxo-pyrrolidinyl or 2-oxo-oxazolidinyl;

(viii) $R^{11}$ represents hydrogen or $C_{1-4}$alkyl; in particular $R^{11}$ represents hydrogen or methyl;

(ix) $R_{12}$ represents $C_{1-4}$alkyl or $C_{1-4}$alkylcarbonyl;

(x) $R^{13}$ represents hydrogen or $C_{1-4}$alkyl; in particular $R^{13}$ represents hydrogen or methyl;

(xi) $R^{14}$ represents $C_{1-4}$alkyl, $C_{1-6}$alkyl-SO$_2$— or mono- or di($C_{1-4}$alkyl)amino-SO$_2$—;

(xii) Het$^1$ represents pyrrolidinyl, oxazolyl or a radical of formula

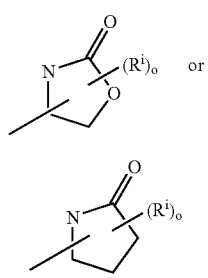

In a more preferred embodiment the compounds of formula (I) are selected from the group consisting of:

2,3-dihydro-N-[(1R,3S)-5-hydroxytricyclo[3.3.1.1$^{3,7}$]dec-2-yl]-1,4-benzodioxin-2-carboxamide,
N-[(1R,3S)-5-hydroxytricyclo[3.3.1.1$^{3,7}$]dec-2-yl]-2-methyl-2-(2-methylphenoxy)propanamide,
N-[(1R,3S)-5-hydroxytricyclo[3.3.1.1$^{3,7}$]dec-2-yl]-2-methyl-2-(4-methylphenoxy)propanamide,
2-(3,5-dimethylphenoxy)-N-[(1R,3S)-5-hydroxytricyclo[3.3.1.1$^{3,7}$]dec-2-yl]-2-methylpropanamide,
N-[(1R,3S)-5-hydroxytricyclo[3.3.1.1$^{3,7}$]dec-2-yl]-3-methyl-2-benzofurancarboxamide,
3,4-dihydro-N-[(1R,3S)-5-hydroxytricyclo[3.3.1.1$^{3,7}$]dec-2-yl]-2H-1-benzopyran-2-carboxamide,
2-(4-chloro-2-methylphenoxy)-N-[(1R,3S)-5-hydroxytricyclo[3.3.1.1$^{3,7}$]dec-2-yl]-2-methyl-propanamide,
6-fluoro-3,4-dihydro-N-[(1R,3S)-5-hydroxytricyclo[3.3.1.1$^{3,7}$]dec-2-yl]-,
(2R)-2H-1-benzopyran-2-carboxamide,
N-[(1R,3S)-5-hydroxytricyclo[3.3.1.1$^{3,7}$]dec-2-yl]-2-benzofurancarboxamide,
2,3-dihydro-N-[(1R,3S)-5-hydroxytricyclo[3.3.1.1$^{3,7}$]dec-2-yl]-2-benzofuran-carboxamide,
N-[(1R,3S)-5-hydroxytricyclo[3.3.1.1$^{3,7}$]dec-2-yl]-7-methoxy-2-benzofuran-carboxamide,
N-[(1R,3S)-5-hydroxytricyclo[3.3.1.1$^{3,7}$]dec-2-yl]-2-methyl-2-[(4-methylphenyl)amino]propanamide,
3,4-dihydro-6-hydroxy-N-[(1R,3S)-5-hydroxytricyclo[3.3.1.1$^{3,7}$]dec-2-yl]-2,5,7,8-tetramethyl-2H-1-benzopyran-2-carboxamide,
2-[(4-chlorophenyl)sulfonyl]-N-[(1R,3S)-5-hydroxytricyclo[3.3.1.1$^{3,7}$]dec-2-yl]-2-methyl-propanamide,
2-[(4-chlorophenylthio]-N-[(1R,3S)-5-hydroxytricyclo[3.3.1.1$^{3,7}$]dec-2-yl]-2-methyl-propanamide,
2,2-difluoro-N-[(1R,3S)-5-hydroxytricyclo[3.3.1.1$^{3,7}$]dec-2-yl]-2-(3-methylphenoxy)-acetamide,
2-(3,5-dimethylphenoxy)-2-methyl-N-tricyclo[3.3.1.1$^{3,7}$]dec-2-yl-propanamide,
N-[(1R,3S)-5-hydroxytricyclo[3.3.1.1$^{3,7}$]dec-2-yl]-2-methyl-2-(3-methylphenoxy)-propanamide,
3,4-dihydro-N-[(1R,3S)-5-hydroxytricyclo[3.3.1.1$^{3,7}$]dec-2-yl]-6-methyl-2H-1,4-benzoxazine-2-carboxamide,
N-[(1R,3S)-5-hydroxytricyclo[3.3.1.1$^{3,7}$]dec-2-yl]-2-(3-methoxyphenoxy)-2-methyl-propanamide,
2-(2-bromophenoxy)-N-[(1R,3S)-5-hydroxytricyclo[3.3.1.1$^{3,7}$]dec-2-yl]-2-methyl-propanamide,
2-(3,5-dimethoxyphenoxy)-N-[(1R,3S)-5-hydroxytricyclo[3.3.1.1$^{3,7}$]dec-2-yl]-2-methyl-propanamide,
2-[3-(dimethylamino)phenoxy]-N-[(1R,3S)-5-hydroxytricyclo[3.3.1.1$^{3,7}$]dec-2-yl]-2-methyl-propanamide,
2-[3-(acetylamino)phenoxy]-N-[(1R,3S)-5-hydroxytricyclo[3.3.1.1$^{3,7}$]dec-2-yl]-2-methyl-propanamide,
N-[(1R,3S)-5-hydroxytricyclo[3.3.1.1$^{3,7}$]dec-2-yl]-2-methyl-2-[3-(trifluoromethyl)-phenoxy]-propanamide,
2-[(4-chlorophenyl)sulfinyl]-N-[(1R,3S)-5-hydroxytricyclo[3.3.1.1$^{3,7}$]dec-2-yl]-2-methyl-propanamide,
2-(4-Chloro-phenoxy)-N-[(1R,3S)-5-hydroxytricyclo[3.3.1.1$^{3,7}$]dec-2-yl]-2-methyl-propionamide,
N-[(1R,3S)-5-aminotricyclo[3.3.1.1$^{3,7}$]dec-2-yl]-2-(2-chloro-phenoxy)-2-methyl-propionamide,
N-[(1R,3S)-5-aminotricyclo[3.3.1.1$^{3,7}$]dec-2-yl]-2-methyl-2-(2-trifluoromethyl-phenoxy)-propionamide,
N-[(1R,3S)-5-aminotricyclo[3.3.1.1$^{3,7}$]dec-2-yl]-2-(4-chloro-2-methyl-phenoxy)-2-methyl-propionamide,
N-[(1R,3S)-5-aminotricyclo[3.3.1.1$^{3,7}$]dec-2-yl]-2-(4-chloro-phenoxy)-2-methyl-propionamide,
N-[(1R,3S)-5-aminotricyclo[3.3.1.1$^{3,7}$]dec-2-yl]-2-(2-chloro-5-trifluoromethyl-phenoxy)-2-methyl-propionamide,
N-[(1R,3S)-5-aminotricyclo[3.3.1.1$^{3,7}$]dec-2-yl]-2-methyl-2-o-tolyloxy-propionamide,
N-[(1R,3S)-5-aminotricyclo[3.3.1.1$^{3,7}$]dec-2-yl]-2-(2-chloro-4-methoxy-phenoxy)-2-methyl-propionamide,
N-[(1R,3S)-5-aminotricyclo[3.3.1.1$^{3,7}$]dec-2-yl]-2-(4-fluoro-2-methoxy-phenoxy)-2-methyl-propionamide, (3R,5S)-4-[2-(4-Chloro-2-methyl-phenoxy)-2-methyl-propionylamino]tricyclo[3.3.1.1$^{3,7}$]decane-1-carboxylic acid, 2-(4-Chloro-2-methyl-phenoxy)-N-[(1R,3S)-5-(dimethylamino)sulfonylaminotricyclo[3.3.1.1$^{3,7}$]dec-2-yl]-2-methyl-propionamide, 2-(4-Chloro-2-methyl-phenoxy)-2-methyl-N-[(1R,3S)-5-(3-methyl-2-oxo-pyrrolidin-1-yl)tricyclo[3.3.1.1$^{3,7}$]dec-2-yl]]-propionamide, N-[(1R,3S)-5-methanesulfonylaminotricyclo[3.3.1.1$^{3,7}$]dec-2-yl]-2-methyl-2-(3-trifluoro-methyl-phenoxy)-propionamide, N-[(1R,3S)-5-(dimethylamino)sulfonylaminotricyclo[3.3.1.1$^{3,7}$]dec-2-yl]-2-methyl-2-(3-trifluoromethyl-phenoxy)-propionamide, N-[(1R,3S)-5-Ethanesulfonylaminotricyclo[3.3.1.1$^{3,7}$]dec-2-yl]-2-methyl-2-(3-trifluoro-methyl-phenoxy)-propionamide, 2-(4-Chloro-2-methyl-phenoxy)-N-[(1R,3S)-5-methanesulfonylaminotricyclo[3.3.1.1$^{3,7}$]dec-2-yl]-2-methyl-propionamide, 2-(3-Bromo-phenoxy)-N-[(1R,3S)-5-methanesulfonylaminotricyclo[3.3.1.1$^{3,7}$]dec-2-yl]-2-methyl-propionamide, 2-(4-Chloro-phenoxy)-N-[(1R,3S)-5-methanesulfonylaminotricyclo[3.3.1.1$^{3,7}$]dec-2-yl]-2-methyl-propionamide, 2-(3-Bromo-phenoxy)-2-methyl-N-[(1R,3S)-5-(2-oxo-oxazolidin-3-yl)tricyclo[3.3.1.1$^{3,7}$]dec-2-yl]]-propionamide.

In an even more preferred embodiment the compounds of formula (I) are selected from the group consisting of;

2,3-dihydro-N-[(1R,3S)-5-hydroxytricyclo[3.3.1.1$^{3,7}$]dec-2-yl]-1,4-benzodioxin-2-carboxamide, N-[(1R,3S)-5-hydroxytricyclo[3.3.1.1$^{3,7}$]dec-2-yl]-2-methyl-2-(2-methylphenoxy)propanamide, N-[(1R,3S)-5-hydroxytricyclo[3.3.1.1$^{3,7}$]dec-2-yl]-2-methyl-2-(4-methylphenoxy)propanamide, 2-(3,5-dimethylphenoxy)-N-[(1R,3S)-5-hydroxytricyclo[3.3.1.1$^{3,7}$]dec-2-yl]-2-methyl-propanamide, N-[(1R,3S)-5-hydroxytricyclo[3.3.1.1$^{3,7}$]dec-2-yl]-3-methyl-2-benzofurancarboxamide, 3,4-dihydro-N-[(1R,3S)-5-hydroxytricyclo[3.3.1.1$^{3,7}$]dec-2-yl]-2H-1-benzopyran-2-carboxamide, 2-(4-chloro-2-methylphenoxy)-N-[(1R,3S)-5-hydroxytricyclo[3.3.1.1$^{3,7}$]dec-2-yl]-2-methyl-propanamide, 2-(4-Chloro-2-methyl-phenoxy)-N-[(1R,3S)-5-methanesulfonylaminotricyclo[3.3.1.1$^{3,7}$]dec-2-yl]-2-methyl-propionamide, 2-(4-Chloro-2-methyl-phenoxy)-N-[(1R,3S)-5-(dimethylamino)sulfonylaminotricyclo[3.3.1.1$^{3,7}$]dec-2-yl]-2-methyl-propionamide, 2-(4-Chloro-phenoxy)-N-[(1R,3S)-5-hydroxytricyclo[3.3.1.1$^{3,7}$]dec-2-yl]-2-methyl-propionamide, N-[(1R,3S)-5-(dimethylamino)sulfonylaminotricyclo[3.3.1.1$^{3,7}$]dec-2-yl]-2-methyl-2-(3-trifluoromethyl-phenoxy)-propionamide, N-[(1R,3S)-5-methanesulfonylaminotricyclo[3.3.1.1$^{3,7}$]dec-2-yl]-2-methyl-2-(3-trifluoromethyl-phenoxy)-propionamide, N-[(1R,3S)-5-aminotricyclo[3.3.1.1$^{3,7}$]dec-2-yl]-2-(2-chloro-phenoxy)-2-methyl-propionamide, N-[(1R,3S)-5-aminotricyclo[3.3.1.1$^{3,7}$]dec-2-yl]-2-methyl-2-(2-trifluoromethyl-phenoxy)-propionamide, N-[(1R,3S)-5-Ethanesulfonylaminotricyclo[3.3.1.1$^{3,7}$]dec-2-yl]-2-methyl-2-(3-trifluoromethyl-phenoxy)-propionamide, (3R,5S)-4-[2-(4-Chloro-2-methyl-phenoxy)-2-methyl-propionylamino]-tricyclo[3.3.1.1$^{3,7}$]decane-1-carboxylic acid, N-[(1R,3S)-5-aminotricyclo[3.3.1.1$^{3,7}$]dec-2-yl]-2-(4-chloro-2-methyl-phenoxy)-2-methyl-propionamide, 2-(4-Chloro-2-methyl-phenoxy)-2-methyl-N-[(1R,3S)-5-(3-methyl-2-oxo-pyrrolidin-1-yl)tricyclo[3.3.1.1$^{3,7}$]dec-2-yl]]-propionamide, 2-(3-Bromo-phenoxy)-2-methyl-N-[(1R,3S)-5-(2-oxo-oxazolidin-3-yl)-tricyclo[3.3.1.1$^{3,7}$]dec-2-yl]]-propionamide, 2-(3-Bromo-phenoxy)-N-[(1R,3S)-5-methanesulfonylamino-tricyclo[3.3.1.1$^{3,7}$]dec-2-yl]-2-methyl-propionamide, or 2-(4-Chloro-phenoxy)-N-[(1R,3S)-5-methanesulfonylaminotricyclo[3.3.1.1$^{3,7}$]dec-2-yl]-2-methyl-propionamide.

In a further aspect the present invention provides any of the aforementioned group of compounds for use as a medicine. In particular in the treatment or prevention of pathologies associated with excess cortisol formation such as obesity, diabetes, obesity related cardiovascular diseases, stress and glaucoma. It is accordingly a further aspect of the present invention to provide the use of any of the aforementioned group of compounds in the manufacture of a medicament for treating pathologies associated with excess cortisol formation such as obesity, diabetes, obesity related cardiovascular diseases, stress and glaucoma. PCT. International patent application WO 2004/089416 provides the benefits of a combination therapy comprising the administration of a 11β-HSD1 inhibitor and an antihypertensive agent in the treatment of e.g. insulin resistance, dyslipidemia, obesity and hypertension, in particular in the treatment of hypertension. It is accordingly an object of the present invention to provide any of the aforementioned group of compounds in a combination therapy with an antihypertensive agent, such as for example alprenolol, atenolol, timolol, pindolol, propranolol, metoprolol, bisoprololfumerate, esmolol, acebutelol, acebutolol, betaxolol, celiprolol, nebivolol, tertatolol, oxprenolol, amusolalul, carvedilol, labetalol, S-atenolol, OPC-1085, quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP00481522), omapatrilat, gemopatrilat and GW-660511, nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, doxazosin, urapidil, prazosin, terazosin, bunazosin and OPC-28326, bendroflumetazide, chlorothalidone, hydrochlorothiazide and clopamide, bumetanide, furosemide, torasemide, amiloride, spironolactone, ABT-546, ambrisetan, atrasentan, SB-234551, CI-1034, S-0139, YM-598, bosentan, J-104133, aliskiren, OPC-21268, tolvaptan, SR-121463, OPC-31260, Nesiritide, irbesartan, candesartancilexetil, losartan, valsartan, telmisartan, eprosartan, candesartan, CL-329167, eprosartan, iosartan, olmesartan, pratosartan, TA-606, YM-358, fenoldopam, ketanserin, naftopidil, N-0861, FK-352, KT2-962, ecadotril, LP-805, MYD-37, nolomirole, omacor, treprostinil, beraprost, ecraprost, PST-2238, KR-30450, PMD-3117, Indapamides, CGRP-unigene, guanylate cyclase stimulators, hydralazines, methyidopa, docarpamine, moxonidine, CoAprovel, and MondoBiotech-811. In said aspect of the invention a pharmaceutical composition which, comprises the combination of a 11β-HSD1 inhibitor of the present invention and an antihypertensive agent, is provided.

PCT International application WO 2004/089415 provides the benefits of a combination therapy comprising the administration of a 11β-HSD1 inhibitor and a glucocorticoid receptor agonist for the reduction of undesirable side effects occurring during glucocorticoid receptor agonist therapy and for treating some forms of cancer, diseases and disorders having inflammation as a component. In particular in reducing the adverse effects of glucocorticoid receptor agonist therapy in indications of Cushing's disease, Cushing's syndrome, allergic-inflammatory diseases, adverse effects of glucocorticoid receptor agonist treatment of disorders of the respiratory system, adverse effects of glucocorticoid receptor agonist treatment of inflammatory bowel disease; adverse effects of glucocorticoid receptor agonist treatment of disorders of the immune system, connective tissue and joints; adverse effects of glucocorticoid receptor agonist treatment of endocrinological diseases; adverse effects of glucocorticoid receptor agonist treatment of hematological diseases; adverse effects of glucocorticoid receptor agonist treatment of cancer, chemotherapy-induced nausea, adverse effects of glucocorticoid receptor agonist treatment of diseases of muscle and at the neuro-muscular joint; adverse effects of glucocorticoid receptor agonist treatment in the context of surgery; transplantation; adverse effects of glucocorticoid receptor agonist treatment of brain abscess, nausea/vomiting, infections, hypercalcemia, adrenal hyperplasia, autoimmune hepatitis, spinal cord diseases, saccular aneurysms.

Examples for the indications wherein a combination of a 11β-HSD1 compound of the present invention with a glucocorticoid receptor agonists may be beneficial are: Cushing's disease, Cushing's syndrome, asthma, atopic dermatitis, cystic fibrosis, emphysema, bronchitis, hypersensitivity, pneumonitis, eosinophilic pneumonias, pulmonary fibrosis, Crohn's disease, Ulcerative colitis, reactive arthritis, rheumatoid arthritis, Sjogren's syndrome, systemic lupus erythematosus, lupus nephritis, Henoch-Schnlein purpura, Wegener's granulomatosis, temporal arteritis, systemic sclerosis, vasculitis, sarcoidosis, dermatomyositis-polymyositis, pemphigus vulgaris, hyperthyroidism, hypoaldosteronism, hypopituitarism, hemolytic anemia, thrombocytopenia, paroxysmal nocturnal hemoglobinuria, neoplastic compression of the spinal cord, brain tumours, acutelymphoblastic leukemia, Hodgkin's disease, chemotherapy-induced nausea, myasthenia gravis, heriditary myopathies, Duchenne muscular dystrophy, trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, trachea transplantation, intestinal transplantation, corneal transplantation, skin grafting, keratoplasty, lens implantation, brain absess, nausea/vomiting, infections, hypercalcemia, adrenal hyperplasia, autoimmune hepatitis, spinal cord diseases, and saccular aneurysms.

It is accordingly an object of the present invention to provide any of the aforementioned group of compounds in a combination therapy with a glucocorticoid receptor agonist, as well as pharmaceutical formulations comprising said combination of a compound of the present invention with a glucocorticoid receptor agonist. The glucocorticoid receptor agonist is, for example, selected from the group consisting of: betamethasone, dexamethasone, hydrocortisone, methylprednisolone, prednisolone, prednisone, beclomethasone, butixicort, clobetasol, flunisolide, flucatisone (and analogues), momethasone, triamcinolonacetonide, triamcinolonhexacetonide GW-685698, NXC-1015, NXC-1020, NXC-1021, NS-126, P-4112, P-4114, RU-24858 and T-25 series.

The N-2-adamantyl-2-phenoxy-acetamide derivatives of the present invention, hereinafter referred to as the compounds of formula (I'), are generally prepared by treatment of the appropriate alkylhalide (II) with the alcohol of formula (III) under art known conditions (Scheme 1). This reaction is usually performed by mixing the halide and phenol directly with solid KOH in Me$_2$SO or with HgO and HBF$_4$ in CH$_2$Cl$_2$. Alternatively, as described in the examples hereinafter, the reactive aroxide is obtained directly in the reaction mixture by mixing the halide and phenol in an appropriate solvent such as dioxane, in the presence of sodium hydride. The reaction temperature and the reaction time may be altered depending on the starting material or reagents but is usually performed overnight at at a temperature in the range of 60° C.-120° C., typically 90° C.

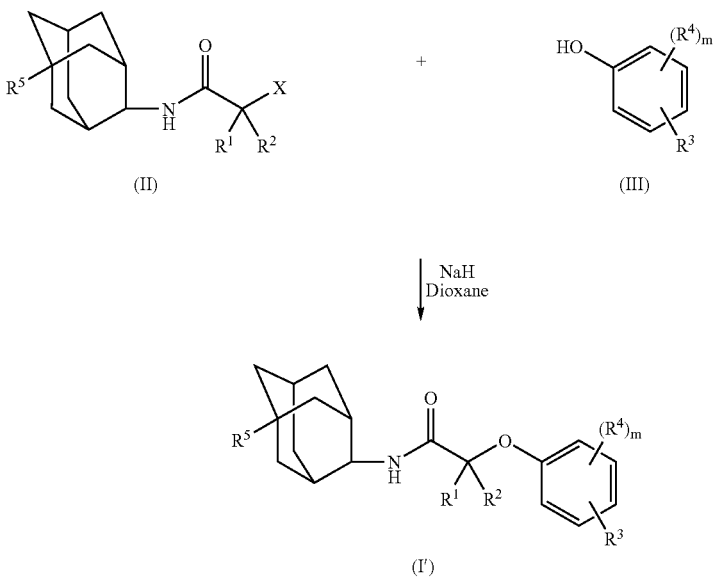

wherein $R^1$, $R^2$, $R^3$, $R^4$, $R^5$ are defeined as for the compounds of formula (I) hereinbefore and wherein X represents a halo atom, in particular, chloro or bromo.

The appropriate alkylhalide of formula (II) hereinbefore, is generally prepared by condensation of 2-adamantyl-amine (IV) with the appropriate carboxylic acid (V) in the presence of a coupling reagent, such as for example N,N'-dicyclohexylcarbodiimide (DCC), N,N'-carbonyldiimidazole (CDI), POCl$_3$, TiCl$_4$, sulfur chloride fluoride (SO$_2$ClF) or 1-(3-dimethylaminopropyl)-3-ethylcarbodiimide (EDCI) either in the presence or absence of hydroxybenzotriazole (HOBt) (Scheme 2). The reaction is typically performed by stirring the reaction mixture for a couple of hours (2-8 hours) at room temperature.

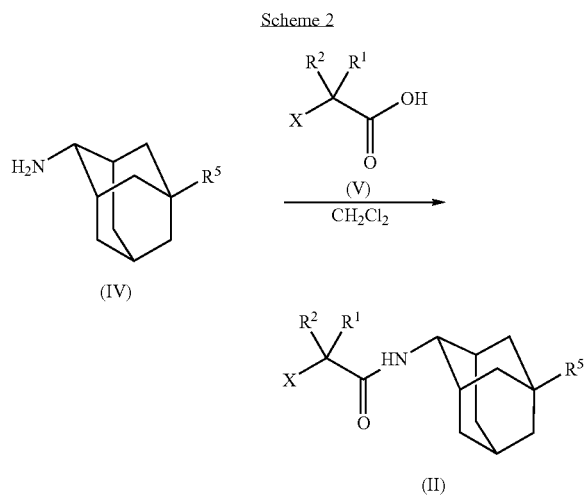

wherein $R^1$, $R^2$ and $R^5$ are defined as for the compounds of formula (I) hereinbefore and X represents a halo atom, in particular chloro or bromo.

In analogy with the preparation of the N-2-adamantyl-2-phenoxy-acetamide derivatives of the present invention (I'), those compounds wherein Z represents S, SO, SO$_2$ or NR$^6$ are prepared by reaction of the alkyl halide of formula (II) with the corresponding benzothiol, benzamine or benzene sulfinic acid ion using art known procedures, such as for example described in "Advanced Organic Chemistry" Jerry March—John Wiley & Sons, Inc.—third edition—New York—Section 0.38—page 360-361; Section 0.42—page 363 and Section 0.45—page 364-365 respectively.

The bicyclic adamantyl-amide derivatives of formula (I") can be prepared by any of several standard synthetic processes commonly used by those skilled in the art of organic chemistry and described for instance in; "Introduction to organic chemistry" Streitweiser and Heathcock—Macmillan Publishing Co., Inc.—second edition—New York—Section 24.7 (part A) p.753-756. In general the amides can be prepared through a base-catalyzed nucleophilic addition between the appropriate carboxylic acid (VI) with the amino-adamantyl derivatives of formula (VII) (scheme 3) or via a nucleophilic substitution reaction wherein the appropriate amine reacts with either the corresponding acyl halide (scheme 4), anhydride or ester, to yield the required amide.

When coupling the acids to the amines (as in Scheme 2 hereinbefore), standard coupling reagents such as N,N'-dicyclohexylcarbodiimide (DCC), N,N'-carbonyl-diimidazole (CDI), POCl$_3$, TiCl$_4$, sulfur chloride fluoride (SO$_2$ClF) or 1-(3-dimethylaminopropyl)-3-ethylcarbodiimide (EDCI) are used in the presence or absence of hydroxybenzotrialzole (HOBt). In general, adding the carboxylic acids of formula (VI) to the amino-adamantyl derivative of formula (VII) under base catalyzed reaction conditions results in the formation of the amine salt which is in equilibrium with its weak acid and base. To force the equilibrium to the formation of the amide of formula (I"), a dehydrogenating agent such as carbodiimides, for example DCC and CDI are added to the reaction mixture.

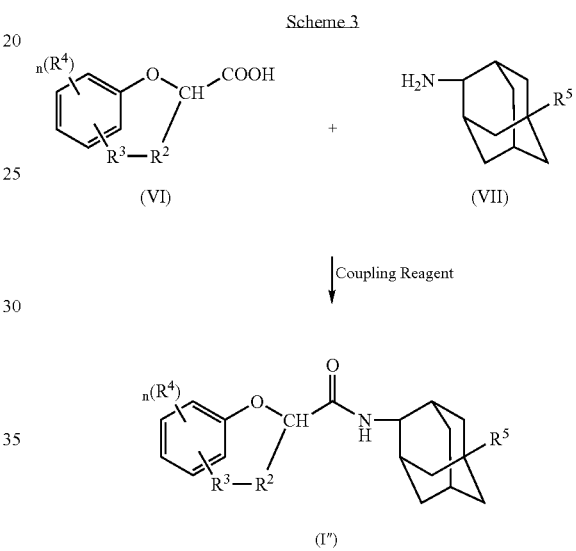

wherein $R^2$, $R^3$, $R^4$ and $R^5$ are defined as for the compounds of formula (I)

In an alternative embodiment the carboxylic acids are converted into the corresponding halides by reaction with, for example, thionyl chloride or oxalyl chloride. Subsequently said acyl halide (VIII) is added to the amino-adamantyl derivatives of formula (VII) to yield the amide of formula (I") using art known reaction procedures such as the Schotten-Baumann method.

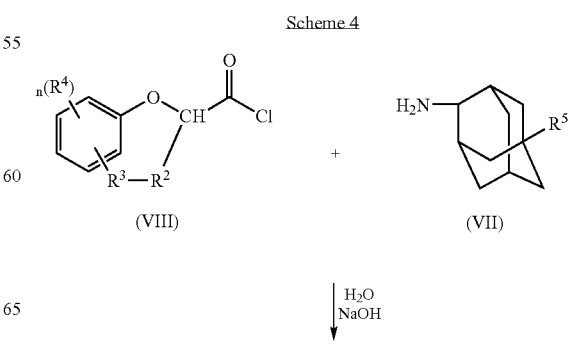

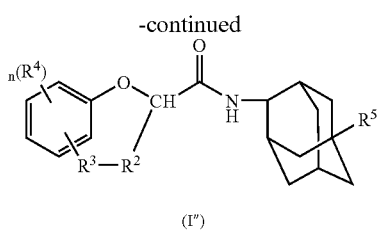

(I″)

The carboxylic acids of formula (VI) are readily available, for example commercially from Aldrich Chemicals, or when they are not commercially available, they may be readily prepared from available precursors using straightforward transformations that are well known to the person skilled in the art of organic chemistry.

For those compounds of formula (I) wherein Z represents O and $R^3$ combined with $R^2$ represent the bivalent radical represented by formula (a) or (b), for said compounds the bicyclic carboxylic acids of formula (VI) are prepared by coupling of aromatic 1,2-dihydroxy or 1,2-amino-hydroxy-benzo-derivatives of formula (IX) with 2,3-dibromo-ethyl-propionate in boiling acetone. Subsequently, an acidic or basic hydrolysis of the thus obtained esters (X) yields the bicyclic carboxylic acid intermediates of formula (VI).

methylpropanoic acid ethyl ester [CAS No 600-00-0] is reacted with the corresponding benzothiol, benzamine or benzene sulfinic acid ion using art known procedures, such as for example described in "Advanced Organic Chemistry" Jerry March—John Wiley & Sons, Inc.—third edition—New York—Section 0.38—page 360-361; Section 0.42—page 363 and Section 0.45—page 364-365 respectively. Subsequently coupling the thus obtained intermediate (XI) with the appropriate aminoadamantyl (VII) using standard coupling reagents such as N,N'-dicyclohexylcarbodiimide (DCC), N,N'-carbonyldiimidazole (CDI), $POCl_3$, $TiCl_4$, sulfur chloride fluoride ($SO_2ClF$) or 1-(3-dimethylaminopropyl)-3-ethylcarbodiimide (EDCI) in the presence or absence of hydroxybenzotrialzole (HOBt), yields the compounds of formula (I‴)

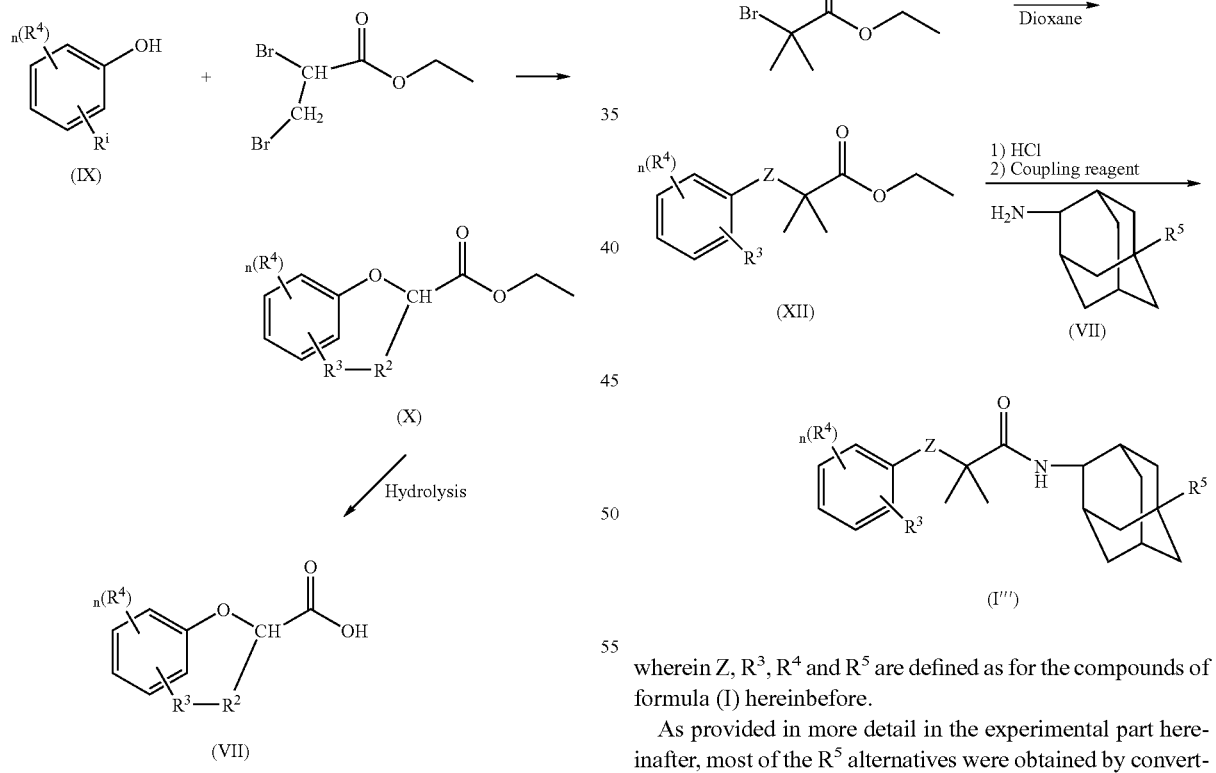

wherein Z, $R^3$, $R^4$ and $R^5$ are defined as for the compounds of formula (I) hereinbefore.

As provided in more detail in the experimental part hereinafter, most of the $R^5$ alternatives were obtained by converting the hydroxyl of general formula I″″ using art known conversion reactions as schematically represented the scheme hereinafter. As used therein;

R refers to $C_{1-4}$alkyl optionally substituted with one or more amino, hydroxy, $Het^3$ or halo substituents, wherein $Het^3$ is defined as for the compounds of formula (I) hereinbefore;

wherein $R^i$ represents hydroxy or amino and wherein $R^2$, $R^3$ and $R^4$ are defined as for the compounds of formula (I).

In analogy with the above, those compounds of the present invention wherein both $R^1$ and $R^2$ represent methyl, hereinafter referred to as the compounds of formula (I‴), can be prepared according to scheme 6. In a first step 2-bromo-2-

$R_{25}$, $R_{26}$ and $R_{27}$ each independently represent hydrogen, halo, or $C_{1-4}$alkyl wherein said $C_{1-4}$alkyl is optionally substituted with one, two or three substituents selected from halo, $C_{1-4}$alkyloxycarbonyl, $NR^{19}R^{20}$ and $Het^2$, wherein $R^{19}$, $R^{20}$ and $Het^2$ are defined as for the compounds of formula (I) hereinbefore;

$R_{28}$ and $R_{29}$ each independently represent hydrogen or $C_{1-4}$alkyl;

$R_{30}$ represents hydrogen or $C_{1-4}$alkyl wherein said $C_{1-4}$alkyl is optionally substituted with one, two or three substituents selected from halo, $C_{1-4}$alkyloxycarbonyl, $NR^{19}R^{20}$ and $Het^2$, wherein $R^{19}$, $R^{20}$ and $Het^2$ are defined as for the compounds of formula (I) hereinbefore;

$R_{31}$ represents $C_{1-6}$alkyl wherein said $C_{1-6}$alkyl is optionally substituted with one, two or three substituents selected from halo, $C_{1-4}$alkyloxycarbonyl, $NR^{19}R^{20}$ and $Het^2$, wherein $R^{19}$, $R^{20}$ and $Het^2$ are defined as for the compounds of formula (I) hereinbefore; and $Z$, $R^1$, $R^2$, $R^3$, $R^4$, $R^{13}$, $R^{14}$, $n$, $o$, and $R^i$ are defined as for the compounds of formula (I) hereinbefore.

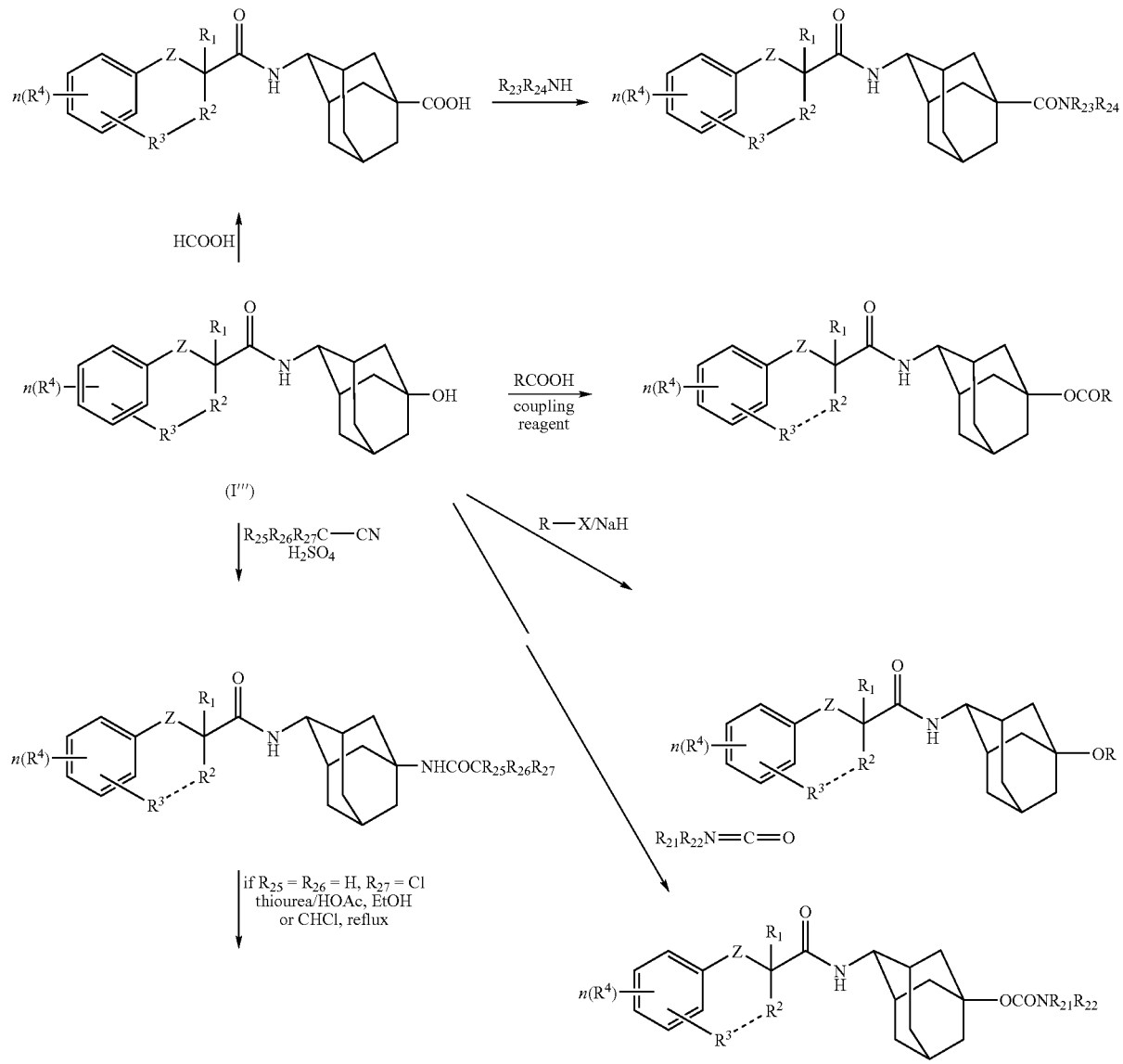

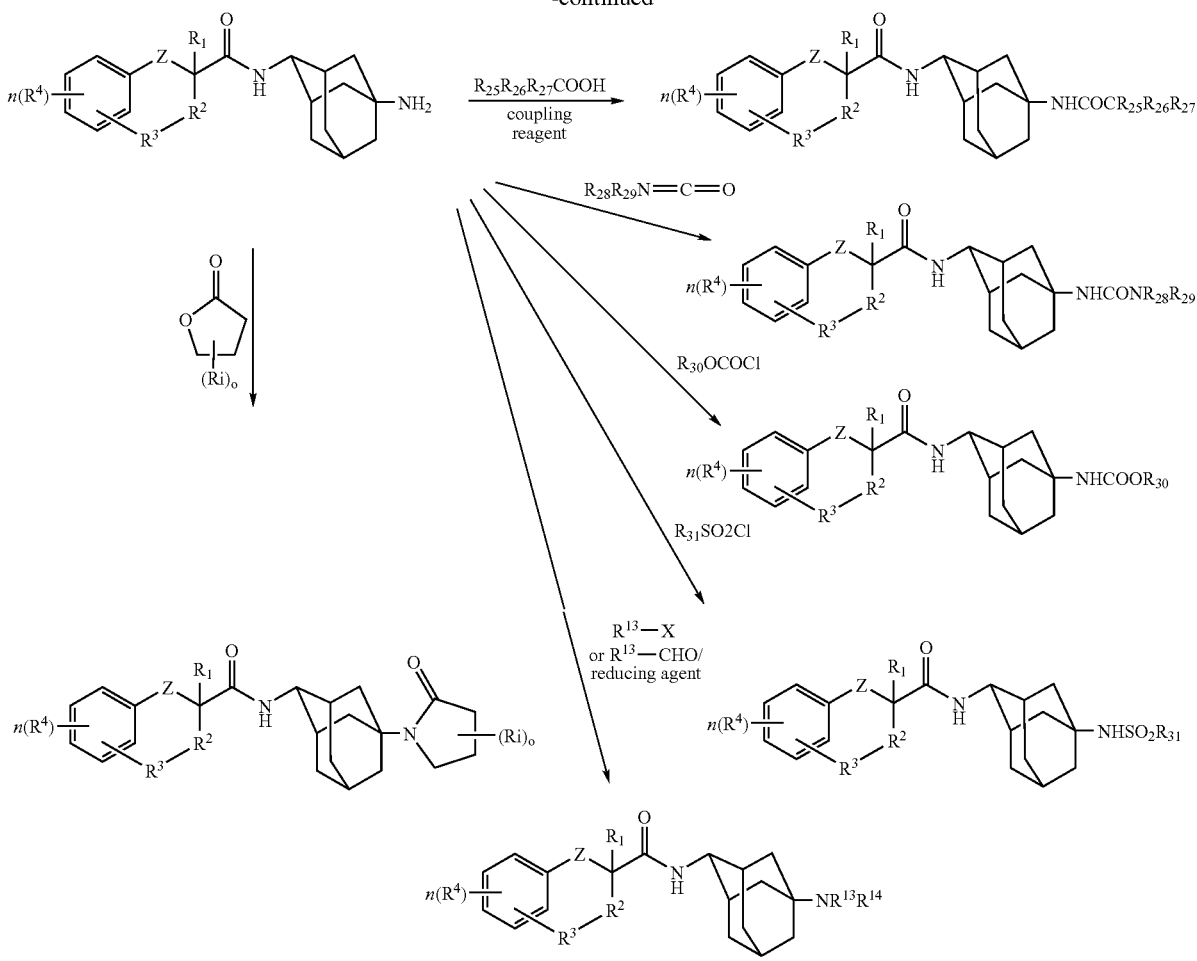

Further examples for the synthesis of compounds of formula (I) using anyone of the above-mentioned synthesis methods, are provided in the experimental part hereinafter.

Where necessary or desired, any one or more of the following further steps in any order may be performed:

(i) removing any remaining protecting group(s);

(ii) converting a compound of formula (I) or a protected form thereof into a further compound of formula (I) or a protected form thereof;

(iii) converting a compound of formula (I) or a protected form thereof into a N-oxide, a salt, a quaternary amine or a solvate of a compound of formula (I) or a protected form thereof;

(iv) converting a N-oxide, a salt, a quaternary amine or a solvate of a compound of formula (I) or a protected form thereof into a compound of formula (I) or a protected form thereof;

(v) converting a N-oxide, a salt, a quaternary amine or a solvate of a compound of formula (I) or a protected form thereof into another N-oxide, a pharmaceutically acceptable addition salt a quarternary amine or a solvate of a compound of formula (I) or a protected form thereof;

(vi) where the compound of formula (I) is obtained as a mixture of (R) and (S) enantiomers resolving the mixture to obtain the desired enantiomer;

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The protection and deprotection of functional groups may take place before or after a reaction step.

The use of protecting groups is fully described in 'Protective Groups in Organic Synthesis' $2^{nd}$ edition, T W Greene & P G M Wutz, Wiley Interscience (1991).

Additionally, the N-atoms in compounds of formula (I) can be methylated by art-known methods using $CH_3$-I in a suitable solvent such as, for example 2-propanone, tetrahydrofuran or dimethylformamide.

The compounds of formula (I), can also be converted into each other following art-known procedures of functional group transformation of which some examples are mentioned hereinabove.

The compounds of formula (I), may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids. e.g. peroxoacetic acid, alkylhydroperoxides, e.g. t-butyl hydroperoxide. Suitable solvents are, for example, water, low alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I), may be obtained by the application of art-known procedures. Diastereomers may be separated by physical methods such as selective crystallization and chromatographic techniques, e.g. counter-current distribution, liquid chromatography and the like.

Some of the compounds of formula (I), and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines, in particular to treat pathologies associated with excess cortisol formation, i.e. disorders where a decreased level of active glucocorticoid is desirable, such as metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. In particular to treat pathologies such as for example, obesity, diabetes, type 2 diabetes, obesity related cardiovascular diseases, stress and glaucoma.

As described in the experimental part hereinafter, the inhibitory effect of the present compounds on the 11β-HSD1-reductase activity (conversion of cortison into cortisol) has been demonstrated in vitro, in an enzymatic assay using the recombinant 11β-HSD1 enzyme, by measuring the conversion of cortison into cortisol using HPLC purification and quantification methods. 11β-HSD1-reductase inhibition was also demonstrated in vitro, in a cell based assay comprising contacting the cells, expressing 11β-HSD1 with the compounds to be tested and assessing the effect of said compounds on the formation of cortisol in the cellular medium of these cells. The cells preferably used in an assay of the present invention are selected from the group consisting of mouse fibroblast 3T3-L1 cells, HepG2 cells, pig kidney cell, in particular LCC-PK1 cells and rat hepatocytes.

Accordingly, the present invention provides the compounds of formula (I) and their pharmaceutically acceptable N-oxides, addition salts, quaternary amines and stereochemically isomeric forms for use in therapy. In particular to treat pathologies associated with excess cortisol formation, i.e. disorders where a decreased level of active glucocorticoid is desirable, such as metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. More particular to treat pathologies such as for example, obesity, diabetes, type 2 diabetes, obesity related cardiovascular diseases, stress and glaucoma. Even more particular in the treatment or prevention of pathologies associated with excess cortisol formation such as obesity, diabetes, obesity related cardiovascular diseases and glaucoma.

In view of the utility of the compounds according to the invention, there is provided a method for the treatment of an animal, for example, a mammal including humans, suffering from a pathology associated with excess cortisol formation, which comprises administering an effective amount of a compound according to the present invention. Said method comprising the systemic or topical administration of an effective amount of a compound according to the invention, to warm-blooded animals, including humans.

It is thus an object of the present invention to provide a compound according to the present invention for use as a medicine. In particular to use the compound according to the present invention in the manufacture of a medicament for treating pathologies associated with excess cortisol formation such as for example, metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma, in particular obesity, diabetes, obesity related cardiovascular diseases, stress and glaucoma.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.001 mg/kg to 500 mg/kg body weight, in particular from 0.005 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compound of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Experimental Part

In the procedures described hereinafter the following abbreviations were used: "DIPE" stands for diisopropylether; "EtOAc" stands for ethyl acetate; "DMF" stands for N,N-dimethylformamide, "TEA" for N,N-diethylethanamine "DMAP" for N,N-dimethyl-4-pyridinamine, "EDCI" stands for 1-(3-dimethylaminopropyl)-3-ethylcarbodiimide, "HOBt" stands for hydroxybenzotriazole, "NMM" stands for 4-methylmorpholine, "DIPCDI" stands for N,N'-diisopropyl-carbodiimide and "DIPEA" stands for N,N-diisopropylethylamine.

Estrelut™ is a product of Merck KgaA (Darmstadt, Germany) and is a short column comprising diatomaceous earth. Supelco is a prepacked silicagel liquid chromatography column.

For some chemicals the chemical formula was used, e.g. $CH_2Cl_2$ for dichloromethane, $CH_3OH$ for methanol, HCl for hydrochloric acid, $H_2SO_4$ for sulfuric acid, and $NaHCO_3$ for sodium hydrogen carbonate.

A. Preparation of the Intermediates

EXAMPLE A.1

Preparation of

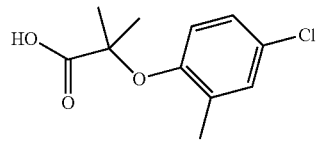

intermediate 1

4-chloro-2-methylphenol [1570-64-5] (0.0049 mol) was stirred in dioxane (15 ml). Sodium hydride (0.0049 mol) was added and the mixture was stirred for 30 minutes. 2-Bromo-2-methylpropanoic acid, 1,1-dimethylethylester [23877-12-5] (0.005 mol) was added and the reaction mixture was stirred overnight at 60° C. Water (5 ml) was added. The mixture was washed with dichloromethane. The layers were separated. The aqueous layer was acidified with HCl, then extracted with dichloromethane. The separated organic layer was washed, filtered through Extrelut, and the filtrate was evaporated. The residue was purified over silica gel (Supelco) on a glass filter (eluent: $CH_2Cl_2$). The product fractions were collected and the solvent was evaporated, yielding 0.145 g of intermediate 1.

EXAMPLE A.2

Preparation of

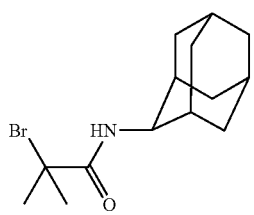

intermediate 2

A mixture of 2-bromo-2-methyl-propanoic acid [2052-01-9] (0.01 mol), N'-(ethylcarbonimidoyl)-N,N-dimethyl-1,3-propanediamine, monohydrochloride [25952-53-8] (0.011 mol) and 1-hydroxy-1H-benzotriazole (0.011 mol) in dichloromethane (50 ml) was stirred for 30 minutes at room temperature, then N,N-diethylethanamine (0.03 mol) was added, followed by tricyclo[3.3.1.1$^{3,7}$]decan-2-amine, hydrochloride [10523-68-9] (0.013 mol). The reaction mixture was stirred for 5 hours at room temperature and then washed with a 15% citric acid solution, with a 5% NaHCO$_3$ solution with water and with brine. After drying, the solvent was evaporated, yielding 2.5 g of intermediate 2.

EXAMPLE A.3 a) Preparation of

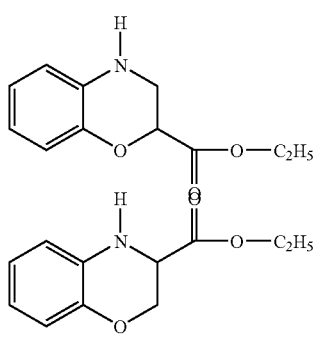

intermediate 3 intermediate 4

2,3-Dibromopropanoic acid, ethyl ester (0.05 mol) was added to a suspension of 2-aminophenol (0.046 mol) and potassium carbonate (0.135 mol) in 2-propanone (250 ml) and then the reaction mixture was stirred and refluxed over the weekend. The mixture was filtered and the filtrate was evaporated, yielding a mixture of intermediate 3 [22244-22-0 and intermediate 4 [177202-60-7].

b) Preparation of

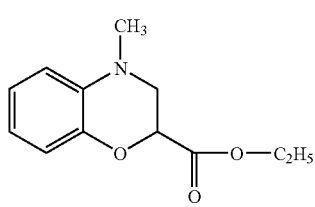

intermediate 5

Potassium carbonate (0.03 mol) and iodomethane (0.03 mol) were added to a solution of a mixture of intermediate 3 and intermediate 4 (0.01 mol) in 2-propanone. The reaction mixture was stirred and refluxed overnight. The resulting precipitate was filtered off, washed with 2-propanone and the filtrate was evaporated. The obtained residue (3.2 g) was dissolved in 2-propanol (50 ml) and in DIPE (50 ml). Then the solution was washed with water and with brine and concentrated again, yielding 1.9 g of intermediate 5 [54442-28-3].

c) Preparation of

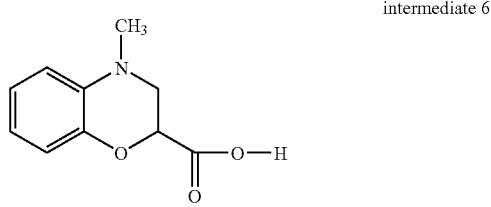

intermediate 6

A solution of intermediate 5 [54442-28-3] (0.0086 mol) in hydrochloric acid and 2-propanol was stirred and refluxed for 3 hours. Then the reaction mixture was cooled and diluted with ice-water. Potassium hydroxide was added until pH 8 and the mixture was extracted with EtOAC and with dichloromethane. The aqueous layer was acidified with HCl and extracted with dichloromethane. The extracts were combined, washed with brine and concentrated, yielding intermediate 6 [212578-38-6].

EXAMPLE A.4

Preparation of

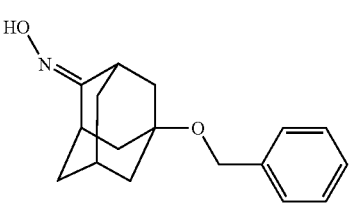

intermediate 7

5-(Phenylmethoxy)-tricyclo[3.3.1.1$^{3,7}$]decanone[167856-60-2] (1.5 g) was dissolved in ethanol (25 ml). Hydroxyamine.hydrochloride (0.9 g) was added followed by 2N KOH (10 ml). The mixture was stirred overnight. The volatiles were removed by evaporation, and the residue was extracted with dichloromethane. The organic layer was washed with brine, dried (MgSO4) and evaporated, yielding 1.4 g of intermediate 7.

b) Preparation of

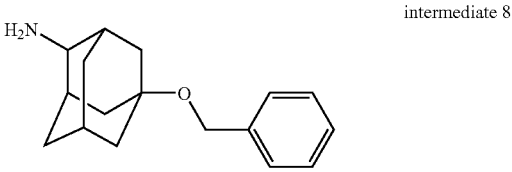 [SMILES: NC1C2CC3CC1CC(OCc1ccccc1)(C3)C2]

intermediate 8

Intermediate 7 was dissolved in 7M NH$_3$/MeOH (40 ml), Raney Nickel (0.5 g) was added, and the mixture was hydrogenated at 14° C. The mixture was filtered, and evaporated, yielding 1.3 g of intermediate 8 as a 1 to 1 mixture of its cis and trans isomers.

B. Preparation of the Compounds

EXAMPLE B.1

Preparation of

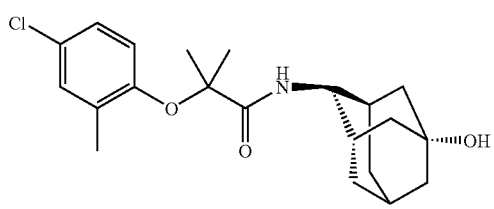

compound 1

1-Hydroxy-1H-benzotriazole (0.0007 mol) was added to a solution of intermediate 1 (0.0006 mol) in dichloromethane (10 ml) and DMF (5 ml) and the mixture was stirred for 10 minutes. Then N'-(ethylcarbonimidoyl)-N,N-dimethyl-1,3-propanediamine, monohydrochloride [25952-53-8] (0.0007 mol) was added and the mixture was stirred for 20 minutes. After addition of $(1\alpha,3\alpha,4\alpha,5\beta,7\alpha)$-4-aminotricyclo$[3.3.1.1^{3,7}]$decan-1-ol [62058-03-1] (0.0007 mol), the reaction mixture was stirred overnight and the solvent was evaporated. The obtained residue was dissolved in dichloromethane and then washed with a 15% citric acid solution and with a $Na_2CO_3$ solution. The organic layer was dried through Extrelut and the solvent was evaporated, yielding 0.170 g of compound 1.

EXAMPLE B.2

Preparation of

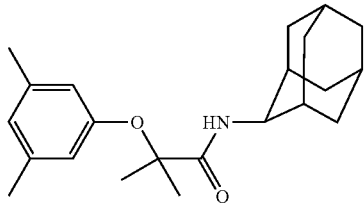

compound 2

Sodium hydride (60%) (0.0009 mol) was added to a stirred solution of 3,5-dimethylphenol (0.00098 mol) in dioxane (5 ml). The mixture was stirred for 45 minutes before intermediate 2 (0.0011 mol) was added. The reaction mixture was stirred for 4 hours at 90° C., then overnight at room temperature. Water (2 ml) was added and the mixture was extracted with dichloromethane. The organic layer was separated, dried, filtered off and the solvent was evaporated. The residue was purified by column chromatography over silica gel (Supelco) (eluent: $CH_2Cl_2/CH_3OH$ 98/2). The product fractions were collected and the solvent was evaporated. The residue was dissolved in dichloromethane and washed 2 times with a potassium hydroxide solution. The organic layer was separated, dried, filtered off and the solvent was evaporated, yielding 0.175 g of compound 2.

EXAMPLE B.3

Preparation of

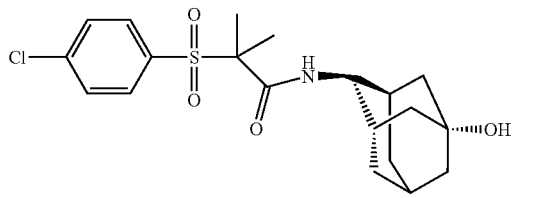

compound 3

A mixture of 2-[(p-chlorophenyl)sulfonyl]-2-methylpropionic acid [28361-38-3] (0.00028 mol) in dichloromethane (5 ml) and DMF (5 ml) was stirred and 1-hydroxy-1H-benzotriazole (0.00033 mol) was added. Then the mixture was stirred for 10 minutes and N'-(ethylcarbonimidoyl)-N,N-dimethyl-1,3-propanediamine, monohydrochloride [25952-53-8] (0.00033 mol) was added. The resulting mixture was stirred for 10 minutes and $(1\alpha,3\alpha,4\alpha,5\beta,7\alpha)$-4-aminotricyclo$[3.3.1.1^{3,7}]$decan-1-ol [62058-03-1] (0.00033 mol) was added. The reaction mixture was stirred overnight at room temperature and then the solvent was evaporated. The residue was purified by column chromatography over silica gel (eluent: $CH_2Cl_2/CH_3OH$ 98/2). The product fractions were collected and the solvent was evaporated, yielding 0.094 g of compound 3.

EXAMPLE B.4

Preparation of

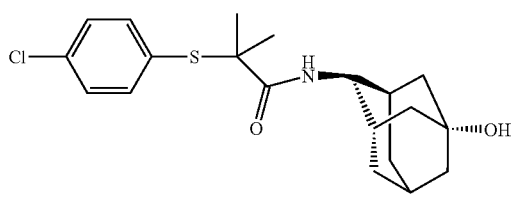

compound 4

A mixture of 2-[(4-chlorophenyl)thio]-2-methylpropanoic acid [17413-74-0] (0.0007 mol) in dichloromethane (5 ml), DMF (5 ml) and DIPEA (0.5 ml) was stirred and 1-[bis(dimethylamino)methylene]-1H-benzotriazolium, hexafluorophosphate(1-), 3-oxide (HBTU) (0.0075 mol) was added. After stirring for 15 minutes $(1\alpha,3\alpha,4\alpha,5\beta,7\alpha)$-4-aminotricyclo$[3.3.1.1^{3,7}]$decan-1-ol [62058-03-1] (0.00075 mol) was added. The reaction mixture was stirred overnight at 40° C. and the solvent was evaporated. The residue was dissolved in dichloromethane and then the solution was washed with a 15% citric acid solution and with a sodium carbonate solution. The organic layer was separated, dried, filtered off and the solvent was evaporated. The obtained residue was purified by column chromatography over silica gel (Supelco) (eluent: dichloromethane). The product fractions were collected and the solvent was evaporated, yielding 0.164 g of compound 4.

b) Preparation of

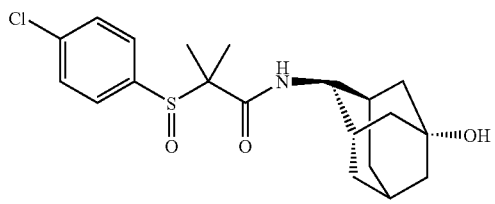
compound 5

A mixture of compound 4 ((0.00043 mol) in dichloromethane (15 ml) was stirred at −50° C. and 3-chlorobenzenecarboperoxoic acid (0.0005 mol) was added. The reaction mixture was stirred overnight at room temperature and washed with a sodium carbonate solution. The organic layer was dried by filtration through Extrelut and the solvent was evaporated, yielding 0.13 g of compound 5.

EXAMPLE B.5

Preparation of

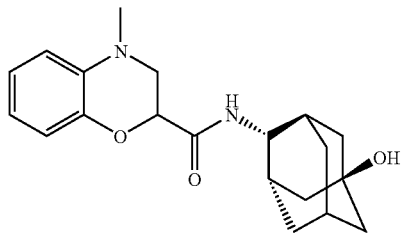
compound 6

N'-(ethylcarbonimidoyl)-N,N-dimethyl-1,3-propanediamine, monohydrochloride [25952-53-8] (0.0022 mol) and 1-hydroxy-1H-benzotriazole (0.0022 mol) were added to a solution of intermediate 6 [212578-38-6] (0.002 mol) in DMF (25 ml) and the mixture was stirred and warmed (40° C.). Then a solution of 4-amino-(1α,3α,4α,5β,7α)tricyclo[3.3.1.1$^{3,7}$]decan-1-ol [62058-03-1] (0.0024 mol) in hot DMF was added and the reaction mixture was stirred overnight at room temperature. The mixture was poured out into ice-water and was extracted with EtOAc. The obtained extract was washed with water and with brine and then dried and concentrated, yielding 0.040 g of compound 6.

EXAMPLE B.6

Preparation of

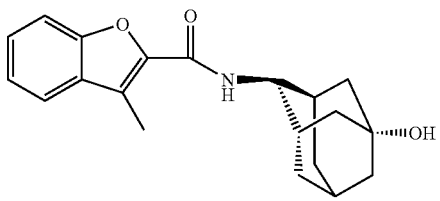
compound 7

1-Hydroxy-1H-benzotriazole (0.001 mol) was added to a stirred mixture of 3-methylbenzofurancarboxylic acid [24673-56-1] (0.0009 mol) in dichloromethane (5 ml) and DMF (5 ml). The mixture was stirred for 10 minutes and N'-(ethyl-carbonimidoyl)-N,N-dimethyl-1,3-propanediamine, monohydrochloride [25952-53-8] (0.001 mol) was added. The resulting mixture was stirred for 1 hour before (1α,3α,4α,5β,7α)-4-aminotricyclo[3.3.1.1$^{3,7}$]decan-1-ol [62058-03-1] (0.001 mol) was added. The reaction mixture was stirred at room temperature overnight and then (Polystyrylmethyl)-trimethylammonium bicarbonate (1 g; Novabiochem Cat. No.: 01-64-0419) and Methylisocyanate polystyrene (1 g; Novabiochem Cat. No.: 01-64-0169) were added. The resulting mixture was shaken for 1 hour and filtered. The filtrate was evaporated and the obtained residue was purified by flash column chromatography (eluent: $CH_2Cl_2/CH_3OH$ 90/10). The product fractions were collected and the solvent was evaporated, yielding 0.144 g of compound 7.

EXAMPLE B.7

Preparation of

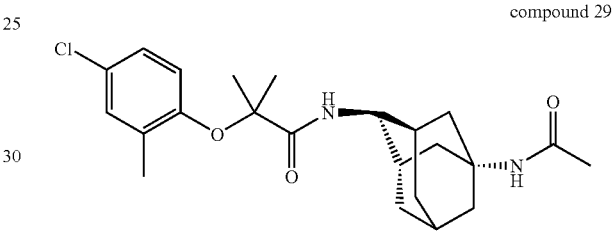
compound 29

A mixture of compound (1) ( ) (0.00026 mol) and acetonitrile (2 ml) was stirred. $H_2SO_4$ (0.05 ml) was added dropwise and the reaction mixture was stirred overnight. The mixture was poured out on ice. The mixture was neutralized with a $Na_2CO_3$ solution. The mixture was extracted with $CH_2Cl_2$. The organic layer was separated, dried, filtered and the solvent was evaporated. The residue was purified by column chromatography over silica gel (Supelco) (eluent: $CH_2Cl_2/CH_3OH$ 98/2). The product fractions were collected and the solvent was evaporated, yielding 0.057 g of compound 29.

EXAMPLE B.8

Preparation of

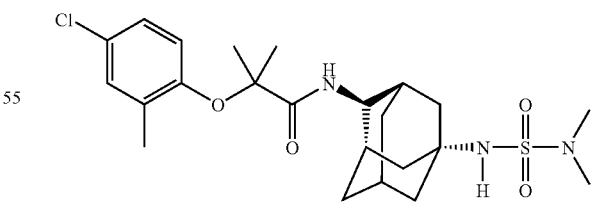
compound 30

A mixture of compound 32 ( ) (0.1 g), $CH_2Cl_2$ (10 ml) and TEA (2 ml) was stirred. N,N-dimethylaminosulfonyl chloride (0.15 ml) was added dropwise. The reaction mixture was stirred overnight. DMAP (cat. quant.) was added and the mixture was stirred at 45° C. overnight. The mixture was cooled washed with a 15% citric acid solution. The organic layer was separated, dried, filtered and the solvent was evaporated. The residue was purified by column chromatography over silica gel (Supelco) (eluent: CH$_2$Cl$_2$/CH$_3$OH 99/1). The product fractions were collected and the solvent was evaporated, yielding 0.046 g of compound 30.

EXAMPLE B.9 a) Preparation of compound 31

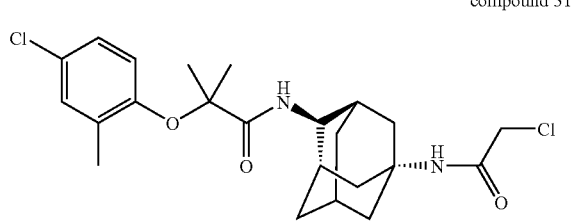

A mixture of compound (1) ( ) (0.005 mol) and chloroacetonitrile (5 ml) was stirred. H$_2$SO$_4$ (0.5 ml) was added and the mixture was stirred over weekend. H$_2$SO$_4$ (0.5 ml) was added and the mixture was stirred overnight. The mixture was poured out on ice. The mixture was neutralized with a Na$_2$CO$_3$ solution. The mixture was extracted with CH$_2$Cl$_2$. The organic layer was separated, dried, filtered and the solvent was evaporated. The residue was crystallized from DIPE. The precipitate was filtered off and dried, yielding 1.9 g (84%) of compound 31.

b) Preparation of compound 32

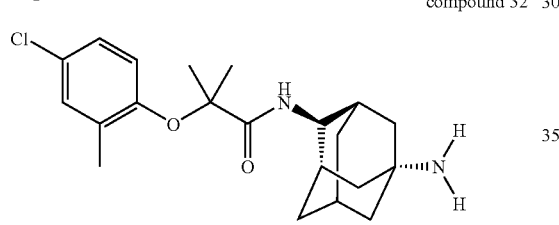

A mixture of compound 31 ( ) (0.0042 mol), thiourea (0.006 mol), ethanol (20 ml) and acetic acid (4 ml) was stirred and refluxed overnight. The mixture was poured out into water. The mixture was neutralized with a Na$_2$CO$_3$ solution. The mixture was extracted with CH$_2$Cl$_2$. The organic layer was separated, dried, filtered and the solvent was evaporated. The residue was crystallized from DIPE. The precipitate was filtered off and dried, yielding 1 g (63.6%) of compound 32.

EXAMPLE B.10

Preparation of compound 33

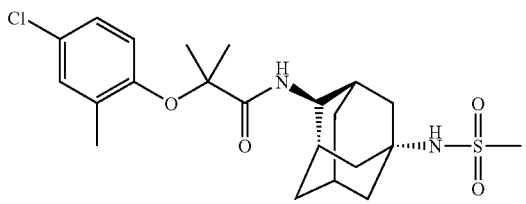

A mixture of compound 32) (0.00026 mol), CH$_2$Cl$_2$ (10 ml) and TEA (1 ml) was stirred. Methanesulfonyl chloride (0.0006 mol) was added dropwise. The reaction mixture was stirred overnight. DMAP (cat. quant.) was added. The mixture was washed with water. The organic layer was separated, dried, filtered and the solvent was evaporated. The residue was purified by high-performance liquid chromatography. The product fractions were collected and the solvent was evaporated, yielding 0.027 g of compound 33.

EXAMPLE B.11

Preparation of compound 34

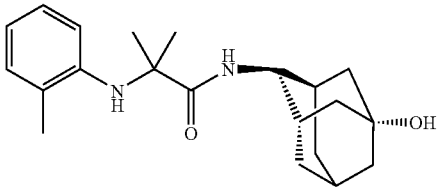

To a mixture of 2-methyl-N-o-tolyl-alanine [117755-95-0] (0.006 mol), EDCI (0.009 mol), HOBt (0.009 mol), NMM (0.024 mol) and CH$_2$Cl$_2$ (80 ml), a solution of (1α,3α,4α,5β,7α)-4-amino-tricyclo[3.3.1.1$^{3,7}$]decan-1-ol [62058-03-1] (0.006 mol) in DMF (20 ml) was added after 10 minutes. The reaction mixture was stirred for 16 hours at 20° C. under N$_2$ flows. The mixture was poured out into a column comprising diatomaceous earth. Then the column was washed with CH$_3$OH/CH$_2$Cl$_2$ 5/95. The filtrate was purified by flash chromatography (eluent: CH$_3$OH(2-3%)/CH$_2$Cl$_2$) over SiO$_2$, yielding 0.89 g (44%) of compound 34

EXAMPLE B.12

Preparation of compound 35

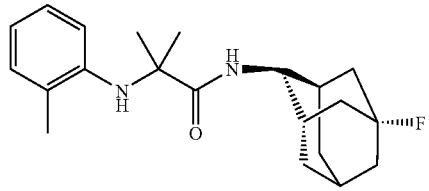

Compound 34 (0.009 mol) was dissolved in CH$_2$Cl$_2$ (30 ml). The mixture was cooled to −70° C. under N$_2$ flow. (N-ethylethanaminato)trifluoro-sulfur [38078-09-0] (0.002 mol) was added. The reaction mixture was stirred at −70° C. for 2 hours. The mixture was washed with a saturated aqueous NaHCO$_3$ solution (30 ml) and dried (MgSO$_4$). The solvent was evaporated. The residue was filtered through silica gel. The precipitate was treated with diethyl ether, yielding 0.200 g of compound 35.

EXAMPLE B.13 a) Preparation of compound 36

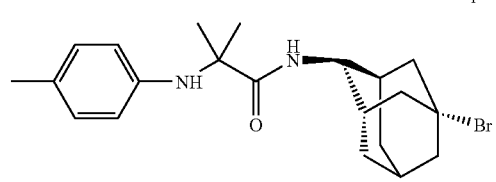

A mixture of compound 27 ((0.00146 mol) and hydrobromic acid (48%) (15 ml) was heated to 80° C. overnight. The reaction mixture was evaporated to dryness under reduced pressure. The reaction was repeated, yielding compound 36 (crude).

b) Preparation of compound 37

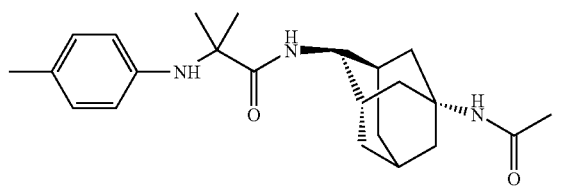

A mixture of compound 36 (crude) and acetamide (q.s.) was heated to 130° C. for 48 hours. The mixture was diluted with water, stirred for 30 minutes and then extracted with $CH_2Cl_2$. The organic layer was separated, dried ($Na_2SO_4$) and the solvent was evaporated under reduced pressure. The residue (still starting material A) was dissolved in $CH_3CN$. Acetamide (q.s.) was added. The reaction mixture was heated for 4 hours at 170° C. in a sealed tube in the microwave. The mixture was poured out into water. The mixture was stirred for 30 minutes and then extracted with $CH_2Cl_2$. The organic layer was separated, dried ($Na_2SO_4$) and the solvent was evaporated. The residue was purified by column chromatography (eluent: hexane/EtOAc 50/50 to 0/100). The product fractions were collected and the solvent was evaporated, yielding 0.07 g of compound 37.

EXAMPLE B.14

Preparation of compound 38

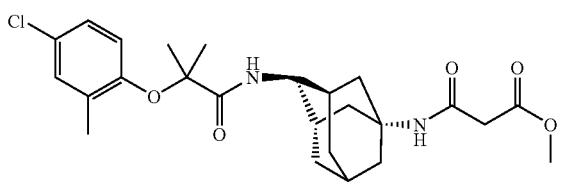

A mixture of compound (1) ( ) (0.00026 mol) and cyanoacetic acid, methyl ester (2 ml) was stirred. $H_2SO_4$ (0.05 ml) was added dropwise and the reaction mixture was stirred overnight. The mixture was poured out on ice. The mixture was neutralized with a $Na_2CO_3$ solution. The mixture was extracted with $CH_2Cl_2$. The organic layer was separated, dried, filtered and the solvent was evaporated. The residue was purified by column chromatography over silica gel (Supelco) (eluent: $CH_2Cl_2/CH_3OH$ 98/2). The product fractions were collected and the solvent was evaporated, yielding 0.066 g of compound 38.

EXAMPLE B.15

Preparation of compound 39

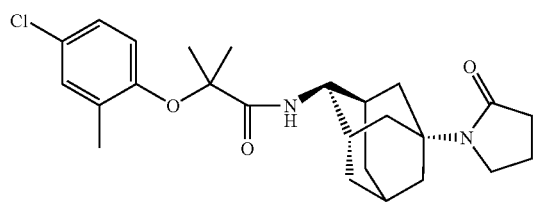

A mixture of compound 32) (0.00013 mol) and dihydro-2 (3H)-furanone (1.5 ml) was stirred in a microwave at 240° C. for 5000 sec. The mixture was cooled. The solvent was evaporated. The residue was purified by column chromatography over silica gel (Supelco) (eluent: $CH_2Cl_2/CH_3OH$ 100/0 to 0/100). The product fractions were collected and the solvent was evaporated. The residue was purified by column chromatography over silica gel (Supelco) (eluent: $CH_2Cl_2/CH_3OH$ 98/2). The product fractions were collected and the solvent was evaporated, yielding 0.108 g (45%) of compound 39.

EXAMPLE B.16 a) Preparation of compound 13

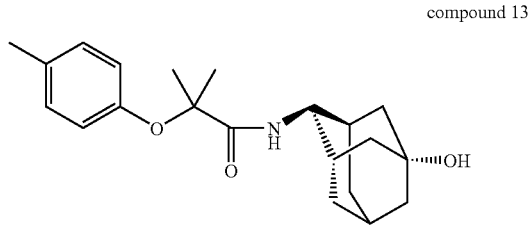 [SMILES: Cc1ccc(OC(C)(C)C(=O)N[C@H]2[C@@H]3CC4C[C@H]2C[C@](O)(C4)C3)cc1]

To a mixture of 2-methyl-2-(4-methylphenoxy)propanoic acid [23438-11-1] (0.015 mol) and DME (100 ml), HOBt (0.0165 mol) was added at room temperature. The reaction mixture was stirred until complete dissolution. EDCI (0.0165 mol) was added and the mixture was stirred at room temperature for 30 minutes. (1α,3α,4α,5β,7α)-4-amino-tricyclo[3.3.1.1$^{3,7}$]decan-1-ol [62058-03-1] (0.0165 mol) was added and the mixture was stirred at room temperature for 3 hours. The solvent was evaporated. The residue was purified by column chromatography (eluent: $CH_2Cl_2/CH_3OH$ 100/0 to 98/2). The product fractions were collected and the solvent was evaporated, yielding 0.290 g (54%) of compound 13 b) Preparation of compound 40

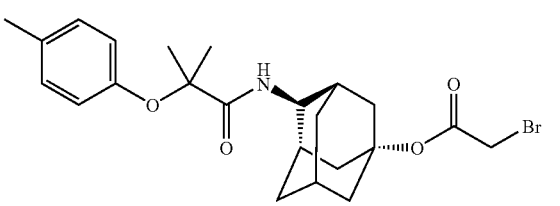

To a mixture of compound 13 (0.00466 mol) and bromoacetic acid (0.00513 mol) in $CH_2Cl_2$ (15 ml) at 5° C., DMAP (0.200 g) was added. A solution of DIPCDI (0.00606 mol) in $CH_2Cl_2$ (3 ml) was added dropwise. The reaction mixture was stirred until the temperature reached room temperature. Extra bromoacetic acid (0.00513 mol), DMAP (0.200 g) and DIPCDI (0.00606 mol) were added at 5° C. The reaction mixture was stirred for 2 hours until the temperature reached room temperature. The mixture was filtered. The precipitate was purified by high-performance liquid chromatography (eluent: $CH_2Cl_2/CH_3OH$ 100/0 to 98.4/1.6). The product fractions were collected and the solvent was evaporated. The residue was purified again by high-performance liquid chromatography (eluent: $CH_2Cl_2/CH_3OH$ 100/0 to 98.4/1.6). The product fractions were collected and the solvent was evaporated, yielding 0.842 g (37%) of compound 40.

c) Preparation of

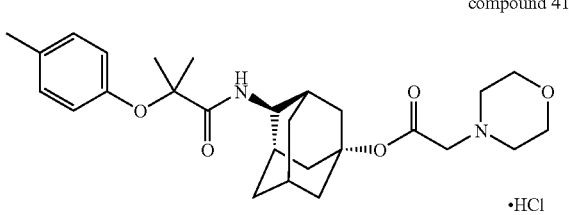
compound 41
·HCl

A mixture of compound 40 (0.00174 mol), morpholine (0.00209 mol), potassium carbonate (0.00348 mol), acetonitrile (20 ml) and potassium iodide (cat. quant.) was stirred at 50° C. for 2 hours. The solvent was evaporated. The residue was dissolved in CH$_2$Cl$_2$ and washed with water. The organic layer was separated, dried (MgSO$_4$), filtered and the solvent was evaporated. The residue was crystallized from 2-propanol and DIPE. The precipitate was filtered off, washed with 2-propanol and dried, yielding 0.290 g (33%) of compound 41.

EXAMPLE B.17

Preparation of

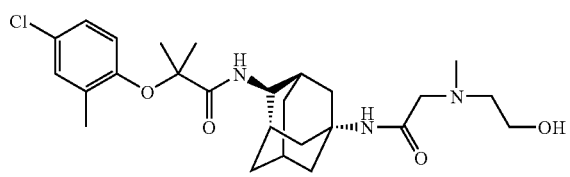
compound 42

A mixture of compound 31 (0.00022 mol), acetonitrile (10 ml) and sodium carbonate (0.06 g) was stirred. 2-(Methylamino)ethanol [109-83-1] (0.0003 mol) was added. The reaction mixture was stirred overnight. The solvent was evaporated. The residue was purified by column chromatography over silica gel (Supelco) (eluent: CH$_2$Cl$_2$/CH$_3$OH 98/2). The product fractions were collected and the solvent was evaporated, yielding 0.031 g of compound 42.

EXAMPLE B.18 a) Preparation of

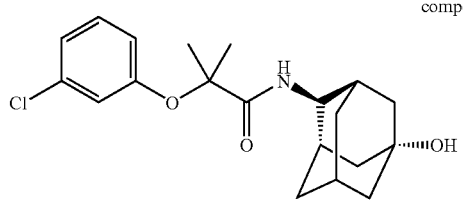
compound 43

To a mixture of 2-(3-chlorophenoxy)-2-methyl-propanoic acid [17413-73-9] (0.010 mol) and CH$_2$Cl$_2$ (70 ml), HOBt (0.012 mol) was added at room temperature. The mixture was stirred until complete dissolution of HOBt. EDCI (0.012 mol) was added and the mixture was stirred at room temperature for 30 minutes. (1α,3α,4α,5β,7α)-4-aminotricyclo[3.3.1.1$^{3,7}$]decan-1-ol [62058-03-1] (0.012 mol) was added and the mixture was stirred at room temperature overnight. The solvent was evaporated. The residue was dissolved in CH$_2$Cl$_2$ and washed with 15% citric acid solution, 1M Na$_2$CO$_3$ and water. The organic layer was separated, dried (MgSO$_4$), filtered and the solvent was evaporated. The residue was purified by column chromatography (eluent: CH$_2$Cl$_2$/CH$_3$OH 100/0 to 98/2). Two product fraction groups were collected and the solvents were evaporated. The residue was crystallized from DIPE. The precipitate was filtered off and dried, yielding 1.97 g of compound 43.

b) Preparation of

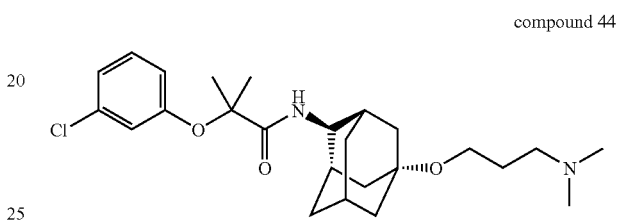
compound 44

To a mixture of compound 43 (0.00055 mol) and 3-chloro-N,N-dimethyl-1-propanamine, hydrochloride [5407-04-5] (0.000826 mol) in DMF (8 ml) and toluene (2 ml), a dispersion of sodium hydride in mineral oil (60%) (0.0165 mol) was added in 4 portions over 90 minutes. The reaction mixture was stirred at 70° C. for 24 hours. The solvent was evaporated. Water was added. The mixture was extracted with CH$_2$Cl$_2$. The organic layer was separated, dried (MgSO$_4$), filtered and the solvent was evaporated. The residue was purified by high-performance liquid chromatography. The product fractions were collected and the solvent was evaporated, yielding 0.038 g (15%) of compound 44.

EXAMPLE B.19

Preparation of

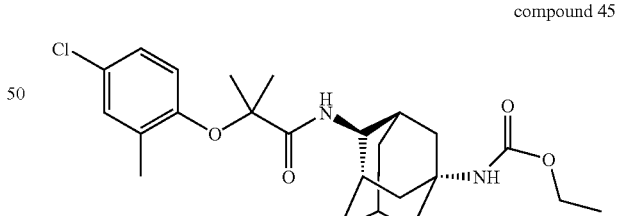
compound 45

A mixture of compound 32) (0.00026 mol), CH$_2$Cl$_2$ (3 ml) and sodium carbonate (0.1 g) was stirred. Carbonochloridic acid, ethyl ester [541-41-3] (0.001 mol) was added dropwise. The reaction mixture was stirred over weekend. The mixture was washed with water. The mixture was filtered through Extrelut and the filtrate was evaporated. The residue was purified by chromatography over silica gel (Supelco) (eluent: CH$_2$Cl$_2$/CH$_3$OH 98/2). The product fractions were collected and the solvent was evaporated, yielding 0.1 g of compound 45.

EXAMPLE B.20

Preparation of

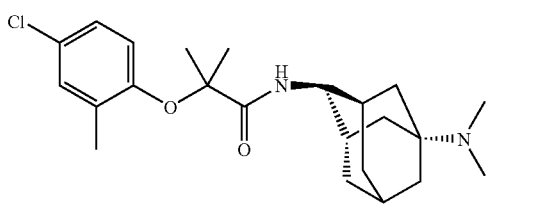
compound 46

A mixture of compound 32) (0.1 g), paraformaldehyde (0.1 g), platinum on activated carbon (5%) (0.010 g), thiophene (0.1 ml), methanol (40 ml) and hydrogen (1 equivalent) was stirred at 50° C. overnight. The mixture was filtered and the filtrate was evaporated. The residue was suspended in $CH_2Cl_2$ and washed with water. The mixture was filtered through Extrelut filter and the filtrate was evaporated. The residue was purified by high-performance liquid chromatography. The product fractions were collected and the solvent was evaporated, yielding 0.038 g of compound 46.

EXAMPLE B.21

Preparation of

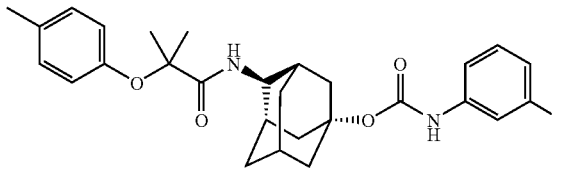
compound 47

A mixture of compound 13 ( ) (0.00058 mol), 1-isocyanato-4-methyl-benzene [622-58-2] (0.000758 mol), chlorotrimethylsilane [75-77-4] (0.000058 mol) and 1,2-dichloroethane (5 ml) was stirred overnight at 50° C. The solvent was evaporated. The residue was purified by column chromatography (Supelco). The product fractions were collected and the solvent was evaporated, yielding 0.045 g (16%) of compound 47.

EXAMPLE B.22

Preparation of

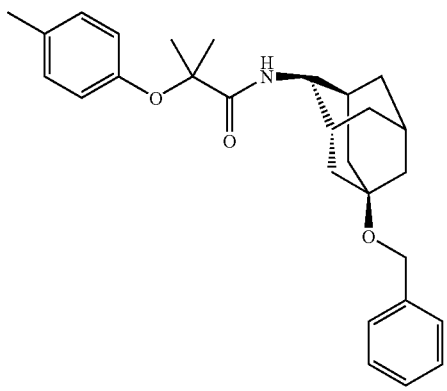
compound 48

-continued

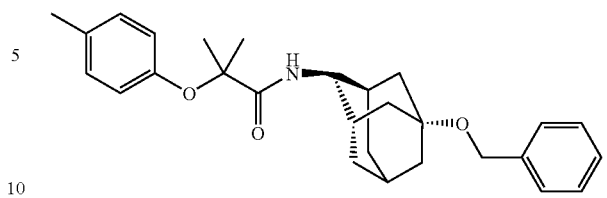
compound 52

A mixture of 2-methyl-2-(4-methylphenoxy)propanoic acid [23438-11-1] (0.004 mol), $CH_2Cl_2$ (25 ml) and DMF (7 ml) was stirred. HOBt (0.004 mol) was added and the mixture was stirred until dissolution. EDCI (0.004 mol) was added and the mixture was stirred for 30 minutes. A solution of intermediate 8 (0.0027 mol) in $CH_2Cl_2$ (25 ml) and DMF (7 ml) was added dropwise. The reaction mixture was stirred overnight. The solvent was evaporated. The residue was dissolved in $CH_2Cl_2$ and washed with a $Na_2CO_3$ solution. The organic layer was separated, dried, filtered and the solvent was evaporated. The residue was purified by column chromatography over silica gel (Biotage) (eluent: $CH_2Cl_2$/hexane/EtOAc 50/48/2). Two product fraction groups were collected and their solvents were evaporated. The residue was purified by high-performance liquid chromatography. The product fractions were collected and the solvent was evaporated, yielding 0.4 g of compound 48 and 0.175 g of compound 52.

EXAMPLE B.23

Preparation of

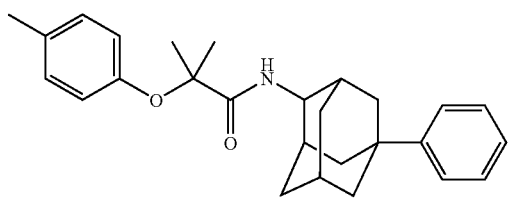
compound 49

A mixture of 2-methyl-2-(4-methylphenoxy)propanoic acid [23438-11-1] (0.004 mol), $CH_2Cl_2$ (25 ml) and DMF (7 ml) was stirred. HOBt (0.004 mol) was added and the mixture was stirred until dissolution. EDCI (0.004 mol) was added and the mixture was stirred for 3 minutes. A solution of 5-phenyl-tricyclo[3.3.1.1$^{3,7}$]decan-2-amine [733695-05-1] (0.0035 mol) in $CH_2Cl_2$ (25 ml) and DMF (7 ml) was added dropwise. The reaction mixture was stirred overnight. The solvent was evaporated. The residue was dissolved in $CH_2Cl_2$ and washed with a $Na_2CO_3$ solution. The organic layer was separated, dried, filtered and the solvent was evaporated. The residue was purified by column chromatography over silica gel (eluent: $CH_2Cl_2$/EtOAc 98/2). The product fractions were collected and the solvent was evaporated. The residue was crystallized from DIPE. The precipitate was filtered off and dried, yielding of compound 49.

EXAMPLE B.24

Preparation of

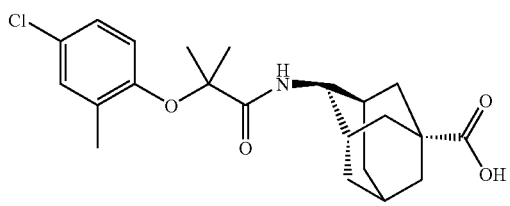

compound 50

$H_2SO_4$ (30 ml) was stirred on ice. A solution of compound (1) (0.00265 mol) in formic acid (30 ml) was added dropwise. The reaction mixture was stirred for 5 days. Then the mixture was stirred at 60° C. for 3 days. Extra $H_2SO_4$ (10 ml) was added at 60° C. The mixture was poured out on ice. The mixture was extracted with $CH_2Cl_2$. The organic layer was separated, washed twice with water, dried, filtered and the solvent was evaporated, yielding 0.8 g of compound 50.

b) Preparation of

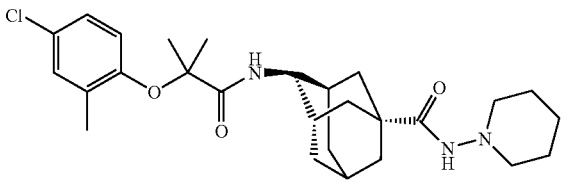

compound 51

A mixture of compound 50 (0.00024 mol), $CH_2Cl_2$ (5 ml) and DMF (2 ml) was stirred. HOBt (0.00025 mol) was added. EDCI (0.00025 mol) was added and the mixture was stirred for 1 hour. 1-Piperidinamine (0.00025 mol) was added and the mixture was stirred overnight. The mixture was poured out into water. The mixture was extracted with $CH_2Cl_2$. The organic layer was separated, washed, dried, filtered and the solvent was evaporated. The residue was purified by column chromatography over silica gel (eluent: $CH_2Cl_2/CH_3OH$ 98/2). The product fractions were collected and the solvent was evaporated. The residue was purified by high-performance liquid chromatography. The product fractions were collected and the solvent was evaporated, yielding 0.051 g of compound 51.

Table F-1 lists the compounds that were prepared according to one of the above Examples.

TABLE F-1

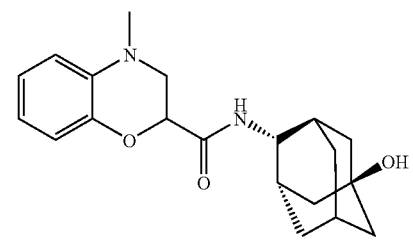 [SMILES: CN1CC(C(=O)N[C@@H]2[C@@H]3CC4C[C@H]2C[C@@](O)(C4)C3)Oc2ccccc21]

Co. No. 6; Ex. B.5

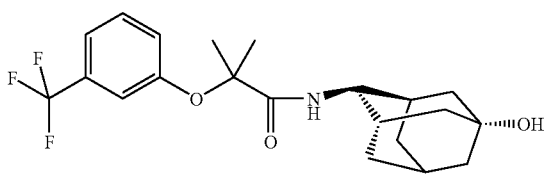 [SMILES: CC(C)(Oc1cccc(C(F)(F)F)c1)C(=O)N[C@H]1[C@@H]2CC3C[C@H]1C[C@](O)(C3)C2]

Co. No. 20; Ex. B.2

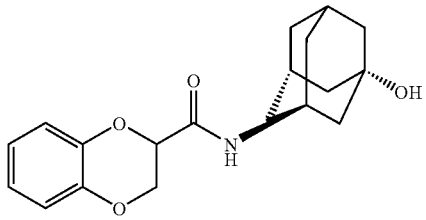 [SMILES: O=C(N[C@H]1[C@@H]2CC3C[C@H]1C[C@](O)(C3)C2)C1COc2ccccc2O1]

Co. No. 8; Ex. B.5

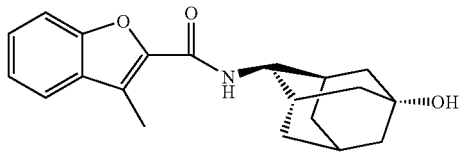 [SMILES: Cc1c(C(=O)N[C@H]2[C@@H]3CC4C[C@H]2C[C@](O)(C4)C3)oc2ccccc12]

Co. No. 7; Ex. B.6

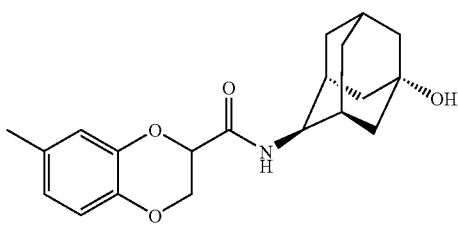

Co. No. 9; Ex. B.5

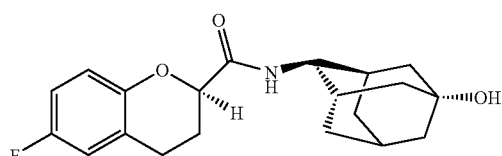

Co. No. 21; Ex. B.6

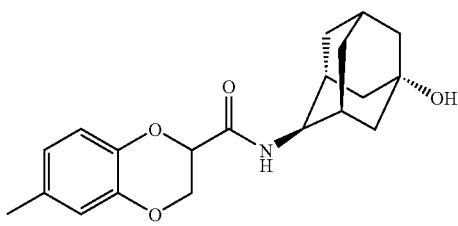

Co. No. 9; Ex. B.5

TABLE F-1-continued
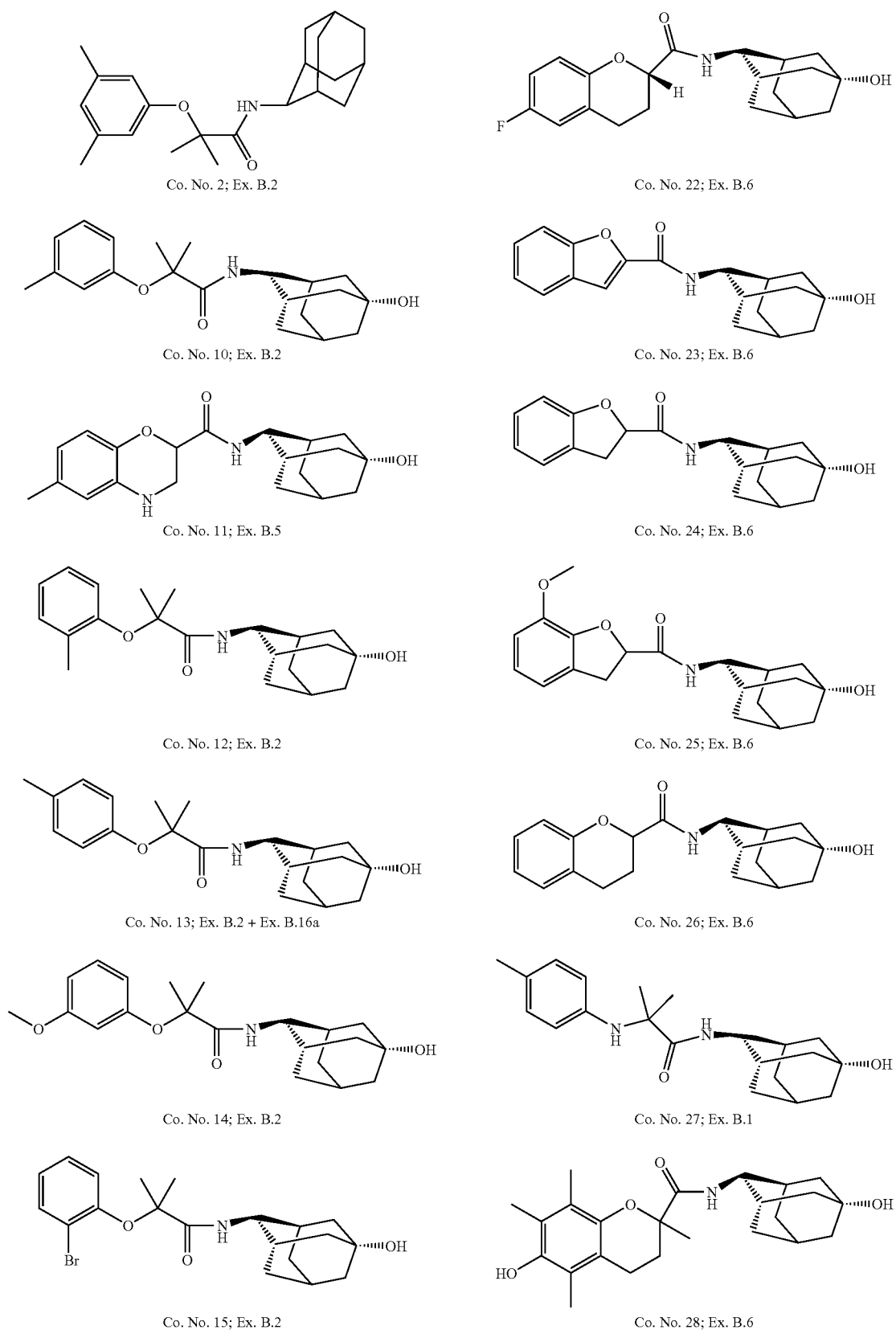

TABLE F-1-continued
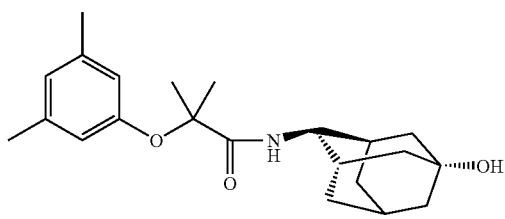 [SMILES: Cc1cc(C)cc(OC(C)(C)C(=O)N[C@H]2[C@@H]3CC4C[C@H]2C[C@](O)(C4)C3)c1]
Co. No. 16; Ex. B.2
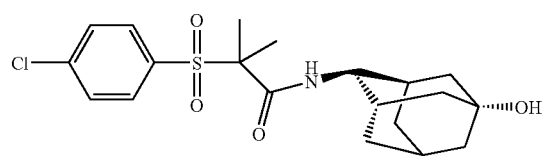 [SMILES: CC(C)(C(=O)N[C@H]1[C@@H]2CC3C[C@H]1C[C@](O)(C3)C2)S(=O)(=O)c1ccc(Cl)cc1]
Co. No. 3; Ex. B.3
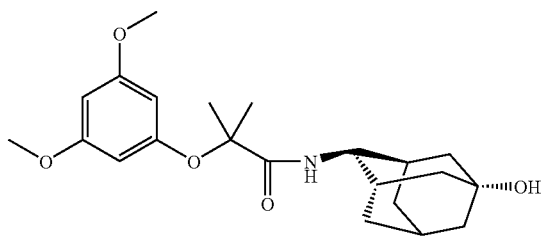 [SMILES: COc1cc(OC)cc(OC(C)(C)C(=O)N[C@H]2[C@@H]3CC4C[C@H]2C[C@](O)(C4)C3)c1]
Co. No. 17; Ex. B.2
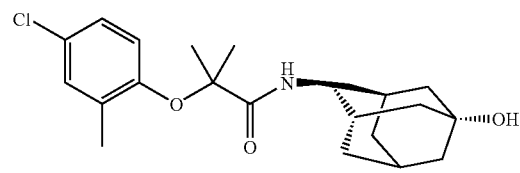 [SMILES: Cc1cc(Cl)ccc1OC(C)(C)C(=O)N[C@H]1[C@@H]2CC3C[C@H]1C[C@](O)(C3)C2]
Co. No. 1; Ex. B.1
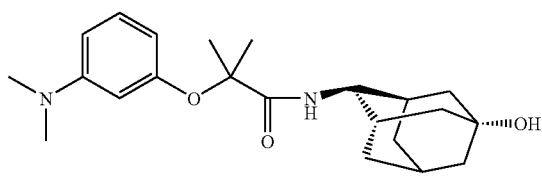 [SMILES: CN(C)c1cccc(OC(C)(C)C(=O)N[C@H]2[C@@H]3CC4C[C@H]2C[C@](O)(C4)C3)c1]
Co. No. 18; Ex. B.2
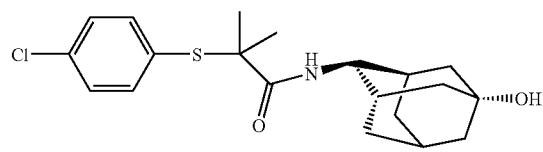 [SMILES: CC(C)(Sc1ccc(Cl)cc1)C(=O)N[C@H]1[C@@H]2CC3C[C@H]1C[C@](O)(C3)C2]
Co. No. 4; Ex. B.4a
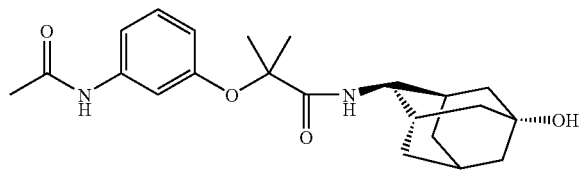 [SMILES: CC(=O)Nc1cccc(OC(C)(C)C(=O)N[C@H]2[C@@H]3CC4C[C@H]2C[C@](O)(C4)C3)c1]
Co. No. 19; Ex. B.2
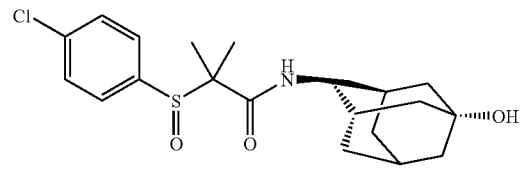 [SMILES: CC(C)(C(=O)N[C@H]1[C@@H]2CC3C[C@H]1C[C@](O)(C3)C2)S(=O)c1ccc(Cl)cc1]
Co. No. 5; Ex. B.4b
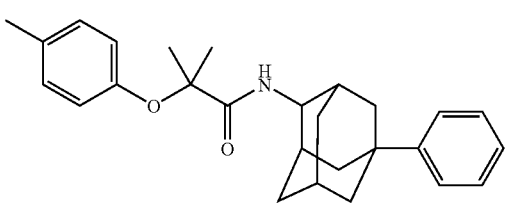 [SMILES: Cc1ccc(OC(C)(C)C(=O)NC2C3CC4CC2CC(c2ccccc2)(C4)C3)cc1]
Co. No. 49; Ex. B.23
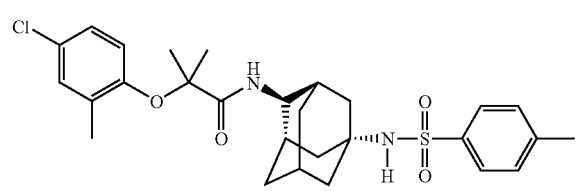 [SMILES: Cc1ccc(S(=O)(=O)N[C@@]23CC4C[C@H](C2)[C@H](NC(=O)C(C)(C)Oc2ccc(Cl)cc2C)[C@@H](C4)C3)cc1]
Co. No. 77; Ex. B.10
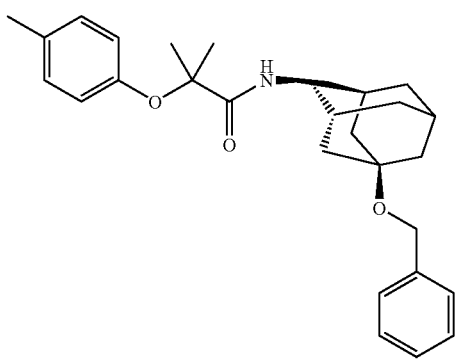 [SMILES: Cc1ccc(OC(C)(C)C(=O)N[C@@H]2[C@@H]3CC4C[C@H]2C[C@](OCc2ccccc2)(C4)C3)cc1]
Co. No. 48; Ex. B.22
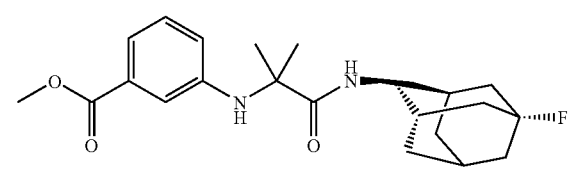 [SMILES: COC(=O)c1cccc(NC(C)(C)C(=O)N[C@H]2[C@@H]3CC4C[C@H]2C[C@](F)(C4)C3)c1]
Co. No. 78; Ex. B.12

TABLE F-1-continued
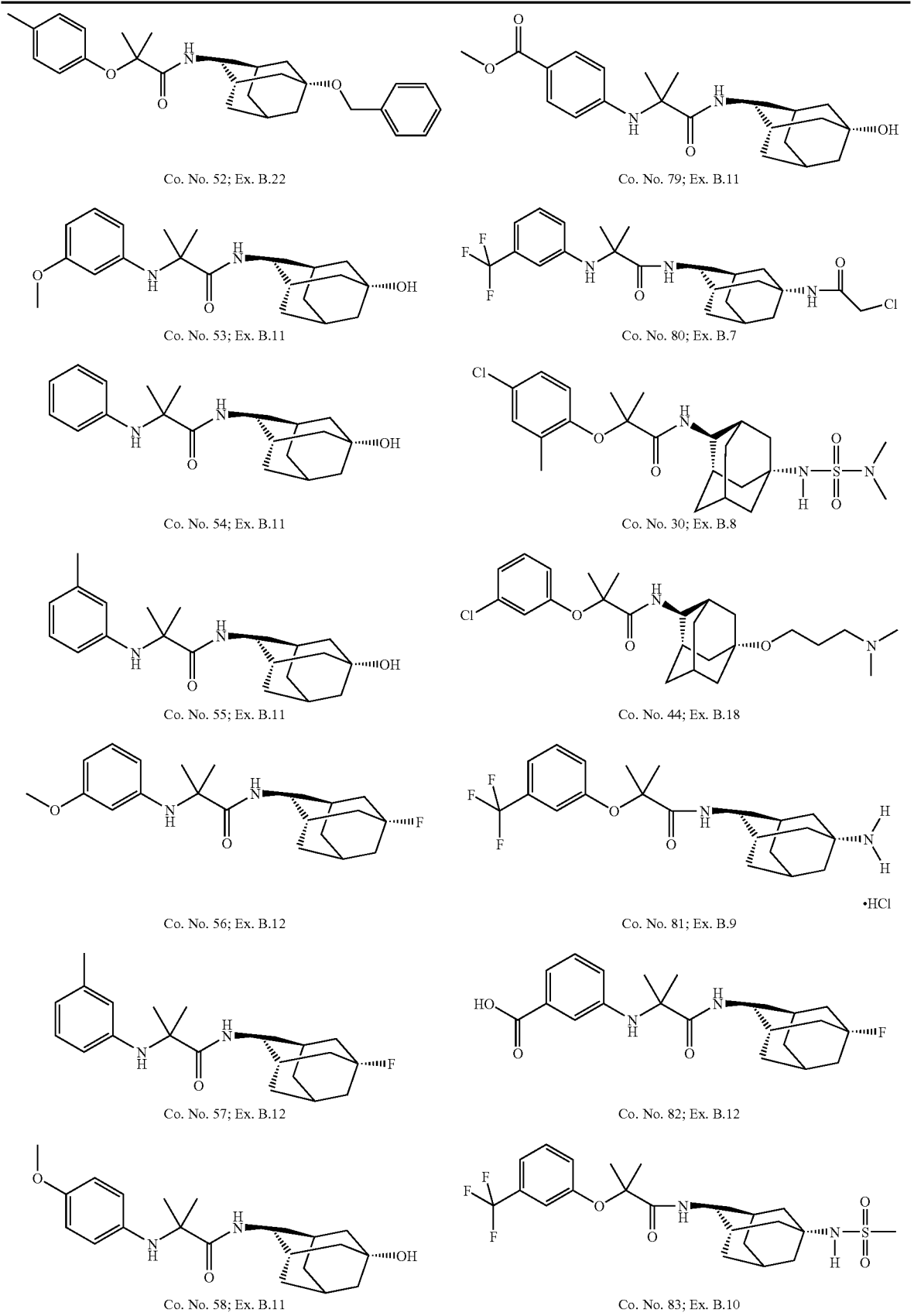

TABLE F-1-continued
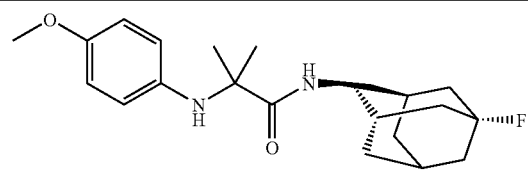
Co. No. 59; Ex. B.12
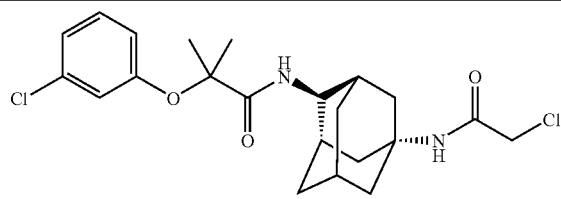
Co. No. 84; Ex. B.7
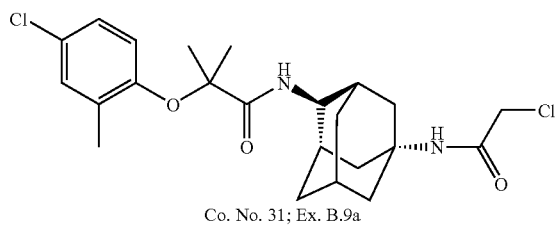
Co. No. 31; Ex. B.9a
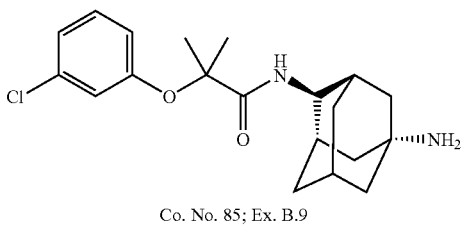
Co. No. 85; Ex. B.9
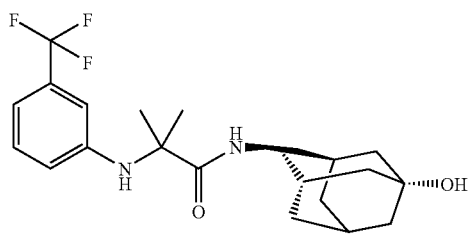 [SMILES: CC(C)(Nc1cccc(C(F)(F)F)c1)C(=O)N[C@H]1[C@@H]2CC3C[C@H]1C[C@](O)(C3)C2]
Co. No. 60; Ex. B.11
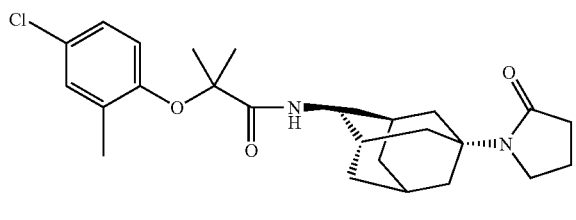 [SMILES: Cc1cc(Cl)ccc1OC(C)(C)C(=O)N[C@H]1[C@@H]2CC3C[C@H]1C[C@](N1CCCC1=O)(C3)C2]
Co. No. 39; Ex. B.15
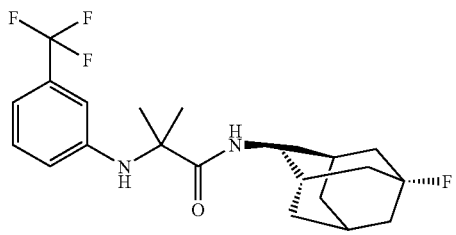 [SMILES: CC(C)(Nc1cccc(C(F)(F)F)c1)C(=O)N[C@H]1[C@@H]2CC3C[C@H]1C[C@](F)(C3)C2]
Co. No. 61; Ex. B.12
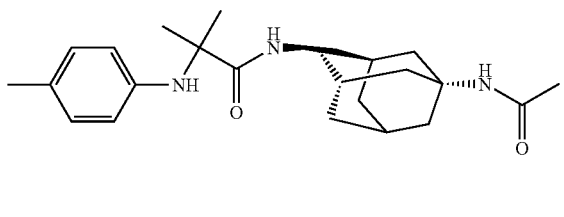 [SMILES: CC(=O)N[C@@]12CC3C[C@H](C1)[C@H](NC(=O)C(C)(C)Nc1ccc(C)cc1)[C@@H](C3)C2]
Co. No. 37; Ex. B.13
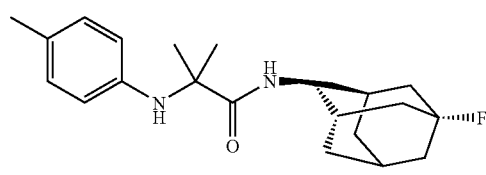 [SMILES: Cc1ccc(NC(C)(C)C(=O)N[C@H]2[C@@H]3CC4C[C@H]2C[C@](F)(C4)C3)cc1]
Co. No. 62; Ex. B.12
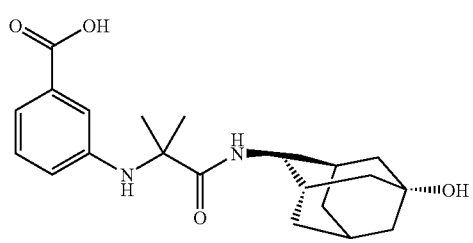 [SMILES: CC(C)(Nc1cccc(C(=O)O)c1)C(=O)N[C@H]1[C@@H]2CC3C[C@H]1C[C@](O)(C3)C2]
Co. No. 86; Ex. B.11
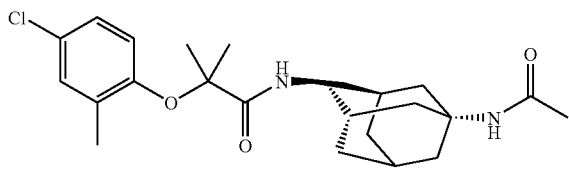 [SMILES: CC(=O)N[C@@]12CC3C[C@H](C1)[C@H](NC(=O)C(C)(C)Oc1ccc(Cl)cc1C)[C@@H](C3)C2]
Co. No. 29; Ex. B.7
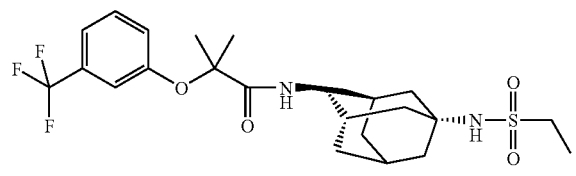 [SMILES: CCS(=O)(=O)N[C@@]12CC3C[C@H](C1)[C@H](NC(=O)C(C)(C)Oc1cccc(C(F)(F)F)c1)[C@@H](C3)C2]
Co. No. 87; Ex. B.10
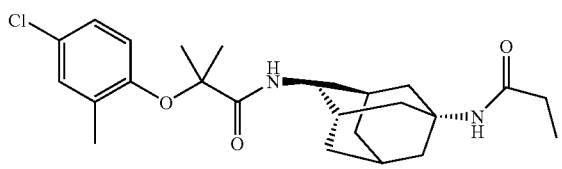 [SMILES: CCC(=O)N[C@@]12CC3C[C@H](C1)[C@H](NC(=O)C(C)(C)Oc1ccc(Cl)cc1C)[C@@H](C3)C2]
Co. No. 63; Ex. B.7
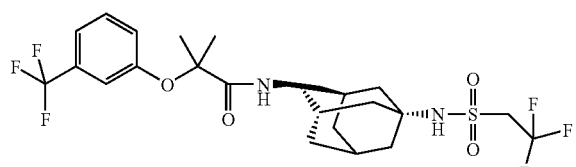
Co. No. 88; Ex. B.10

TABLE F-1-continued
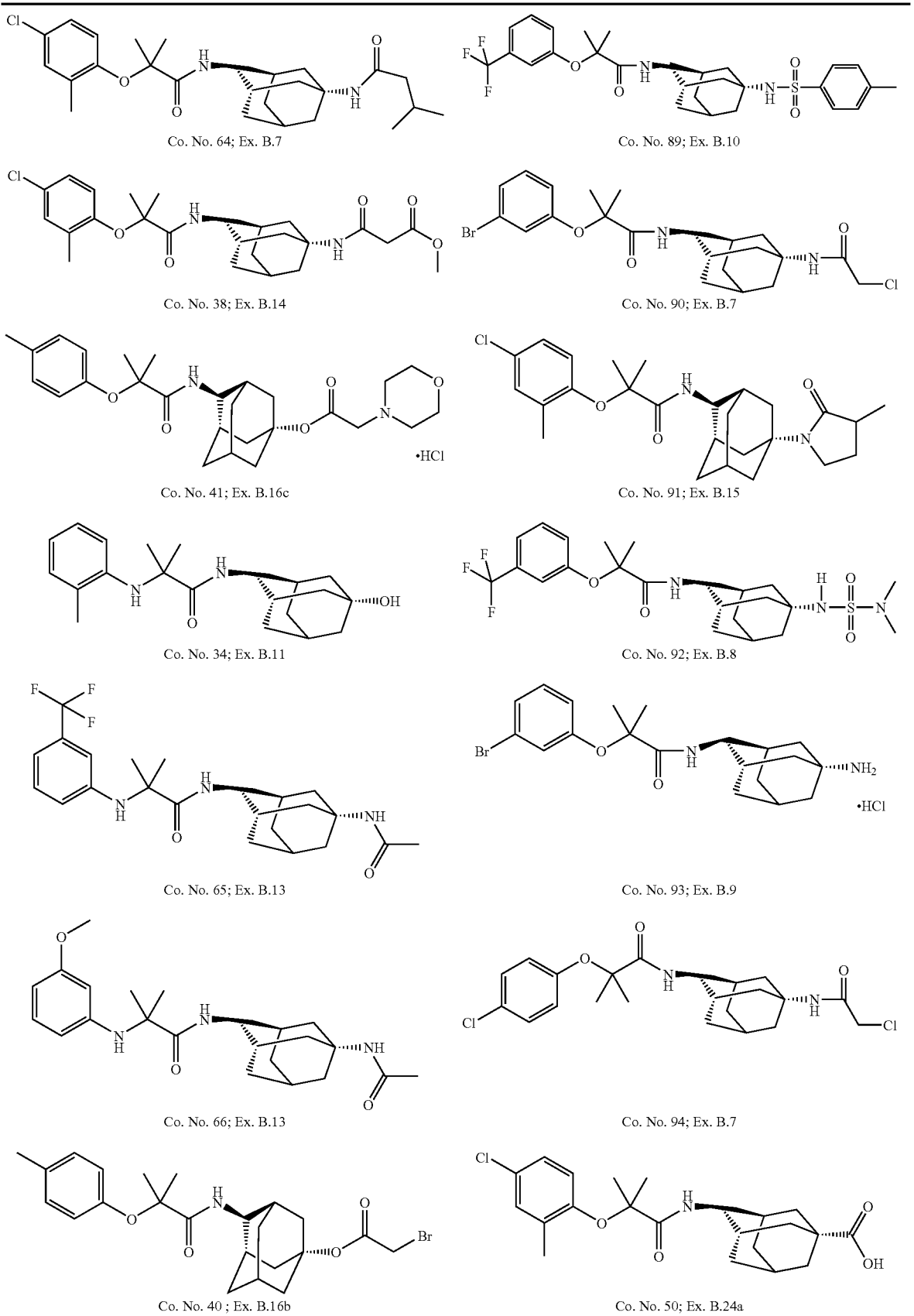

TABLE F-1-continued
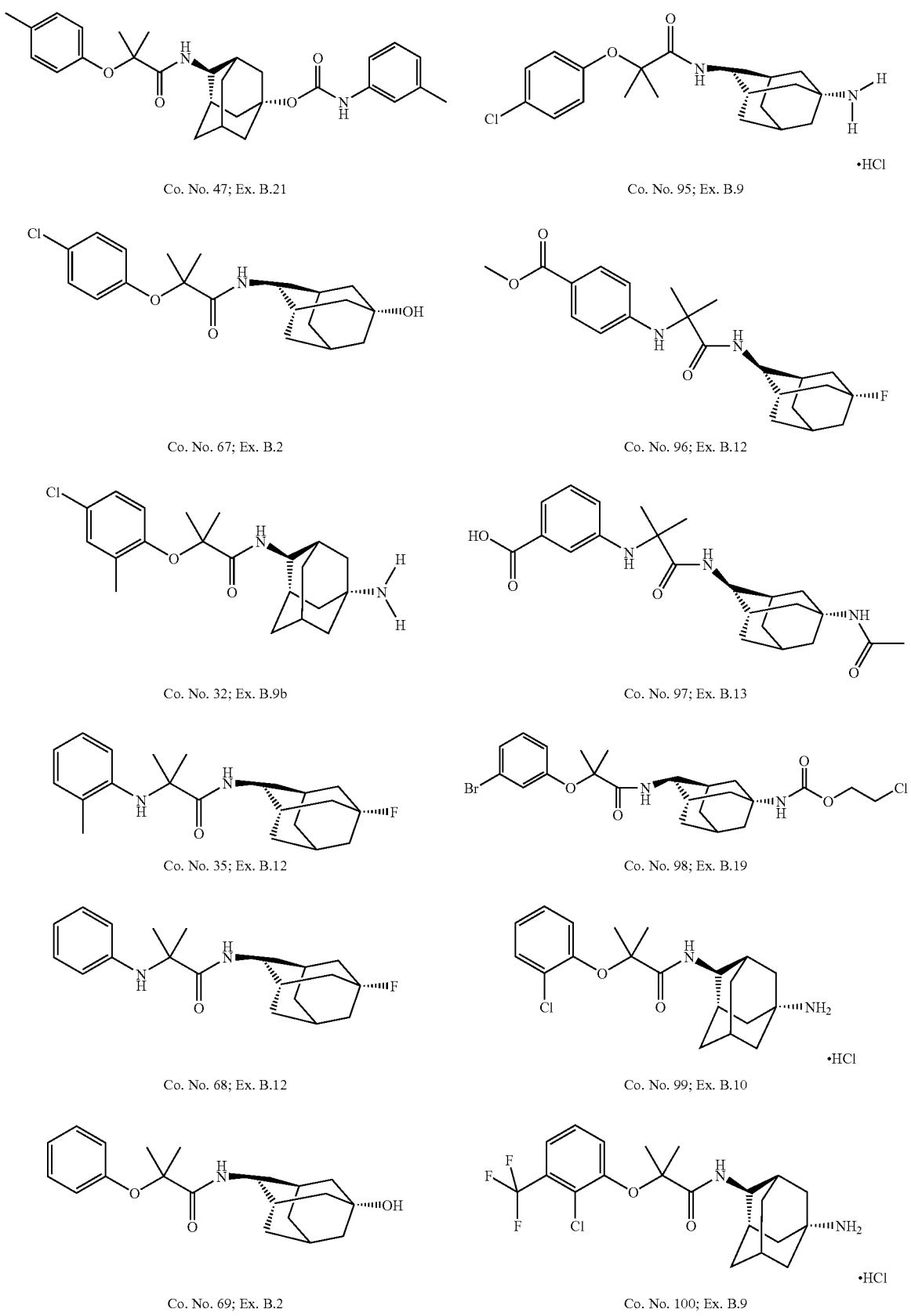
Co. No. 47; Ex. B.21
Co. No. 95; Ex. B.9
Co. No. 67; Ex. B.2
Co. No. 96; Ex. B.12
Co. No. 32; Ex. B.9b
Co. No. 97; Ex. B.13
Co. No. 35; Ex. B.12
Co. No. 98; Ex. B.19
Co. No. 68; Ex. B.12
Co. No. 99; Ex. B.10
Co. No. 69; Ex. B.2
Co. No. 100; Ex. B.9

TABLE F-1-continued
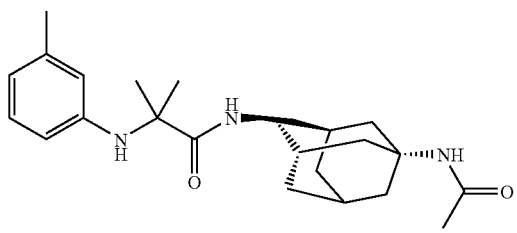 [SMILES: CC(=O)N[C@@]12CC3C[C@H](C1)[C@H](NC(=O)C(C)(C)Nc1cccc(C)c1)[C@@H](C3)C2]
Co. No. 70; Ex. B.13
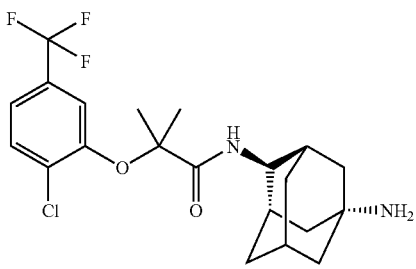
Co. No. 101; Ex. B.9
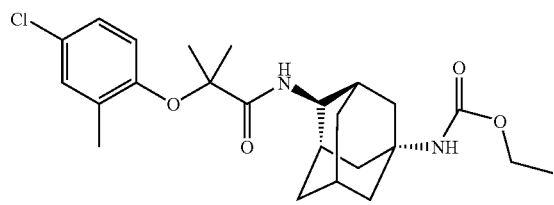 [SMILES: CCOC(=O)N[C@@]12CC3C[C@H](C1)[C@H](NC(=O)C(C)(C)Oc1ccc(Cl)cc1C)[C@@H](C3)C2]
Co. No. 45; Ex. B.19
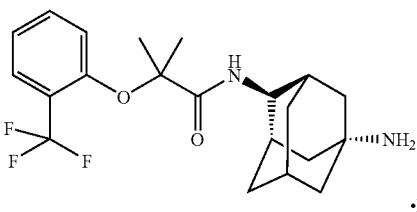
Co. No. 102; Ex. B.9
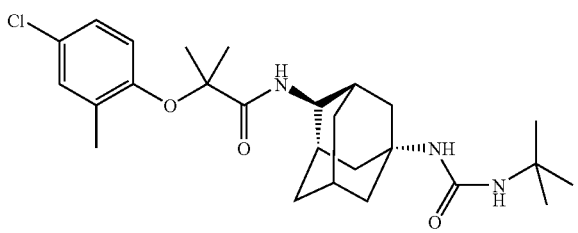 [SMILES: Cc1cc(Cl)ccc1OC(C)(C)C(=O)N[C@H]1[C@@H]2CC3C[C@H]1C[C@](NC(=O)NC(C)(C)C)(C3)C2]
Co. No. 71; Ex. B.17
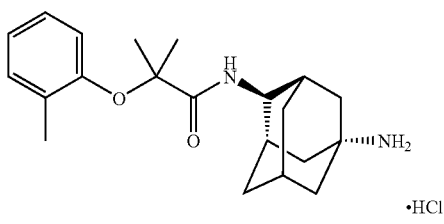 [SMILES: Cc1ccccc1OC(C)(C)C(=O)N[C@H]1[C@@H]2CC3C[C@H]1C[C@](N)(C3)C2 ; Cl]
Co. No. 103; Ex. B.9
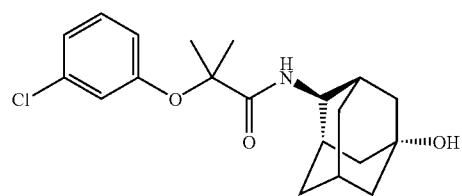 [SMILES: CC(C)(Oc1cccc(Cl)c1)C(=O)N[C@H]1[C@@H]2CC3C[C@H]1C[C@](O)(C3)C2]
Co. No. 43; Ex. B.18a
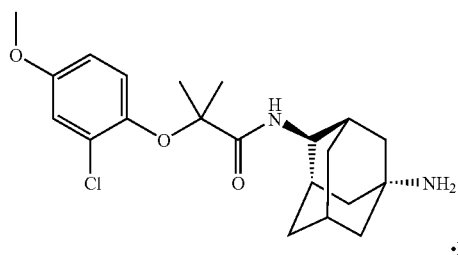
Co. No. 104; Ex. B.9
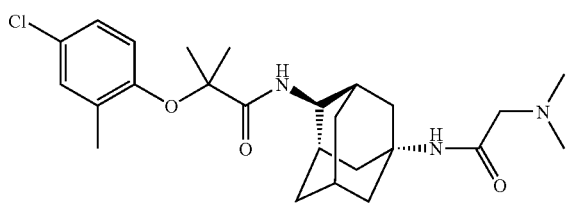 [SMILES: Cc1cc(Cl)ccc1OC(C)(C)C(=O)N[C@H]1[C@@H]2CC3C[C@H]1C[C@](NC(=O)CN(C)C)(C3)C2]
Co. No. 72; Ex. B.17
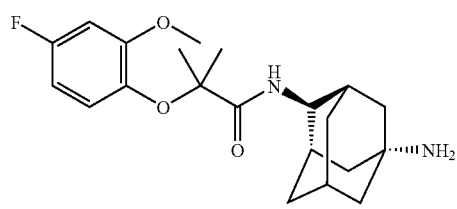
Co. No. 105; Ex. B.9
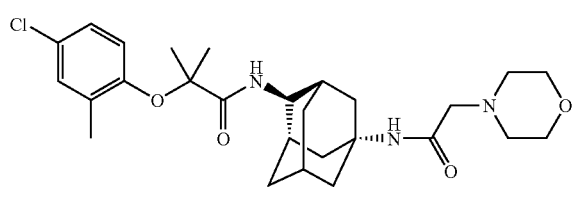 [SMILES: Cc1cc(Cl)ccc1OC(C)(C)C(=O)N[C@H]1[C@@H]2CC3C[C@H]1C[C@](NC(=O)CN1CCOCC1)(C3)C2]
Co. No. 73; Ex. B.17
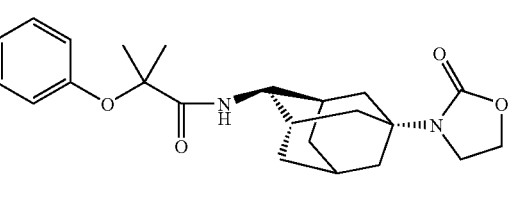
Co. No. 106; Ex. B.15

TABLE F-1-continued
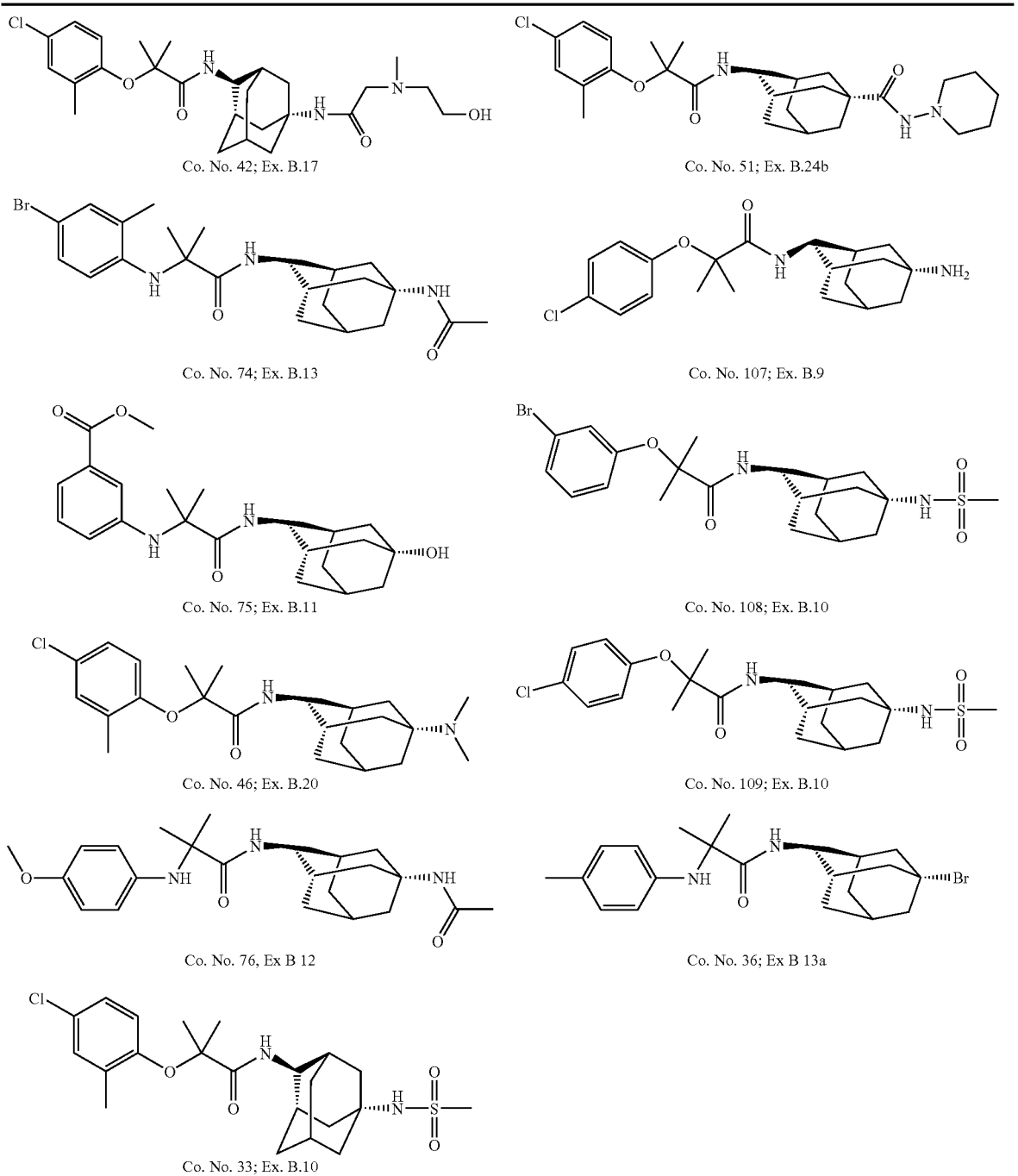
Table F-2 provides the $^1$H NMR chemical shifts data for the compounds of the present invention using $CDCl_3$ as a solvent.
TABLE F-2
| Co. No. | NMR data |
|---|---|
| 6 | 1H-NMR, $CDCl_3$; 1.37-2.14 (m, 13H, H-adamantane); 2.88 (s, 3H, N-$CH_3$); 3.36 and 3.51(2x dd, 2H, $CH_2$); 4.02 (d, CH); 4.74 (dd, 1H, OCH); 6.70 and 6.90 (2x t, 4H-aromatic); 6.81 (d, 1H, NH) |
| 8 | 1H-NMR, $CDCl_3$; 1.39-2.15 (m, 13H-adamantane); 4.03(d, 1H, CH); 4.28 and 4.48 (2x dd, $CH_2$); 4.71 (dd, 1H, OCH); 6.76 (d, NH); 6.91 (m, 3H, H-aromatic); 6.98-7.01 (m, 1H-aromatic) |

TABLE F-2-continued

| Co. No. | NMR data |
|---|---|
| 9 | mixture |
| 2 | 1H-NMR, CDCl$_3$; 1.51 (s, 6H, 2x CH$_3$); 1.54-1.95(m, 14H-adamantane); 2.26 (s, 6H, 2x CH$_3$); 4.09 (d, 1H, CH); 6.56 and 6.69 (2x s, 3H-aromatic); 7.11 (br d, NH) |
| 10 | 1H-NMR, CDCl$_3$; 1.52 (s, 6H, 2x CH$_3$); 1.44-2.18 (m, 13H-adamantane); 2.31 (s, 3H, CH$_3$); 4.06 (d, 1H, CH); 6.73 and 6.88 (2x d, 3H-aromatic); 7.01 (br d, NH); 7.14 (t, 1H-aromatic) |
| 11 | 1H-NMR, CDCl$_3$; 1.46-2.17 (m, 13H-adamantane); 2.21 (s, 3H, CH$_3$); 3.49 and 3.64 (2x dd, 2H, CH$_2$); 3.75 (br s, NH); 4.01 (d, CH); 4.64(dd, OCH); 6.44(s, 1H-aromatic; 6.50 (d, 1H-aromatic); 6.76-6.86 (m, NH, 1H-aromatic) |
| 12 | 1H-NMR, CDCl$_3$; 1.53 (s, 6H, 2x CH$_3$); 1.45-2.16 (m, 13H-adamantane); 2.28 (s, 3H, CH$_3$); 4.08 (d, 1H, CH); 6.86 and 6.95 (d and t, 2H-aromatic); 7.08 (m, NH, 1H-aromatic); 7.19 (d, 1H-aromatic) |
| 13 | 1H-NMR, CDCl$_3$; 1.48 (s, 6H, 2x CH$_3$); 1.44-2.16 (m, 13H-adamantane); 2.31 (s, 3H, CH$_3$); 4.05 (d, 1H, CH); 6.83 (m, 2H-aromatic); 7.08 (m, NH, 2H-aromatic) |
| 14 | 1H-NMR, CDCl$_3$; 1.48 (s, 6H, 2x CH$_3$); 1.46, 1.59, 1.75, 1.89, 2.10 (5x br d, 13H-adamantane); 3.78 (s, 3H, CH$_3$); 4.05 (d, 1H, CH); 6.52 (m, 2H-aromatic); 6.63 (d, 1H-aromatic); 6.96 (d, NH) 7.18 (t, 1H-aromatic) |
| 15 | 1H-NMR, CDCl$_3$; 1.53 (s, 6H, 2x CH$_3$); 1.45-1.93(m, 10H-adamantane); 2.10 (br s 3H-adamntane); 4.05 (d, 1H, CH); 6.85 (m, NH, 2H-aromatic); 7.09-7.22 (m, 3H-aromatic) |
| 16 | 1H-NMR, CDCl$_3$; 1.51 (s, 6H, 2x CH$_3$); 1.44-2.15 (m, 13H-adamantane); 2.28 (s, 6H, 2x CH$_3$); 4.06 (d, 1H, CH); 6.54 and 6.71 (2x s, 3H-aromatic); 7.01 (br d, NH) |
| 17 | 1H-NMR, CDCl$_3$; 1.53 (s, 6H, 2x CH$_3$); 1.42-2.15 (m, 13H-adamantane); 3.75 (s, 6H, 2x OCH$_3$); 4.04 (d, 1H, CH); 6.10 (d, 2H-aromatic); 6.20 (t, 1H-aromatic); 6.93 (d, NH) |
| 18 | 1H-NMR, CDCl$_3$; 1.52 (s, 6H, 2x CH$_3$); 1.42-2.15 (m, 13H-adamantane); 2.93 (s, 6H, 2x NCH$_3$); 4.05 (d, 1H, CH); 6.28 (m, 2H-aromatic); 6.45 (d, 1H-aromatic); 7.03 (d, NH); 7.10 (t, 1H-aromatic) |
| 19 | 1H-NMR, CDCl$_3$; 1.53 (s, 6H, 2x CH$_3$); 1.43-2.15 (m, 13H-adamantane); 2.17 (s, 3H, CH$_3$); 4.05 (d, 1H, CH); 6.67 (d, 1H-aromatic); 6.97 (d, NH); 7.10-7.23 (m, 3H-aromatic) |
| 20 | 1H-NMR, CDCl$_3$; 1.55 (s, 6H, 2x CH$_3$); 1.44-2.13 (m, 13H-adamantane); 4.06 (d, 1H, CH); 6.84 (d, NH); 7.10, 7.18, 7.33, 7.41 (d, s, d, t, 4H-aromatic) |
| 7 | 1H-NMR, CDCl$_3$; 1.50 (br d, 2H-adamantane); 1.80-1.99 (m, 8H-adamantane); 2.25 (br d, 3H-adamantane); 2.62 (s, 3H, CH$_3$); 4.25 (d, CH); 6.86 (d, NH); 7.28-7.64 (m, 4H-aromatic) |
| 21 | 1H-NMR, CDCl$_3$; 1.45-2.18 (m, 14H, 13H-adamantane, H$^A$-CH$_2$); 2.39 (m, 1H, H$^B$-CH$_2$); 2.80 (m, 2H, CH$_2$); 4.04 (d, CH); 4.56(dd, OCH); 6.77-6.80 (m, NH, 3H-aromatic) |
| 22 | 1H-NMR, CDCl$_3$; 1.45-2.18 (m, 14H, 13H-adamantane, H$^A$-CH$_2$); 2.39 (m, 1H, H$^B$-CH$_2$); 2.80 (m, 2H, CH$_2$); 4.04 (d, CH); 4.56(dd, OCH); 6.76-6.89 (m, NH, 3H-aromatic) |
| 23 | 1H-NMR, CDCl$_3$; 1.56-2.30 (m, 13H-adamantane); 4.26(d, CH); 6.84 (d, NH); 7.30 and 7.42 (2x t, 2H-aromatic); 7.53 and 7.69 (2x d, 2H- aromatic); 7.48 (s, 1H-furan) |
| 24 | 1H-NMR, CDCl$_3$; 1.40-2.21 (m, 13H-adamantane); 3.40 and 3.60 (2x dd, 2H, CH$_2$); 4.03 (d, CH); 5.14 (dd, OCH); 6.91 and 7.18 (2x m, 4H-aromatic) |
| 25 | 1H-NMR, CDCl$_3$; 1.60-2.31 (m, 13H-adamantane); 4.03 (s, 3H, CH$_3$); 4.23(d, CH); 6.86 (d, NH); 6.92 (dd, 1H-aromatic); 7.19-7.27 (m, 2H-aromatic); 7.47 (s, 1H-furan) |
| 26 | 1H-NMR, CDCl$_3$; 1.44-2.19 (m, 14H, 13H-adamantane, H$^A$-CH$_2$); 2.40 (m, 1H, H$^B$-CH$_2$); 2.81 (m, 2H, CH$_2$); 4.05 (d, CH); 4.56(dd, OCH); 6.85-6.94 (m, NH, 2H-aromatic); 7.05-7.17 (m, 2H-aromatic) |
| 27 | 1H-NMR, CDCl$_3$; 1.48 (s, 6H, 2x CH$_3$); 1.39, 1.56, 1.72, 1.89, 2.04 (5x br d, 13H-adamantane); 2.24 (s, 3H, CH$_3$); 3.63 (s, 1H, NH); 4.03 (d, 1H, CH); 6.50 (d, 2H-aromatic); 6.96 (d, 2H-aromatic); 7.48 (d, 1H, NH) |
| 28 | 1H-NMR, CDCl$_3$; 1.58, 2.08, 2.18, 2.21 (4x s, 4x CH$_3$); 1.05, 1.24, 1.48, (3x brd, 4H-adamantane); 1.62-1.98 (m, 9H-adamantane); 2.33-2.68 (m, 4H 2x CH$_2$); 3.91 (d, 1H, CH); 6.64 (d, 1H, NH) |
| 3 | 1H-NMR, CDCl$_3$; 1.55 (2x s, 6H, 2x CH$_3$); 1.59 and 2.20 (2x d, 6H-adamantane); 1.77-1.91 (m, 7H-adamantane); 4.02 (d, 1H, CH); 7.29 (d, 1H, NH); 7.54 and 7.77 (2x d, 4H-aromatic) |
| 1 | 1H-NMR, CDCl$_3$; 1.44, 1.59, 1.76, 1.81 (4x d, 10H-adamantane); 1.51 (s, 6H, 2x CH$_3$); 2.02 (br d, 3H-adamantane); 2.24 (s, 3H, CH$_3$); 4.06 (d, 1H, CH); 6.98 (d, 1H, NH); 6.78, 7.05, 7.17 (3xd, 3H-aromatic); |
| 4 | 1H-NMR, CDCl$_3$; 1.52 (s, 6H, 2x CH$_3$); 1.42-2.19 (m, 13H-adamantane); 4.00 (d, 1H, CH); 7.22 (d, 1H, NH); 7.24-7.33 (m, 4H-aromatic) |
| 5 | 1H-NMR, CDCl$_3$; 1.31 and 1.59 (2x s, 6H, 2x CH$_3$); 1.42-2.21 (m, 13H-adamantane); 3.98 (d, 1H, CH); 7.34 (d, 1H, NH); 7.45-7.55 (m, 4H-aromatic) |

Further Compound Identification
LCMS-Method:

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode.

Reversed phase HPLC was carried out on a Xterra MS C18 column (3.5 mm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 uL was used.

TABLE retention time (RT in minutes) and molecular weight as the MH+

| Compound No. | Rt | MH+ |
| --- | --- | --- |
| 6 | 4.77 | 343.2 |
| 8 | 5.15 | 328.1 |
| 9 | 5.58 | 342 |
| 2 | 7.52 | 342.3 |
| 10 | 6.12 | 344 |
| 11 | 5.31 | 343 |
| 12 | 6.17 | 344 |
| 13 | 6.19 | 344 |
| 14 | 5.72 | 360 |
| 15 | 6.28 | 425 |
| 16 | 6.45 | 358 |
| 17 | 5.72 | 390 |
| 18 | 5.72 | 279 |
| 19 | 4.71 | 404 |
| 20 | 6.21 | 415 |
| 7 | 5.98 | 651 |
| 21 | 5.54 | 404 |
| 22 | 5.55 | 404 |
| 23 | 5.39 | 623 |
| 24 | 5.09 | 353 |
| 25 | 5.29 | 359 |
| 26 | 5.55 | 328.1 |
| 27 | 5.52 | 343 |
| 28 | 5.65 | 400 |
| 3 | 5.54 | 279 |
| 1 | 6.54 | 376.2 |
| 4 | 6.42 | 380 |
| 5 | 5.04 | 396 |
| 49 | 7.52 | 404 |
| 48 | 7.28 | 434 |
| 52 | 7.38 | 434 |
| 53 | 4.98 | 359 |
| 54 | 5.08 | 329 |
| 55 | 5.44 | 343 |
| 56 | 6.02 | 361 |
| 57 | 6.37 | 345 |
| 58 | 4.95 | 359 |
| 59 | 5.98 | 361 |
| 31 | 6.78 | 470 |
| 60 | 5.68 | 397 |
| 61 | 6.49 | 399 |
| 62 | 6.41 | 345 |
| 29 | 6.59 | 170 |
| 63 | 6.51 | 433 |
| 64 | 7.01 | 288 |
| 38 | 6.32 | 477 |
| 41 | 6.72 | 471 |
| 34 | 5.61 | 343 |
| 65 | 5.78 | 455 |
| 66 | 5.15 | 400 |
| 47 | 7.21 | 477 |
| 67 | 6.22 | 125 |
| 32 | 5.62 | 377 |

TABLE-continued retention time (RT in minutes) and molecular weight as the MH+

| Compound No. | Rt | MH+ |
| --- | --- | --- |
| 35 | 6.48 | 345 |
| 68 | 6.14 | 331 |
| 69 | 5.78 | 330 |
| 70 | 5.55 | 384 |
| 45 | 6.99 | 466 |
| 71 | 6.99 | 476 |
| 43 | 6.17 | 346 |
| 72 | 6.78 | 462 |
| 73 | 6.79 | 504 |
| 42 | 6.52 | 492 |
| 74 | 6.18 | 464 |
| 75 | 5.02 | 387 |
| 46 | 5.68 | 405 |
| 76 | 5.09 | 400 |
| 33 | 6.55 | 453.2 |
| 77 | 7.11 | 548 |
| 78 | 6.02 | 389 |
| 79 | 4.78 | 387 |
| 80 | 6.48 | 490 |
| 30 | 6.82 | 501 |
| 44 | 5.91 | 449 |
| 81 | 5.32 | 397 |
| 82 | 4.21 | 375 |
| 83 | 6.24 | 492 |
| 39 | 6.88 | 462 |
| 37 | 5.61 | 384 |
| 86 | 3.12 | 373 |
| 87 | 6.38 | 506 |
| 88 | 6.54 | 541.1 |
| 89 | 6.85 | 568 |
| 90 | 6.17 | 482 |
| 91 | 7.05 | 476 |
| 92 | 6.52 | 521 |
| 93 | 5.32 | 409 |
| 94 | 6.48 | 456 |
| 50 | 6.12 | 306 |
| 95 | 5.22 | 363 |
| 96 | 5.84 | 389 |
| 97 | 3.35 | 431 |
| 98 | 6.29 | 512 |
| 99 | 5.11 | 363 |
| 100 | 5.61 | 431 |
| 102 | 4.98 | 397 |
| 103 | 5.14 | 343 |
| 104 | 5.02 | 222 |
| 105 | 4.95 | 377 |
| 106 | 6.44 | 496 |
| 51 | 6.85 | 488 |
| 108 | 6.34 | 502 |
| 109 | 6.25 | 441 |

C. Pharmacological Examples

EXAMPLE C1

Cellular Assays to Test the Effect of Compounds on 11β-Hydroxysteroid Dehydrogenase Type 1 and Type 2

The effects on 11β-HSD1 activity was measured in differentiated 3T3-L1 cells and rat hepatocytes.

Mouse fibroblast 3T3-L1 cells (ATCC-CL-173) were seeded at a density of 16500 cells/ml in 12 well plates and grown for 7 days in DMEM medium (supplemented with 10% heat inactivated foetal calf serum, 2 mM glutamine and 25 mg gentamycin) at 37° C. in a humidified 5% $CO_2$ atmosphere. Medium was refreshed twice a week. Fibroblasts were differentiated into adipocytes at 37° C. in a 5% $CO_2$ humidified atmosphere in growth medium containing 2 μg/ml insulin, 55 μg/ml IBMX and 39.2 μg/ml dexamethasone.

Primary hepatocytes from male rats were seeded on normal Falcon 12 well plates at a density of 250000 cells/well and incubated for 16 hours at 37° C. in a 5% CO$_2$ humidified atmosphere in DMEM-HAM's F12 medium containing 5% Nu-serum, 100 U/ml penicillin, 100 μg/ml streptomycin, 0.25 μg/ml amphotericin B, 50 μg/ml gentamycin sulfate, 5 μg/ml insulin and 392 ng/ml dexamethasone. Following a 4 hour pre-incubation with test compound, 0.5 μCi $^3$H-cortisone or dehydrocorticosterone, was added to the 3T3-L1 cultures. One hour later, the medium was extracted on Extrelut$^3$-columns with 15 ml diethyl ether and the extract was analysed by HPLC as described above. The effects of JNJ-compounds on rat hepatocyte HSD1 activity was measured after an incubation period of 90 minutes with 0.5 μCi$^3$H-dehydrocorticosterone. Corticosterone formation was analysed by HPLC.

The effects on 11β-HSD2 activity was studied in HepG2 and LCC-PK1-cells HepG2-cells (ATCC HB-8065) were seeded in 12 well plates at a density of 100,000 cells/ml and grown at 37° C. in a humidified 5% CO$_2$ atmosphere in MEM-Rega-3 medium supplemented with 10% heat inactivated foetal calf serum, 2 mM L-glutamine and sodium bicarbonate). Medium was refreshed twice a week.

Pig kidney cells (LCC-PK1, ATCC CRL-1392) were seeded at a density of 150,000 cells/ml in 12 well plates and grown at 37° C. in a humidified 5% CO$_2$ atmosphere in Medium 199 supplemented with Earls modified salt solution, 100 U/ml penicillin, 100 μg/ml streptomycin and 10% foetal calf serum. Medium was refreshed twice a week. Twenty four hours prior to the onset of the experiment, medium was changed by medium containing 10% charcoal stripped foetal calf serum.

Following a 4 hour pre-incubation with test compound, 0.5 μCi $^3$H-cortisol or corticosterone, was added to the cultures. One hour later, the medium was extracted on Extrelut$^3$-columns with 15 ml diethyl ether and the extract was analysed by HPLC as described above.

As for the enzymatic assays, the compounds to be tested were taken from a stock solution and tested at a final concentration ranging from $10^{-5}$M to $10^{-10}$M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below. (in this table NT stands for Not Tested).

| Compound Number | HSD2 cellular HepG2 Score | HSD1 cellular 3T3-L1 Score |
|---|---|---|
| 5 | NT | 3 |
| 6 | 1 | 3 |
| 8 | 2 | 3 |
| 9 | 3 | 3 |
| 2 | 1 | 3 |
| 10 | 2 | 3 |
| 11 | 2 | 3 |
| 12 | 3 | 3 |
| 13 | 3 | 3 |
| 14 | 3 | 3 |
| 15 | 3 | 3 |
| 16 | 3 | 3 |
| 17 | 2 | 3 |
| 18 | 3 | 3 |
| 19 | 3 | 3 |
| 20 | 3 | 3 |
| 7 | 1 | 3 |
| 21 | 3 | 3 |
| 22 | 2 | 3 |
| 23 | 1 | 3 |
| 24 | 2 | 3 |
| 25 | 2 | 3 |
| 26 | 3 | 3 |
| 27 | 1 | 3 |
| 28 | 3 | 3 |
| 3 | 3 | 3 |
| 1 | 3 | 3 |
| 4 | 2 | 3 |
| 99 | NT | 3 |
| 102 | NT | 3 |
| 104 | NT | 3 |
| 101 | NT | 3 |
| 105 | NT | 3 |
| 103 | NT | 3 |
| 32 | 1 | 3 |
| 100 | NT | 3 |
| 95 | 1 | 3 |
| 93 | 1 | 3 |
| 85 | 1 | 3 |
| 81 | 1 | 3 |
| 34 | 2 | 3 |
| 54 | 1 | 3 |
| 55 | 1 | 3 |
| 53 | 1 | 3 |
| 60 | 1 | 3 |
| 58 | 1 | 3 |
| 79 | NT | 3 |
| 75 | 1 | 3 |
| 86 | NT | 2 |
| 37 | 1 | 3 |
| 74 | 2 | 3 |
| 70 | 2 | 3 |
| 65 | 1 | 3 |
| 76 | 1 | 3 |
| 66 | 2 | 3 |
| 97 | NT | 1 |
| 35 | 2 | 3 |
| 68 | 1 | 3 |
| 57 | 1 | 3 |
| 62 | 1 | 3 |
| 56 | 1 | 3 |
| 59 | 1 | 3 |
| 78 | NT | 3 |
| 61 | 1 | 3 |
| 96 | NT | 2 |
| 82 | NT | 2 |
| 38 | 2 | 3 |
| 39 | 3 | 3 |
| 91 | 3 | 3 |
| 41 | 2 | 3 |
| 50 | 2 | 3 |
| 42 | 2 | 3 |
| 73 | 2 | 3 |
| 72 | 2 | 3 |
| 71 | NT | 2 |
| 44 | 2 | 3 |
| 45 | 2 | 3 |
| 98 | NT | 3 |
| 67 | 2 | 3 |
| 69 | 2 | 3 |
| 43 | 3 | 3 |
| 46 | 1 | 3 |
| 47 | 2 | 3 |
| 48 | 3 | 3 |
| 52 | 2 | 3 |
| 49 | 1 | 2 |
| 29 | 3 | 3 |
| 63 | 3 | 3 |
| 31 | 2 | 3 |
| 64 | 2 | 3 |
| 94 | 2 | 3 |
| 80 | 2 | 3 |
| 90 | 2 | 3 |
| 30 | 2 | 3 |
| 92 | 2 | 3 |
| 33 | 2 | 3 |
| 83 | 2 | 3 |
| 87 | 2 | 3 |

-continued

| Compound Number | HSD2 cellular HepG2 Score | HSD1 cellular 3T3-L1 Score |
|---|---|---|
| 77 | 1 | 3 |
| 88 | 2 | 3 |
| 89 | 1 | 3 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10,000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound of formula (I),

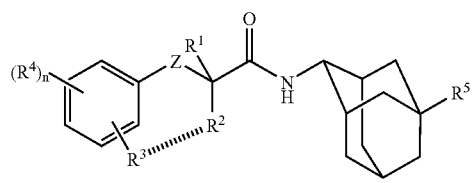

the N-oxide forms, the pharmaceutically acceptable addition salts and the stereochemically isomeric forms thereof, wherein n is 1, 2, 3, or 4;

Z represents O, S, SO or $SO_2$;

$R^1$ represent hydrogen, cyano, hydroxy, or $C_{1-4}$alkyl optionally substituted with halo, or $R^1$ is absent wherein $R^2$ and $R^3$ form —$CR^{10}$=;

$R^2$ represents hydrogen, $C_{1-4}$alkyl, or $C_{1-4}$alkyloxy-;

$R^3$ represents hydrogen, $C_{1-4}$alkyl, $C_{1-4}$alkyloxy- or $R^3$ combined with $R^2$ form together a radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;

$R^4$ represents hydrogen, halo, hydroxy, cyano, amino, $NR^{11}R^{12}$, $C_{1-4}$alkyloxycarbonyl, hydroxycarbonyl, $C_{1-4}$alkyloxy- optionally substituted with one, two or three substituents selected from hydroxy and halo or $R^4$ represents $C_{1-4}$alkyl optionally substituted with one, two or three substituents selected from hydroxy and halo;

$R^5$ represents hydrogen, halo, cyano, amino, phenyl, hydroxy, $C_{1-4}$alkyloxycarbonyl-, hydroxycarbonyl-, Het$^1$, —$NR^{13}R^{14}$, —O—(C=O)—$NR^{21}R^{22}$, —O—(C=O)—$C_{1-4}$alkyl, carbonyl-$NR^{23}R^{24}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$, or $R^5$ represents —O(C=O)—$C_{1-4}$alkyl substituted with one or more Het$^3$ or halo substituents;

$R^{11}$ and $R^{12}$ each independently represent hydrogen, $C_{1-4}$alkyl or $C_{1-4}$alkylcarbonyl-;

$R^{13}$ and $R^{14}$ each independently represent hydrogen, $C_{1-4}$alkyl, $C_{1-6}$alkyl-$SO_2$—, mono- or di($C_{1-4}$alkyl)amino-$SO_2$—, Ar$^1$—$SO_2$, mono- or di($C_{1-4}$alkyl)amino-carbonyl-, $C_{1-4}$alkyl-oxycarbonyl or $C_{1-4}$alkylcarbonyl- wherein said $C_{1-6}$alkyl-$SO_2$—, $C_{1-4}$alkyl-oxycarbonyl or $C_{1-4}$alkyl-carbonyl- are each independently and optionally substituted with one, two or three substituents selected from halo, $C_{1-4}$alkyloxycarbonyl, $NR^{19}R^{20}$ and Het$^2$;

$R^{15}$ and $R^{16}$ each independently represent hydrogen, $C_{1-4}$alkyl, $C_{1-4}$alkyloxycarbonyl or $C_{1-4}$alkylcarbonyl-;

$R^{17}$ and $R^{18}$ each independently represent hydrogen, $C_{1-4}$alkyl, $C_{1-4}$alkyloxycarbonyl or $C_{1-4}$alkylcarbonyl-;

$R^{19}$ and $R^{20}$ each independently represent hydrogen, $C_{1-4}$alkylcarbonyl or $C_{1-4}$alkyl optionally substituted with one or more substituents selected from halo or hydroxy;

$R^{21}$ and $R^{22}$ each independently represent hydrogen, Ar$^2$ or $C_{1-4}$alkyl optionally substituted with one or more substituents selected from halo or hydroxy;

$R^{23}$ and $R^{24}$ each independently represent hydrogen, $C_{1-4}$alkylcarbonyl, Het$^4$ or $C_{1-4}$alkyl optionally substituted with hydroxy;

Het$^1$ represents pyrrolinyl, pyrrolidinyl, pyrrolyl, oxazolyl, isoxazolyl or a radical of formula

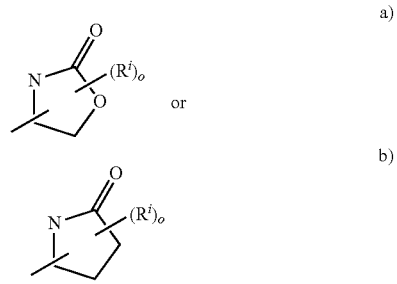

wherein R$^i$ represents hydrogen or $C_{1-4}$alkyl and o is 1 or 2;

Het$^2$ represents morpholinyl, piperidinyl, piperazinyl, thiomorpholinyl or pyrrolidinyl;

Het³ represents morpholinyl, piperidinyl, piperazinyl, thiomorpholinyl or pyrrolidinyl;
Het⁴ represents piperidinyl, morpholinyl, piperazinyl, thiomorpholinyl or pyrrolidinyl;
Ar¹ represents phenyl optionally substituted with $C_{1-4}$alkyl; and
Ar² represents phenyl optionally substituted with $C_{1-4}$alkyl.

2. A compound according to claim 1 wherein
n is 1, 2, 3, or 4;
Z represents O, S, SO or $SO_2$;
$R^1$ represent hydrogen, cyano, hydroxy, or $C_{1-4}$alkyl optionally substituted with halo, or $R^1$ is absent wherein $R^2$ and $R^3$ form —$CR^{10}$=;
$R^2$ represents hydrogen, $C_{1-4}$alkyl, or $C_{1-4}$alkyloxy-;
$R^3$ represents hydrogen, $C_{1-4}$alkyl, $C_{1-4}$alkyloxy- or $R^3$ combined with $R^2$ form together a radical selected from the group consisting of —O—$CH_2$— (a), —$NR^7$—$CH_2$— (b), —$(CR^8R^9)_m$- (c) and —$CR^{10}$= (d) wherein m represents 1 or 2 and $R^7$, $R^8$, $R^9$ and $R^{10}$ are each independently selected from hydrogen or $C_{1-4}$alkyl;
$R^4$ represents hydrogen, halo, hydroxy, cyano, amino, $NR^{11}R^{12}$, $C_{1-4}$alkyloxy- optionally substituted with one or where possible two or three substituents selected from hydroxy and halo or $R^4$ represents $C_{1-4}$alkyl optionally substituted with one, two or three substituents selected from hydroxy and halo;
$R^5$ represents halo, cyano, amino, phenyl, hydroxy, $C_{1-4}$alkyloxycarbonyl-, hydroxycarbonyl, $NR^{13}R^{14}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$;
$R^{11}$ and $R^{12}$ each independently represent hydrogen, $C_{1-4}$alkyl or $C_{1-4}$alkylcarbonyl-;
$R^{13}$ and $R^{14}$ each independently represent hydrogen, $C_{1-4}$alkyl or $C_{1-4}$alkylcarbonyl-;
$R^{15}$ and $R^{16}$ each independently represent hydrogen, $C_{1-4}$alkyl or $C_{1-4}$alkylcarbonyl-; and
$R^{17}$ and $R^{18}$ each independently represent hydrogen, $C_{1-4}$alkyl or $C_{1-4}$alkylcarbonyl-.

3. A compound of formula (I^i),

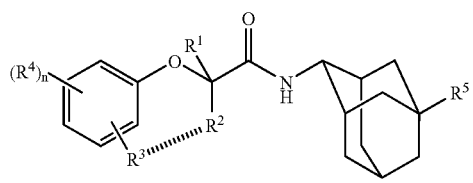

the N-oxide forms, the pharmaceutically acceptable addition salts and the stereochemically isomeric forms thereof, wherein
n is 1, 2, 3, or 4;
$R^1$ represent hydrogen, cyano, hydroxy, or $C_{1-4}$alkyl optionally substituted with halo,
$R^2$ represents hydrogen, $C_{1-4}$alkyl, or $C_{1-4}$alkyloxy-;
$R^3$ represents hydrogen, $C_{1-4}$alkyl, $C_{1-4}$alkyloxy- or $R^3$ combined with $R^2$ form together a divalent radical selected from the group consisting of —O—$CH_2$— (a), —$NR^7$—$CH_2$— (b), and —$(CR^8R^9)_m$- (c) wherein m represents 1 or 2 and $R^7$, $R^8$, and $R^9$ are each independently selected from hydrogen or $C_{1-4}$alkyl;
$R^4$ represents hydrogen, halo, hydroxy, cyano, amino, $NR^{11}R^{12}$, $C_{1-4}$alkyloxycarbonyl, hydroxycarbonyl, $C_{1-4}$alkyloxy- optionally substituted with one or where possible two or three substituents selected from hydroxy and halo or $R^4$ represents $C_{1-4}$alkyl optionally substituted with one, two or three substituents selected from hydroxy and halo;
$R^5$ represents hydrogen, halo, cyano, amino, phenyl, hydroxy, $C_{1-4}$alkyloxycarbonyl, hydroxycarbonyl-, Het¹, —$NR^{13}R^{14}$, —O—(C=O)—$NR^{21}R^{22}$, —O—(C=O)—$C_{1-4}$alkyl, carbonyl-$NR^{23}R^{24}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from halo, hydroxy, hydroxycarbonyl, phenyl, $C_{1-4}$alkyloxy or $NR^{17}R^{18}$, or $R^5$ represents —O—(C=O)—$C_{1-4}$alkyl substituted with one or more amino, hydroxy, Het³ or halo substituents;
$R^{11}$ and $R^{12}$ each independently represent hydrogen, $C_{1-4}$alkyl, $C_{1-4}$alkyloxycarbonyl- or $C_{1-4}$alkylcarbonyl-;
$R^{13}$ and $R^{14}$ each independently represent hydrogen, $C_{1-4}$alkyl, $C_{1-6}$alkyl-$SO_2$—, mono- or di($C_{1-4}$alkyl)amino-$SO_2$—, Ar¹—$SO_2$, mono- or di($C_{1-4}$alkyl)amino-carbonyl-, $C_{1-4}$alkyl-oxycarbonyl or $C_{1-4}$alkylcarbonyl- wherein said $C_{1-6}$alkyl-$SO_2$—, $C_{1-4}$alkyloxycarbonyl or $C_{1-4}$alkylcarbonyl- are each independently and optionally substituted with one, two or three substituents selected from halo, $C_{1-4}$alkyloxycarbonyl, $NR^{19}R^{20}$ and Het²;
$R^{15}$ and $R^{16}$ each independently represent hydrogen, $C_{1-4}$alkyl, $C_{1-4}$alkyloxycarbonyl- or $C_{1-4}$alkylcarbonyl-;
$R^{17}$ and $R^{18}$ each independently represent hydrogen, $C_{1-4}$alkyl, $C_{1-4}$alkyloxycarbonyl- or $C_{1-4}$alkylcarbonyl-;
$R^{19}$ and $R^{20}$ each independently represent hydrogen, $C_{1-4}$alkyloxycarbonyl-, $C_{1-4}$alkylcarbonyl or $C_{1-4}$alkyl optionally substituted with halo or hydroxy;
$R^{21}$ and $R^{22}$ each independently represent hydrogen, Ar² or $C_{1-4}$alkyl optionally substituted with halo or hydroxy;
$R^{23}$ and $R^{24}$ each independently represent hydrogen, $C_{1-4}$alkylcarbonyl, Het⁴ or $C_{1-4}$alkyl optionally substituted with halo or hydroxy;
Het¹ represents pyrrolinyl, pyrrolidinyl, pyrrolyl, oxazolyl, isoxazolyl or a radical of formula

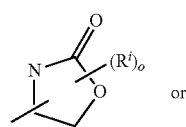

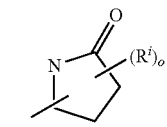

wherein $R^i$ represents hydrogen or $C_{1-4}$alkyl and o is 1 or 2;

Het² represents morpholinyl, piperidinyl, piperazinyl, thiomorpholinyl or pyrrolidinyl;

Het³ represents morpholinyl, piperidinyl, piperazinyl, thiomorpholinyl or pyrrolidinyl;

Het⁴ represents piperidinyl, morpholinyl, piperazinyl, thiomorpholinyl or pyrrolidinyl;

Ar¹ represents phenyl optionally substituted with $C_{1-4}$alkyl; and

Ar² represents phenyl optionally substituted with $C_{1-4}$alkyl; provided however that said compound of formula (I') is other than Acetamide, N-tricyclo[3.3.1.1³,⁷]dec-2-yl-2-[3-(trifluoromethyl)phenoxy]-(9CI)

Acetamide, 2-[4-(1-methylpropyl)phenoxy]-N-tricyclo[3.3.1.1³,⁷]dec-2-yl-(9CI)

Butanamide, 2-phenoxy-N-tricyclo[3.3.1.1³,⁷]dec-2-yl-(9CI)

Acetamide, 2-(2-bromo-4-ethylphenoxy)-N-tricyclo[3.3.1.1³,⁷]dec-2-yl-(9CI)

Acetamide, N-tricyclo[3.3.1.1³,⁷]dec-2-yl-2-(2,3,5-trimethylphenoxy)-(9CI)

Acetamide, 2-(2,3-dimethylphenoxy)-N-tricyclo[3.3.1.1³,⁷]dec-2-yl-(9CI)

Acetamide, 2-(2,4-dibromo-6-methylphenoxy)-N-tricyclo[03.3.1.1³,⁷]dec-2-yl-(9CI)

Acetamide, 2-(4-chloro-2-methylphenoxy)-N-tricyclo[3.3.1.1³,⁷]dec-2-yl-(9CI)

Acetamide, 2-(3,5-dimethylphenoxy)-N-tricyclo[3.3.1.1³,⁷]dec-2-yl-(9CI)

Acetamide, 2-(2-chlorophenoxy)-N-tricyclo[3.3.1.1³,⁷]dec-2-yl-(9CI)

Acetamide, 2-[4-(1,1-dimethylethyl)phenoxy]-N-tricyclo[3.3.1.1³,⁷]dec-2-yl-(9CI)

Acetamide, 2-[5-methyl-2-(1-methylethyl)phenoxy-N-tricyclo[3.3.1.1³,⁷]dec-2-yl-(9CI)

Acetamide, 2-(4-ethylphenoxy)-N-tricyclo[3.3.1.1³,⁷]dec-2-yl-(9CI)

Acetamide, 2-(2,5-dimethylphenoxy)-N-tricyclo[3.3.1.1³,⁷]dec-2-yl-(9CI)

Acetamide, 2-(3,4-dimethylphenoxy)-N-tricyclo[3.3.1.1³,⁷]dec-2-yl-(9CI)

Acetamide, 2-(2,4-dimethylphenoxy)-N-tricyclo[3.3.1.1³,⁷]dec-2-yl-(9CI)

Acetamide, 2-(4-bromo-2-methylphenoxy)-N-tricyclo[3.3.1.1³,⁷]dec-2-yl-(9CI)

Acetamide, 2-(4-bromo-3,5-dimethylphenoxy)-N-tricyclo[3.3.1.1³,⁷]dec-2-yl-(9CI)

Acetamide, 2-[4-(1-methylethyl)phenoxy]-N-tricyclo[3.3.1.1³,⁷]dec-2-yl-(9CI)

Acetamide, 2-(4-bromo-2-chlorophenoxy)-N-tricyclo[3.3.1.1³,⁷]dec-2-yl-(9CI)

Acetamide, 2-(4-chloro-3-methylphenoxy)-N-tricyclo[3.3.1.1³,⁷]dec-2-yl-(9CI)

Acetamide, 2-(4-methoxyphenoxy)-N-tricyclo[3.3.1.1³,⁷]dec-2-yl-(9CI)

Propanamide, 2-(2,4-dichlorophenoxy)-N-tricyclo[3.3.1.1³,⁷]dec-2-yl-(9CI)

Acetamide, 2-(2-bromo-4-methylphenoxy)-N-tricyclo[3.3.1.1³,⁷]dec-2-yl-(9CI)

Acetamide, 2-(4-chloro-3,5-dimethylphenoxy)-N-tricyclo[3.3.1.1³,⁷]dec-2-yl-(9CI)

Acetamide, 2-(4-bromo-3-methylphenoxy)-N-tricyclo[3.3.1.1³,⁷]dec-2-yl-(9CI)

Acetamide, 2-(2,4-dichlorophenoxy)-N-tricyclo[3.3.1.1³,⁷]dec-2-yl-(9CI)

Acetamide, 2-phenoxy-N-tricyclo[3.3.1.1³,⁷]dec-2-yl-(9CI)

Acetamide, 2-(4-bromophenoxy)-N-tricyclo[3.3.1.1³,⁷]dec-2-yl-(9CI)

Acetamide, 2-(4-methylphenoxy)-N-tricyclo[3.3.1.1³,⁷]dec-2-yl-(9CI)

Acetamide, 2-(3-bromophenoxy)-N-tricyclo[3.3.1.1³,⁷]dec-2-yl-(9CI)

Acetamide, 2-(4-chlorophenoxy)-N-tricyclo[3.3.1.1³,⁷]dec-2-yl-(9CI)

Acetamide, 2-(3-methylphenoxy)-N-tricyclo[3.3.1.1³,⁷]dec-2-yl-(9CI) or

N-adamantan-2-yl-2-o-tolyloxy-acetamide.

4. A compound according to claim 3, wherein n is 1, 2, 3, or 4;

$R^1$ represent hydrogen, cyano, hydroxy, or $C_{1-4}$alkyl optionally substituted with halo, $R^2$ represents hydrogen, $C_{1-4}$alkyl, or $C_{1-4}$alkyloxy-;

$R^3$ represents hydrogen, $C_{1-4}$alkyl, $C_{1-4}$alkyloxy- or $R^3$ combined with $R^2$ form together a radical selected from the group consisting of —O—CH₂— (a), —NR⁷—CH₂— (b), and —(CR⁸R⁹)$_m$- (c) wherein m represents 1 or 2 and $R^7$, $R^8$, and $R^9$ are each independently selected from hydrogen or $C_{1-4}$alkyl;

$R^4$ represents hydrogen, halo, hydroxy, cyano, amino, NR¹¹R¹², $C_{1-4}$alkyloxy- optionally substituted with one, two or three substituents selected from hydroxy and halo or $R^4$ represents $C_{1-4}$alkyl optionally substituted with one, two or three substituents selected from hydroxy and halo;

$R^5$ represents hydrogen, halo, cyano, amino, phenyl, hydroxy, $C_{1-4}$alkyloxycarbonyl, hydroxycarbonyl, NR¹³R¹⁴ or $C_{1-4}$alkyl optionally substituted with one or more substituents selected from hydroxycarbonyl, phenyl, $C_{1-4}$alkyloxy or NR¹⁵R¹⁶ or $R^5$ represents $C_{1-4}$alkyloxy optionally substituted with one or more substituents selected from hydroxycarbonyl, phenyl, $C_{1-4}$alkyloxy or NR¹⁷R¹⁸, $R^{11}$ and $R^{12}$ each independently represent hydrogen, $C_{1-4}$alkyl or $C_{1-4}$alkylcarbonyl-;

$R^{13}$ and $R^{14}$ each independently represent hydrogen, $C_{1-4}$alkyl or $C_{1-4}$alkylcarbonyl-;

$R^{15}$ and $R^{16}$ each independently represent hydrogen, $C_{1-4}$alkyl or $C_{1-4}$alkylcarbonyl-; and $R^{17}$ and $R^{18}$ each independently represent hydrogen, $C_{1-4}$alkyl or $C_{1-4}$alkylcarbonyl-, provided however that when $R^5$ represents hydrogen in said compound of formula (I'), then $R^1$ and $R^2$ represent $C_{1-4}$alkyl.

5. A compound according to claim 3 wherein:

n is 1, 2, 3, or 4;

$R^1$ represents a hydrogen or $C_{1-4}$alkyl;

$R^3$ combined with $R^2$ form together a divalent radical selected from the group consisting of —O—CH₂— (a), —NR⁷—CH₂— (b), and —(CR⁸R⁹)$_m$- (c) wherein m represents 1 or 2 and $R^7$, $R^8$, and $R^9$ are each independently selected from hydrogen or $C_{1-4}$alkyl;

$R^4$ represents hydrogen, halo, hydroxy, $C_{1-4}$alkyloxy-, or $C_{1-4}$alkyl; and $R^5$ represents hydrogen, amino or hydroxy.

6. A compound according to claim 5, wherein;

n is 1, 2, 3, or 4;

$R^1$ represents a hydrogen;

$R^3$ combined with $R^2$ form together a divalent radical selected from the group consisting of —O—CH₂— (a), —NR⁷—CH₂— (b), and —(CR⁸R⁹)$_m$- (c) wherein m represents 1 or 2 and $R^7$, $R^8$, $R^9$ are each independently selected from hydrogen or $C_{1-4}$alkyl;

$R^4$ represents hydrogen, halo, hydroxy, $C_{1-4}$alkyloxy-, or $C_{1-4}$alkyl; and $R^5$ represents hydrogen or hydroxy.

7. A compound according to claim 3 wherein;
n is 1, 2 or 3;
$R^1$ represents a $C_{1-4}$alkyl;
$R^2$ represents a $C_{1-4}$alkyl;
$R^3$ represents hydrogen, $C_{1-4}$alkyl or $C_{1-4}$alkyloxy;
$R^4$ represents hydrogen, halo, —$NR^{11}R^{12}$, $C_{1-4}$alkyloxy-, $C_{1-4}$alkyloxycarbonyl, hydroxycarbonyl or $C_{1-4}$alkyl optionally substituted with one, two or three halo substituents;
$R^5$ represents hydrogen, halo, amino, phenyl, hydroxy, hydroxycarbonyl, Het$^1$, —$NR^{13}R^{14}$, —O—(C=O)—$NR^{21}R^{22}$, —O—(C=O)—$C_{1-4}$alkyl, -carbonyl-$NR^{23}R^{24}$ or $C_{1-4}$alkyloxy optionally substituted with $NR^{17}R^{18}$ or $R^5$ represents —O—(C=O)—$C_{1-4}$alkyl substituted with one or more Het$^3$ or halo substituents; in particular $R^5$ represents hydroxy, amino, methylsulfonylamine, ethylsulfonylamine, methylcarbonylamine, ethylcarbonylamine, dimethylaminosulfonylamine, chloromethylcarbonylamine, trifluoroethylsulfonylamine or methylphenylsulfonylamine;
$R^{11}$ and $R^{12}$ each independently represent hydrogen, $C_{1-4}$alkyl or $C_{1-4}$alkylcarbonyl;
$R^{13}$ and $R^{14}$ each independently represent hydrogen, $C_{1-4}$alkyl, $C_{1-6}$alkyl-$SO_2$—, mono- or di($C_{1-4}$alkyl)amino-$SO_2$—, $Ar^1$—$SO_2$, mono- or di($C_{1-4}$alkyl)amino-carbonyl-, $C_{1-4}$alkyl-oxycarbonyl or $C_{1-4}$alkylcarbonyl- wherein said $C_{1-6}$alkyl-$SO_2$—, $C_{1-4}$alkyl-oxycarbonyl or $C_{1-4}$alkylcarbonyl- are each independently and optionally substituted with one, two or three substituents selected from halo, $C_{1-4}$alkyloxycarbonyl, $NR^{19}R^{20}$ and Het$^2$;
$R^{17}$ and $R^{18}$ each independently represent hydrogen or $C_{1-4}$alkyl;
$R^{19}$ and $R^{20}$ each independently represent hydrogen or $C_{1-4}$alkyl optionally substituted with hydroxy;
$R^{21}$ and $R^{22}$ each independently represent hydrogen or $Ar^2$;
$R^{23}$ and $R^{24}$ each independently represent hydrogen or Het$^4$;
Het$^2$ represents morpholinyl;
Het$^3$ represents morpholinyl;
Het$^4$ represents piperidinyl;
$Ar^1$ represents phenyl substituted with $C_{1-4}$alkyl; and
$Ar^2$ represents phenyl substituted with $C_{1-4}$alkyl.

8. A compound according to claim 7, wherein;
n is 1 or 2;
$R^1$ represents a $C_{1-4}$alkyl;
$R^2$ represents a $C_{1-4}$alkyl;
$R^3$ represents hydrogen;
$R^4$ represents hydrogen, halo, —$NR^{11}R^{12}$, $C_{1-4}$alkyloxy-, or $C_{1-4}$alkyl;
$R^5$ represents hydrogen or hydroxy; in particular hydroxy; and
$R^{11}$ and $R^{12}$ each independently represent hydrogen, $C_{1-4}$alkyl or $C_{1-4}$alkylcarbonyl.

9. A compound selected from the group consisting of;
2,3-dihydro-N-[(1R,3S)-5-hydroxytricyclo[3.3.1.1$^{3,7}$]dec-2-yl]-1,4-benzodioxin-2-carboxamide,
N-[(1R,3S)-5-hydroxytricyclo[3.3.1.1$^{3,7}$]dec-2-yl]-2-methyl-2-(2-methylphenoxy)-propanamide,
N-[(1R,3S)-5-hydroxytricyclo[3.3.1.1$^{3,7}$]dec-2-yl]-2-methyl-2-(4-methylphenoxy)-propanamide,
2-(3,5-dimethylphenoxy)-N-[(1R,3S)-5-hydroxytricyclo[3.3.1.1$^{3,7}$]dec-2-yl]-2-methyl-propanamide,
N-[(1R,3S)-5-hydroxytricyclo[3.3.1.1$^{3,7}$]dec-2-yl]-3-methyl-2-benzofuran-carboxamide,
3,4-dihydro-N-[(1R,3S)-5-hydroxytricyclo[3.3.1.1$^{3,7}$]dec-2-yl]-2H-1-benzopyran-2-carboxamide,
2-(4-chloro-2-methylphenoxy)-N-[(1R,3S)-5-hydroxytricyclo[3.3.1.1$^{3,7}$]dec-2-yl]-2-methyl-propanamide,
2-(4-Chloro-2-methyl-phenoxy)-N-[(1R,3S)-5-methanesulfonylaminotricyclo[3.3.1.1$^{3,7}$]dec-2-yl]-2-methyl-propionamide,
2-(4-Chloro-2-methyl-phenoxy)-N-[(1R,3S)-5-(dimethylamino)sulfonylaminotricyclo[3.3.1.1$^{3,7}$]dec-2-yl]-2-methyl-propionamide,
2-(4-Chloro-phenoxy)-N-[(1R,3S)-5-hydroxytricyclo[3.3.1.1$^{3,7}$]dec-2-yl]-2-methyl-propionamide,
N-[(1R,3S)-5-(dimethylamino)sulfonylaminotricyclo[3.3.1.1$^{3,7}$]dec-2-yl]-2-methyl-2-(3-trifluoromethyl-phenoxy)-propionamide,
N-[(1R,3S)-5-methanesulfonylaminotricyclo[3.3.1.1$^{3,7}$]dec-2-yl]-2-methyl-2-(3-trifluoromethyl-phenoxy)-propionamide,
N-[(1R,3S)-5-aminotricyclo[3.3.1.1$^{3,7}$]dec-2-yl]-2-(2-chloro-phenoxy)-2-methyl-propionamide,
N-[(1R,3S)-5-aminotricyclo[3.3.1.1$^{3,7}$]dec-2-yl]-2-methyl-2-(2-trifluoromethyl-phenoxy)-propionamide,
N-[(1R,3S)-5-Ethanesulfonylaminotricyclo[3.3.1.1$^{3,7}$]dec-2-yl]-2-methyl-2-(3-trifluoromethyl-phenoxy)-propionamide,
(3R,5S)-4-[2-(4-Chloro-2-methyl-phenoxy)-2-methyl-propionylamino]tricyclo[3.3.1.1$^{3.7}$]decane-1-carboxylic acid,
N-[(1R,3S)-5-aminotricyclo[3.3.1.1$^{3.7}$]dec-2-yl]-2-(4-chloro-2-methyl-phenoxy)-2-methyl-propionamide,
2-(4-Chloro-2-methyl-phenoxy)-2-methyl-N-[(1R,3S)-5-(3-methyl-2-oxo-pyrrolidin-1-yl)tricyclo[3.3.1.1$^{3,7}$]dec-2-yl]]-propionamide,
2-(3-Bromo-phenoxy)-2-methyl-N-[(1R,3S)-5-(2-oxo-oxazolidin-3-yl)tricyclo-[3.3.1.1$^{3,7}$]dec-2-yl]]-propionamide,
2-(3-Bromo-phenoxy)-N-[(1R,3S)-5-methanesulfonylaminotricyclo[3.3.1.1$^{3,7}$]-dec-2-yl]-2-methyl-propionamide,
2-(4-Chloro-phenoxy)-N-[(1R,3S)-5-methanesulfonylaminotricyclo[3.3.1.1$^{3,7}$]-dec-2-yl]-2-methyl-propionamide;
N-[(1R,3S)-5-hydroxytricyclo[3.3.1.1$^{3,7}$]dec-2-yl]-2-benzofurancarboxamide; and
N-[(1R,3S)-5-hydroxytricyclo[3.3.1.1$^{3,7}$]dec-2-yl]-7-methoxy-2-benzofuran-carboxamide;
or a N-oxide form, a pharmaceutically acceptable addition salt, or stereochemically isomeric form thereof.

10. A pharmaceutical composition comprising a pharmaceutically acceptable carrier and, as active ingredient, an effective 11β-HSD1 inhibitory amount of a compound as described in claim 1.

11. A process of preparing a pharmaceutical composition as defined in claim 10, comprising intimately mixing said pharmaceutically acceptable carrier with said effective 11β-HSD1 inhibitory amount of said compound.

12. A method for treating insulin resistance, dyslipidemia, obesity or hypertension comprising administering an effective amount of a compound as claimed in claim 1 in combination with an antihypertensive agent to a warm blooded animal suffering from to a warm blooded animal suffering from insulin resistance, dyslipidemia, obesity or hypertension.

13. A compound according to claim 4, wherein $R^5$ represents halo, cyano, amino, phenyl, hydroxy, $C_{1-4}$alkyloxycarbonyl-, hydroxycarbonyl, $NR^{13}R^{14}$ or $C_{1-4}$alkyl optionally substituted with one or more substituents selected from hydroxycarbonyl, phenyl, $C_{1-4}$alkyloxy or $NR^{15}R^{16}$ or $R^5$ represents $C_{1-4}$alkyloxy optionally substituted with one or more substituents selected from hydroxycarbonyl, phenyl, $C_{1-4}$alkyloxy or $NR^{17}R^{18}$.

14. A compound according to claim 5, wherein $R^1$ represents hydrogen or methyl;
   $R^4$ represents methyl, ethyl, methoxy, fluoro, chloro or bromo; and
   $R^5$ represents amino or hydroxy.

15. A compound according to claim 6, wherein $R^4$ represents methyl, ethyl, methoxy, fluoro, chloro or bromo; and $R^5$ represents hydroxy.

16. A compound according to claim 7, wherein $R^1$ represents methyl;
   $R^2$ represents methyl;
   $R^3$ represents hydrogen, methyl or methoxy;
   $R^4$ represents methyl, ethyl, dimethylamine, trifluoromethyl, methoxycarbonyl, methoxy, fluoro, chloro or bromo;
   $R^{11}$ and $R^{12}$ each represent methyl;
   $R^{17}$ and $R^{18}$ each independently represent methyl;
   $R^{19}$ and $R^{20}$ each independently represent hydrogen, methyl or hydroxyethyl;
   $R^{21}$ and $R^{22}$ each independently represent hydrogen or methylphenyl;
   $R^{23}$ and $R^{24}$ each independently represent hydrogen or piperidinyl.

17. A compound according to claim 8, wherein $R^1$ represents methyl;
   $R^2$ represents methyl;
   $R^4$ represents methyl, ethyl, methoxy, fluoro, chloro or bromo.

18. A compound according to claim 1, wherein
   $R^2$ represents hydrogen, $C_{1-4}$alkyl, or $C_{1-4}$alkyloxy-; and
   $R^3$ represents hydrogen, $C_{1-4}$alkyl, or $C_{1-4}$alkyloxy.

19. A compound according to claim 3, wherein
   $R^2$ represents hydrogen, $C_{1-4}$alkyl, or $C_{1-4}$alkyloxy-; and
   $R^3$ represents hydrogen, $C_{1-4}$alkyl, or $C_{1-4}$alkyloxy.

* * * * *

UNITED STATES PATENT AND TRADEMARK OFFICE
CERTIFICATE OF CORRECTION

PATENT NO.         : 8,344,181 B2                                   Page 1 of 1
APPLICATION NO.    : 11/661470
DATED              : January 1, 2013
INVENTOR(S)        : Libuse Jaroskova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 977 days.

Signed and Sealed this
Fifteenth Day of July, 2014

Michelle K. Lee
*Deputy Director of the United States Patent and Trademark Office*